(12) United States Patent
Small et al.

(10) Patent No.: US 12,241,076 B2
(45) Date of Patent: Mar. 4, 2025

(54) GENE RESPONSIBLE FOR CYTOPLASMIC MALE STERILITY

(71) Applicant: VILMORIN & CIE, Paris (FR)

(72) Inventors: Ian Small, Wattle Grove (AU); Joanna Melonek, Crawley (AU)

(73) Assignee: VILMORIN & CIE, Paris (FR)

( * ) Notice: Subject to any disclaimer, the term of this patent is extended or adjusted under 35 U.S.C. 154(b) by 334 days.

(21) Appl. No.: 17/429,176

(22) PCT Filed: Feb. 6, 2020

(86) PCT No.: PCT/EP2020/053036
§ 371 (c)(1),
(2) Date: Aug. 6, 2021

(87) PCT Pub. No.: WO2020/161261
PCT Pub. Date: Aug. 13, 2020

(65) Prior Publication Data
US 2022/0098612 A1    Mar. 31, 2022

(30) Foreign Application Priority Data
Feb. 6, 2019   (EP) .................................... 19305141

(51) Int. Cl.
*C12N 15/82* (2006.01)
*C07K 14/415* (2006.01)
*C12Q 1/6895* (2018.01)

(52) U.S. Cl.
CPC ........ *C12N 15/8289* (2013.01); *C07K 14/415* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

2021/0269822 A1*  9/2021  Rohde ................ C12N 15/8213

OTHER PUBLICATIONS

EBI Accession: AP013103 (Oct. 4, 2013), T. timopheevii Mitochondrial Genome (Year: 2013).*
Barkan and Small, 2014, Annual Review of Plant Biology 65: 415-442 (Year: 2014).*
Tyrka et al, 2021, International Journal of Molecular Sciences 22: 9146 (Year: 2021).*
Shahinnia et al, 2020, Frontiers in Plant Science 11: 577475 (Year: 2020).*
Gupta et al , 2019, Theoretical and Applied Genetics 132: 2463-2483 (Year: 2019).*
Tsunewaki, 2015, Theoretical and Applied Genetics 128: 723-732 (Year: 2015).*
"Triticum timopheevii mitochondrial DNA, complete sequence.;" EMBL04; 2013; retrieved from EBI accession No. EM_STD:AP013106; Database accession No. AP013106; XP002792459.
"SubName: Full=Uncharacterized protein {ECO:0000313|EnsemblPlants:TraesCS1A02G067600.1.cds1};" UniProt05; 2018; retrieved from EBI accession No. UniProt:A0A3B5XW41; Database accession No. A0A3B5XW41; XP002792460.
Song et al.; "Influence of nuclear background on transcription of a chimeric gene (orf256) and coxI in fertile and cytoplasmic male sterile wheats;" Genome; 1994; pp. 203-209; vol. 37, No. 2.
El-Shehawi et al.; "Genetic Fingerprinting of Wheat and Its Progenitors by Mitochondrial Gene orf256;" Biomolecules; 2012; pp. 228-239; vol. 2, No. 2.
Mar. 17, 2020 Search Report issued in International Patent Application No. PCT/EP2020/053036.
Mar. 17, 2020 Written Opinion of the International Searching Authority issued in International Patent Application No. PCT/EP2020/053036.
Barkan et al. "A Combinatorial Amino Acid Code for RNA Recognition by Pentatricopeptide Repeat Proteins", PLOS Genetics, vol. 8, Issue 8, Aug. 16, 2012, pp. 1-8.

* cited by examiner

Primary Examiner — Anne Kubelik
Assistant Examiner — Aleksandar Radosavljevic
(74) Attorney, Agent, or Firm — Oliff PLC

(57) ABSTRACT

An isolated nucleic acid encoding Orf279 protein of amino acid sequence at least 95% identical to SEQ ID NO: 4, methods for detecting orf279 DNA, orf279 RNA or Orf279 protein and method for identifying functional Rf gene encoding a protein able to bind to orf279 RNA.

3 Claims, 10 Drawing Sheets

Figure 1A:
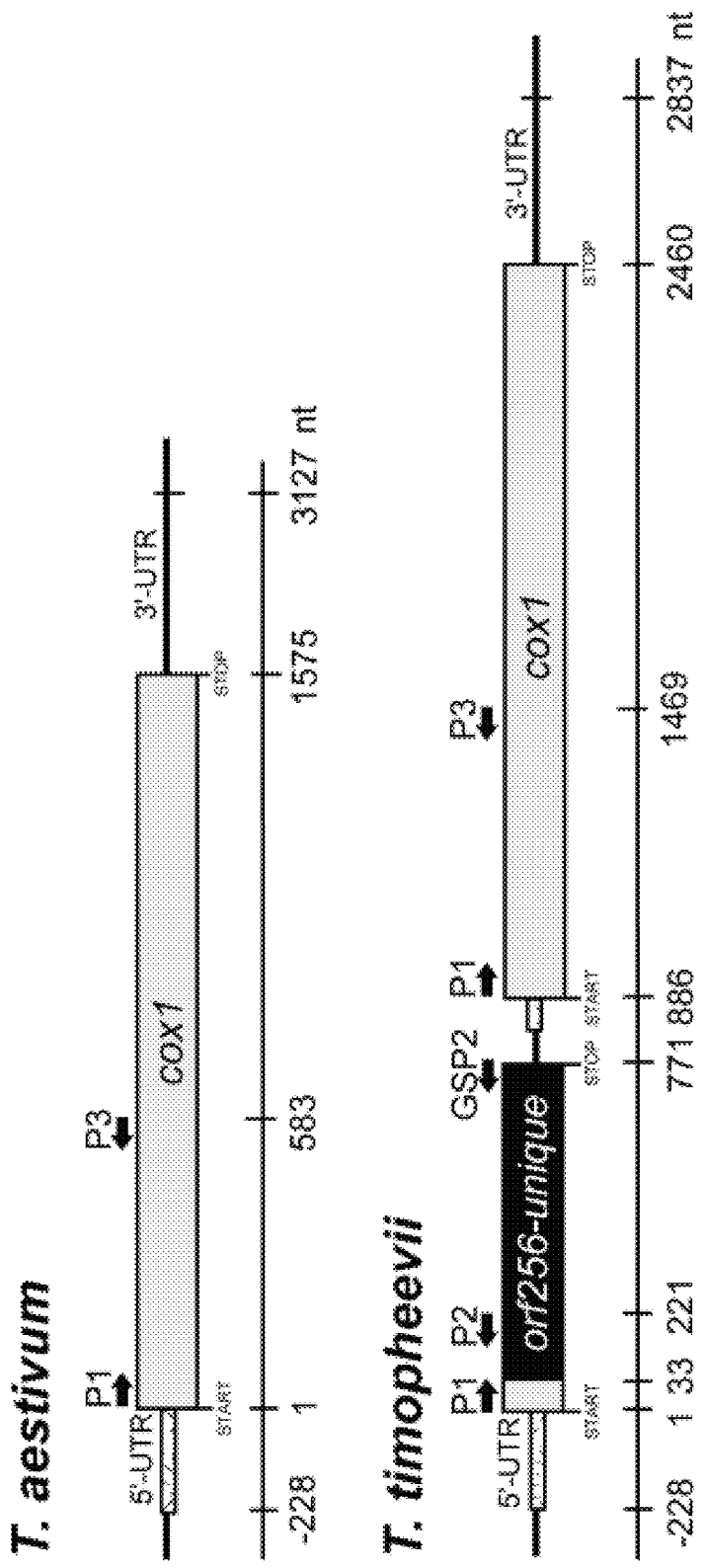

Specification includes a Sequence Listing.

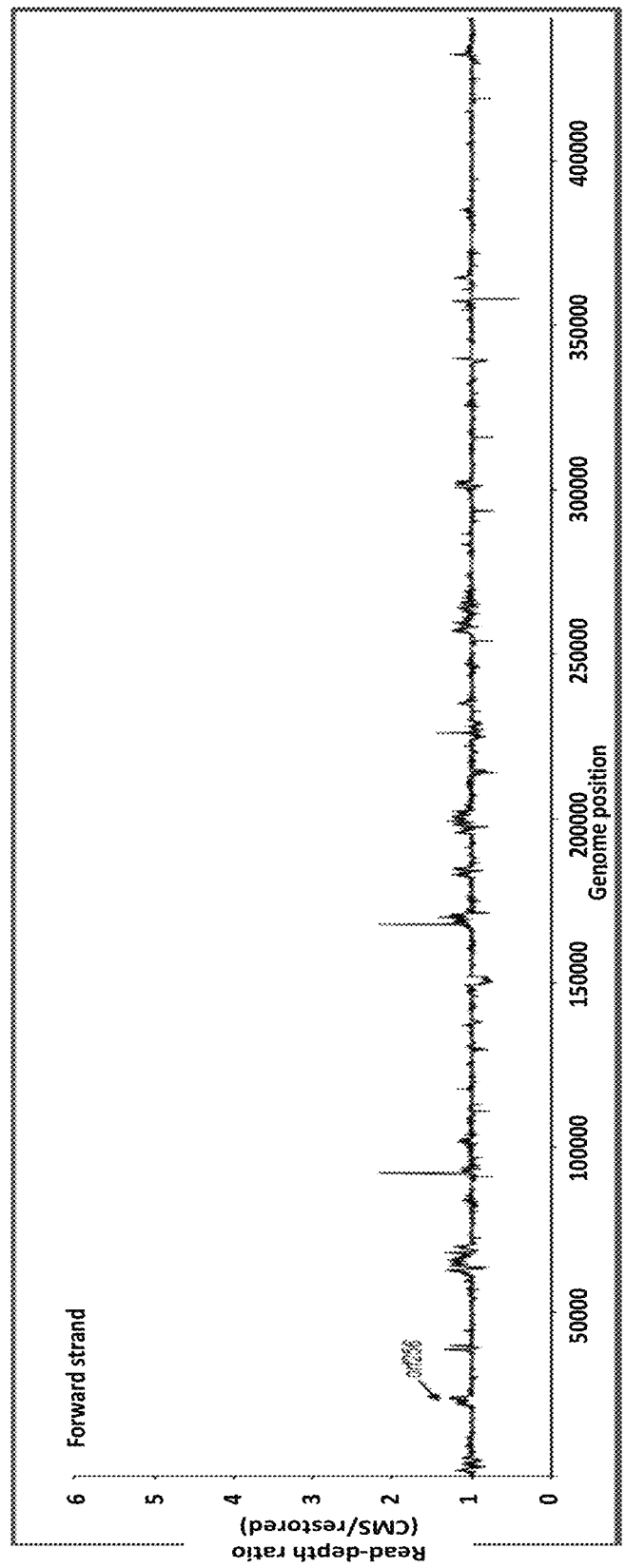

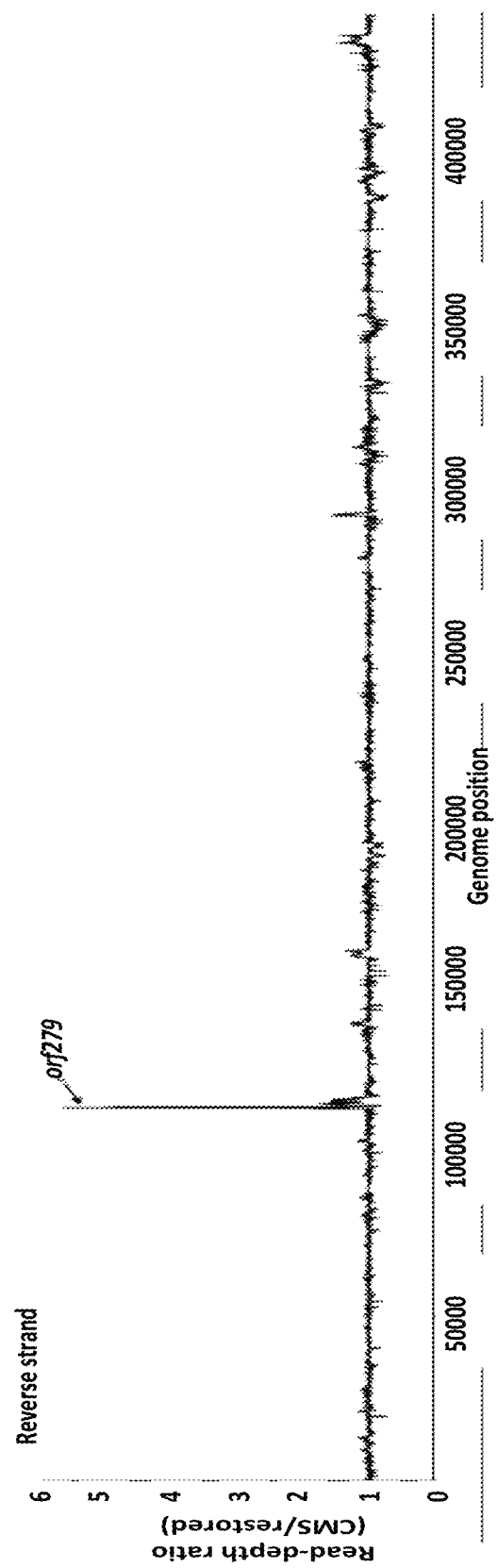

Figure 3
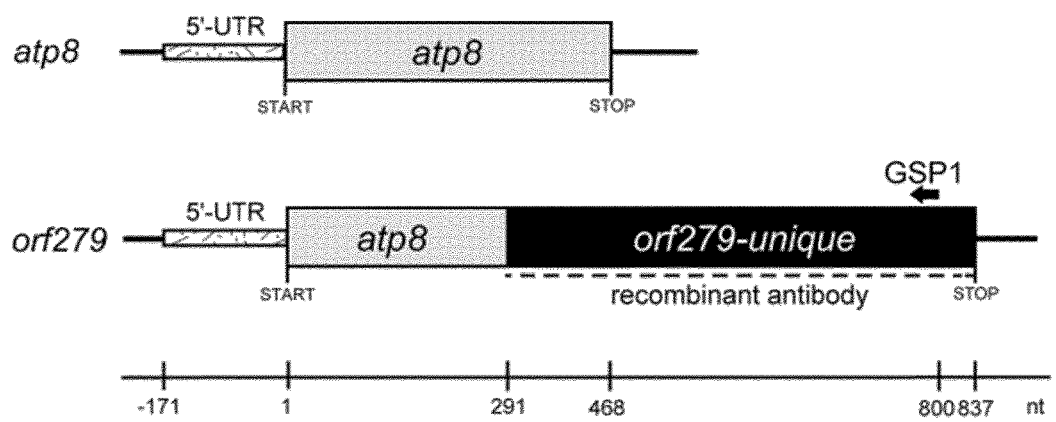
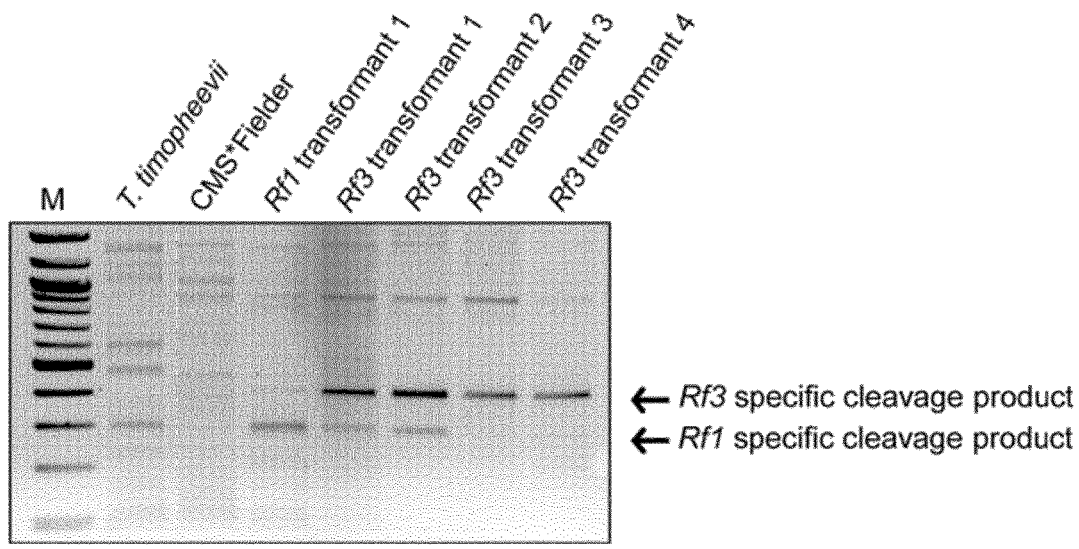

Figure 4

A

SRorf279

| # PPR motif | Original sequence | Optimised sequence |
|---|---|---|
| | 1 2 3 4 5 6 7 8 9 10 11 12 13 14 15 16 17 18 | 1 2 3 4 5 6 7 8 9 10 11 12 13 14 15 16 17 18 |
| position 5 | G S N N N T N T N S H N N S N D N G | N S N N N T N T N S H N N S N N N G |
| position 35 | N N N N D D D D S D N D D T S N N S | N N N N D D D D S N D D T D N D S |
| RNA base | caccugugcacuuauuua | caccugugcacuuauuua |
| SEQ ID NO: 41 | | |

B

SRorf256

| # PPR motif | Original sequence | Optimised sequence |
|---|---|---|
| | 1 2 3 4 5 6 7 8 9 10 11 12 13 14 15 16 17 18 | 1 2 3 4 5 6 7 8 9 10 11 12 13 14 15 16 17 18 |
| position 5 | N N N S N N N C T S Q N N S N G N G | N N N S N N N C T S N N N N N G N G |
| position 35 | D N D S D N D D N D N D D T T S N S | D N D S D N D D N D N N D D N S N D |
| RNA base | ucuaucugagccuuuacg | ucuaucugagccuuuacg |
| SEQ ID NO: 42 | | |

Figure 5

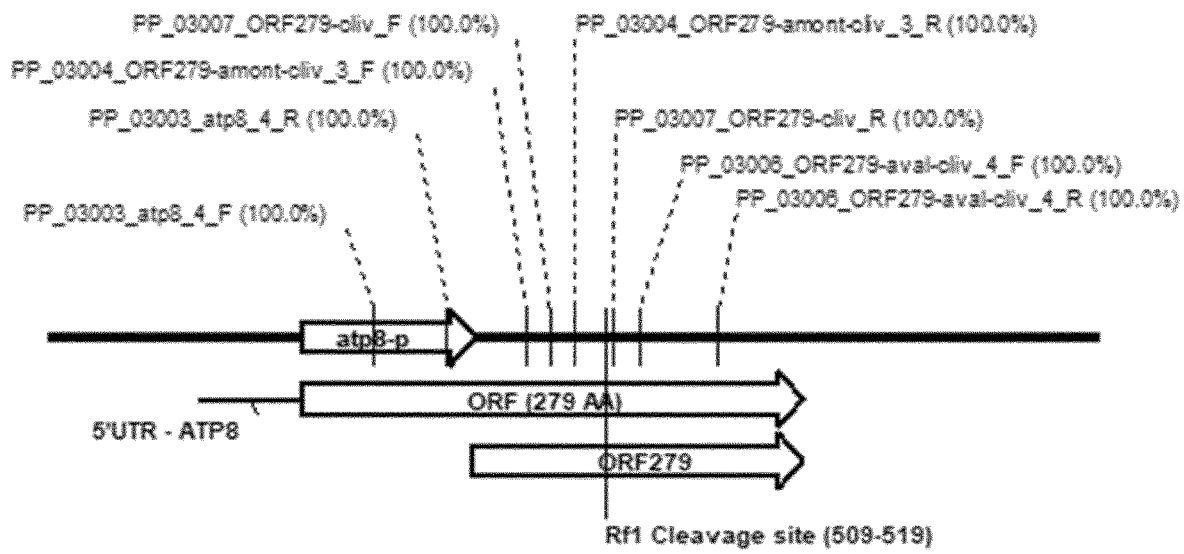

|  | Original sequence | Optimised sequence 1 | Optimised sequence 2 |
|---|---|---|---|
| # PPR motif | 123456789 11111111112 01234567890 | 123456789 11111111112 01234567890 | 123456789 11111111112 01234567890 |
| position 5 | AGNNNSNANSRSNGNSNTNS | AGNNNSNANSNNNGNSNTNS | AGNNNSNANSNNNGNSNTNS |
| position 35 | QNNNDDDDNDDNCTCDNNEA | QNNNDDDDNNDNCTCDNNEA | QNNNDDDDNNDNCTCDNNEA |
| RNA base SEQ ID NO: 43 | caccugugcacuuauuuaug | caccugugcacuuauuuaug | caccugugcacuuauuuaug |

SEQUENCE LISTING

```
<160> NUMBER OF SEQ ID NOS: 54

<210> SEQ ID NO 1
<211> LENGTH: 837
<212> TYPE: DNA
<213> ORGANISM: Triticum timopheevii

<400> SEQUENCE: 1
atgcctcaac ttgataaatt aacttatttc tcacaattct tctggttatg tcttctcctc      60
tttacttttt atattctctt atttaataat aataatggaa tacttggaat tagtagaatt     120
ctcaaactac ggaaccaact gctttcgcac cgggggggcg agatccggag caaggaccct     180
aagaatctgg aagatatctc gagaaaaggt tttagcaccg gtctctcata tatgtactcc     240
agtttatccg aagtatccca atggtgtaag accgtcgact atttgggaaa taagatatct     300
tcttcaatct ttctatacta tcttaggggc gtcctttgcc caatttgcct cttattttt      360 aaatttctta tttctttcgc cttcacctgt gcacttattt atgtattcaa gggggggggt     420
```

```
ttcgtggcta tggctgctac aaacggagcc tcttcttcct ttctggagag ctcaggtgaa    480
atagatgcac tgttacaaac aacaacaaca acacgaacac ccgaaaacgc ggattacgaa    540
gacgataata cttctgtaaa tcaagaattc ctcgaagacg acaaagggc ccgacaggct     600 aaactacggg agttagaaag actcattctc cagcaatata aggatttcat ccgacagaaa    660
tatccatgga tacctaaagg cgacatcctt ctcccgagca tgaagggtgg agttgtcgag    720
gacgtaatgg aaaaattaga attggaaacg tattccagta gcgacttgac tgattggatc    780
aaccatttgc gggcaaatcc gaaaacatta aattttatct tcaaggattt tgtcgcg       837

<210> SEQ ID NO 2
<211> LENGTH: 290
<212> TYPE: DNA
<213> ORGANISM: Triticum timopheevii

<400> SEQUENCE: 2
atgcctcaac ttgataaatt aacttatttc tcacaattct tctggttatg tcttctcctc     60
tttacttttt atattctctt atttaataat aataatggaa tacttggaat tagtagaatt    120
ctcaaactac ggaaccaact gctttcgcac cggggggggcg agatccggag caaggaccct    180
aagaatctgg aagatatctc gagaaaaggt tttagcaccg gtctctcata tatgtactcc    240
agtttatccg aagtatccca atggtgtaag accgtcgact atttgggaaa                290

<210> SEQ ID NO 3
<211> LENGTH: 547
<212> TYPE: DNA
<213> ORGANISM: Triticum timopheevii

<400> SEQUENCE: 3
taagatatct tcttcaatct ttctatacta tcttaggggc gtcctttgcc caatttgcct     60
cttatttttt aaatttctta tttctttcgc cttcacctgt gcacttattt atgtattcaa    120 ggggggggt tcgtggcta tggctgctac aaacggagcc tcttcttcct ttctggagag      180
ctcaggtgaa atagatgcac tgttacaaac aacaacaaca acacgaacac ccgaaaacgc    240
ggattacgaa gacgataata cttctgtaaa tcaagaattc ctcgaagacg acaaagggc    300 ccgacaggct aaactacggg agttagaaag actcattctc cagcaatata aggatttcat    360
ccgacagaaa tatccatgga tacctaaagg cgacatcctt ctcccgagca tgaagggtgg    420
agttgtcgag gacgtaatgg aaaaattaga attggaaacg tattccagta gcgacttgac    480
tgattggatc aaccatttgc gggcaaatcc gaaaacatta aattttatct tcaaggattt    540
tgtcgcg                                                              547

<210> SEQ ID NO 4
<211> LENGTH: 279
<212> TYPE: PRT
<213> ORGANISM: Triticum timopheevii

<400> SEQUENCE: 4

Met Pro Gln Leu Asp Lys Leu Thr Tyr Phe Ser Gln Phe Phe Trp Leu
1               5                   10                  15

Cys Leu Leu Leu Phe Thr Phe Tyr Ile Leu Phe Asn Asn Asn Asn
            20                  25                  30

Gly Ile Leu Gly Ile Ser Arg Ile Leu Lys Leu Arg Asn Gln Leu Leu
        35                  40                  45

Ser His Arg Gly Gly Glu Ile Arg Ser Lys Asp Pro Lys Asn Leu Glu
    50                  55                  60
```

-continued

```
Asp Ile Ser Arg Lys Gly Phe Ser Thr Gly Leu Ser Tyr Met Tyr Ser
 65                  70                  75                  80

Ser Leu Ser Glu Val Ser Gln Trp Cys Lys Thr Val Asp Tyr Leu Gly
                 85                  90                  95

Asn Lys Ile Ser Ser Ser Ile Phe Leu Tyr Tyr Leu Arg Gly Val Leu
            100                 105                 110

Cys Pro Ile Cys Leu Leu Phe Phe Lys Phe Leu Ile Ser Phe Ala Phe
        115                 120                 125

Thr Cys Ala Leu Ile Tyr Val Phe Lys Gly Gly Gly Phe Val Ala Met
    130                 135                 140

Ala Ala Thr Asn Gly Ala Ser Ser Ser Phe Leu Glu Ser Ser Gly Glu
145                 150                 155                 160

Ile Asp Ala Leu Leu Gln Thr Thr Thr Thr Thr Arg Thr Pro Glu Asn
                165                 170                 175

Ala Asp Tyr Glu Asp Asp Asn Thr Ser Val Asn Gln Glu Phe Leu Glu
            180                 185                 190

Asp Gly Gln Arg Ala Arg Gln Ala Lys Leu Arg Glu Leu Glu Arg Leu
        195                 200                 205

Ile Leu Gln Gln Tyr Lys Asp Phe Ile Arg Gln Lys Tyr Pro Trp Ile
    210                 215                 220

Pro Lys Gly Asp Ile Leu Leu Pro Ser Met Lys Gly Gly Val Val Glu
225                 230                 235                 240

Asp Val Met Glu Lys Leu Glu Leu Glu Thr Tyr Ser Ser Ser Asp Leu
                245                 250                 255

Thr Asp Trp Ile Asn His Leu Arg Ala Asn Pro Lys Thr Leu Asn Phe
            260                 265                 270

Ile Phe Lys Asp Phe Val Ala
        275

<210> SEQ ID NO 5
<211> LENGTH: 183
<212> TYPE: PRT
<213> ORGANISM: Triticum timopheevii

<400> SEQUENCE: 5

Asn Lys Ile Ser Ser Ser Ile Phe Leu Tyr Tyr Leu Arg Gly Val Leu
 1               5                  10                  15

Cys Pro Ile Cys Leu Leu Phe Phe Lys Phe Leu Ile Ser Phe Ala Phe
             20                  25                  30

Thr Cys Ala Leu Ile Tyr Val Phe Lys Gly Gly Gly Phe Val Ala Met
         35                  40                  45

Ala Ala Thr Asn Gly Ala Ser Ser Ser Phe Leu Glu Ser Ser Gly Glu
     50                  55                  60

Ile Asp Ala Leu Leu Gln Thr Thr Thr Thr Thr Arg Thr Pro Glu Asn
 65                  70                  75                  80

Ala Asp Tyr Glu Asp Asp Asn Thr Ser Val Asn Gln Glu Phe Leu Glu
                 85                  90                  95

Asp Gly Gln Arg Ala Arg Gln Ala Lys Leu Arg Glu Leu Glu Arg Leu
            100                 105                 110

Ile Leu Gln Gln Tyr Lys Asp Phe Ile Arg Gln Lys Tyr Pro Trp Ile
        115                 120                 125

Pro Lys Gly Asp Ile Leu Leu Pro Ser Met Lys Gly Gly Val Val Glu
    130                 135                 140

Asp Val Met Glu Lys Leu Glu Leu Glu Thr Tyr Ser Ser Ser Asp Leu
```

```
              145                 150                 155                 160
Thr Asp Trp Ile Asn His Leu Arg Ala Asn Pro Lys Thr Leu Asn Phe
              165                 170                 175
Ile Phe Lys Asp Phe Val Ala
              180
```

<210> SEQ ID NO 6
<211> LENGTH: 17
<212> TYPE: DNA
<213> ORGANISM: artificial sequence
<220> FEATURE:
<223> OTHER INFORMATION: primer PP_03004_ORF279-amont-cliv_3_F
<400> SEQUENCE: 6
ttcgccttca cctgtgc                                                    17

<210> SEQ ID NO 7
<211> LENGTH: 20
<212> TYPE: DNA
<213> ORGANISM: artificial sequence
<220> FEATURE:
<223> OTHER INFORMATION: primer PP_03004_ORF279-amont-cliv_3_R
<400> SEQUENCE: 7
cctgagctct ccagaaagga                                                 20

<210> SEQ ID NO 8
<211> LENGTH: 20
<212> TYPE: DNA
<213> ORGANISM: artificial sequence
<220> FEATURE:
<223> OTHER INFORMATION: primer PP_03006_ORF279-aval-cliv_4_F
<400> SEQUENCE: 8
aattcctcga agacggacaa                                                 20

<210> SEQ ID NO 9
<211> LENGTH: 19
<212> TYPE: DNA
<213> ORGANISM: artificial sequence
<220> FEATURE:
<223> OTHER INFORMATION: primer PP_03006_ORF279-aval-cliv_4_R
<400> SEQUENCE: 9
caactccacc cttcatgct                                                  19

<210> SEQ ID NO 10
<211> LENGTH: 17
<212> TYPE: DNA
<213> ORGANISM: artificial sequence
<220> FEATURE:
<223> OTHER INFORMATION: primer PP_03007_ORF279-cliv_F
<400> SEQUENCE: 10
gggggtttcg tggctat                                                    17

<210> SEQ ID NO 11
<211> LENGTH: 19
<212> TYPE: DNA
<213> ORGANISM: artificial sequence
<220> FEATURE:
<223> OTHER INFORMATION: primer PP_03007_ORF279-cliv_R
<400> SEQUENCE: 11
cttcgtaatc cgcgttttc                                                  19

<210> SEQ ID NO 12
<211> LENGTH: 20
<212> TYPE: DNA
<213> ORGANISM: artificial sequence
<220> FEATURE:
<223> OTHER INFORMATION: primer PP_03003_atp8_4_F

<400> SEQUENCE: 12
caaactacgg aaccaactgc                                                  20

<210> SEQ ID NO 13
<211> LENGTH: 21
<212> TYPE: DNA
<213> ORGANISM: artificial sequence
<220> FEATURE:
<223> OTHER INFORMATION: primer PP_03003_atp8_4_R

<400> SEQUENCE: 13
ccattgggat acttcggata a                                                21

<210> SEQ ID NO 14
<211> LENGTH: 1992
<212> TYPE: DNA
<213> ORGANISM: artificial sequence
<220> FEATURE:
<223> OTHER INFORMATION: proZmUBI_intZmUBI

<400> SEQUENCE: 14
gtgcagcgtg acccggtcgt gccccctctct agagataatg agcattgcat gtctaagtta    60
taaaaaatta ccacatattt ttttttgtcac acttgtttga agtgcagttt atctatcttt   120
atacatatat ttaaacttta ctctacgaat aatataatct atagtactac aataatatca   180
gtgttttaga gaatcatata aatgaacagt tagacatggt ctaaaggaca attgagtatt   240
ttgacaacag gactctacag ttttatcttt ttagtgtgca tgtgttctcc tttttttttg   300
caaatagctt cacctatata atacttcatc cattttatta gtacatccat ttagggttta   360
gggttaatgg tttttataga ctaatttttt tagtacatct attttattct atttttagcct  420 ctaaattaag aaaactaaaa ctctatttta gttttttttat ttaataattt agatataaaa   480
tagaataaaa taaagtgact aaaaattaaa caaatacccct ttaagaaatt aaaaaaacta   540
aggaaacatt tttcttgttt cgagtagata atgccagcct gttaaacgcc gtcgacgagt   600
ctaacggaca ccaaccagcg aaccagcagc gtcgcgtcgg gccaagcgaa gcagacggca   660
cggcatctct gtcgctgcct ctggaccccct ctcgagagtt ccgctccacc gttggacttg   720
ctccgctgtc ggcatccaga aattgcgtgg cggagcggca gacgtgagcc ggcacggcag   780
gcggcctcct cctcctctca cggcaccggc agctacgggg gattccttc ccaccgctcc   840 ttcgcttcc cttcctcgcc cgccgtaata aatagacacc cctccacac cctctttccc   900 caacctcgtt tgttcggag cgcacacaca caaccaga tctcccccaa atccaccgt       960 cggcacctcc gcttcaaggt acgccgctcg tcctccccccc cccccctct ctaccttctc  1020 tagatcggcg ttccggtcca tggttagggc ccggtagttc tacttctgtt catgtttgtg  1080
ttagatccgt gtttgtgtta gatccgtgct gctagcgttc gtacacggat gcgacctgta  1140
cgtcagacac gttctgattg ctaacttgcc agtgtttctc tttggggaat cctgggatgg  1200
ctctagccgt tccgcagacg ggatcgattt catgattttt tttgtttcgt tgcatagggt  1260
ttggtttgcc cttttccttt atttcaatat atgccgtgca cttgtttgtc gggtcatctt  1320

-continued

```
ttcatgcttt tttttgtctt ggttgtgatg atgtggtctg gttgggcggt cgttctagat    1380
cggagtagaa ttaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg cttttttgttc   1560
gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttttag ccctgccttc   1920
atacgctatt tatttgcttg gtactgtttc ttttgtcgat gctcaccctg ttgtttggtg    1980
ttacttctgc ag                                                        1992
```

<210> SEQ ID NO 15
<211> LENGTH: 792
<212> TYPE: PRT
<213> ORGANISM: Triticum aestivum

<400> SEQUENCE: 15

```
Met Pro Arg Phe Ser Ser Thr Thr Pro Met Ser Pro Pro Arg Leu Leu
1               5                   10                  15

Leu Arg Leu Gly Ala Arg His Ser Ser Thr Ser His Pro Ser Arg
            20                  25                  30

Ile Trp Asp Pro His Ala Ala Phe Ala Ala Thr Gln Arg Ala Arg
        35                  40                  45

Ser Gly Thr Leu Thr Thr Glu Asp Ala His His Leu Phe Asp Glu Leu
    50                  55                  60

Leu Arg Gln Gly Asn Pro Val Gln Glu Arg Pro Leu Thr Asn Phe Leu
65                  70                  75                  80

Ala Ala Leu Ala Arg Ala Pro Ala Ser Ala Phe Cys Ser Asp Gly Pro
                85                  90                  95

Ala Leu Ala Val Ala Leu Phe Gly Arg Leu Ser Arg Gly Ala Gly Arg
            100                 105                 110

Arg Val Ala Gln Pro Asn Val Phe Thr Tyr Gly Val Leu Met Asp Cys
        115                 120                 125

Cys Cys Arg Ala Arg Arg Leu Asp Leu Ala Ile Ala Phe Phe Ala Arg
    130                 135                 140

Leu Leu Lys Thr Gly Leu Glu Ala Asn Gln Val Ile Phe Cys Thr Leu
145                 150                 155                 160

Leu Lys Gly Leu Cys His Ala Lys Arg Ser Asp Glu Ala Leu Asp Val
                165                 170                 175

Val Leu His Arg Met Pro Glu Leu Gly Cys Thr Pro Asn Val Val Ala
            180                 185                 190

Tyr Thr Thr Val Ile His Gly Phe Leu Lys Glu Gly Gln Val Gly Lys
        195                 200                 205

Ala Cys Asn Leu Phe His Gly Met Ala Gln Gln Gly Val Ala Pro Asp
    210                 215                 220

Val Val Thr Tyr Asn Ser Val Ile Asp Ala Leu Cys Lys Ala Arg Ala
225                 230                 235                 240

Met Asp Lys Ala Glu Tyr Phe Leu Arg Glu Met Val Asp Asn Gly Val
                245                 250                 255
```

```
Val Pro Asn Asn Val Thr Tyr Asn Ser Leu Ile His Gly Tyr Ser Ser
        260                 265                 270

Leu Gly His Gln Lys Glu Ala Val Arg Val Leu Lys Glu Met Thr Arg
        275                 280                 285

Gln Gly Ile Ile Pro Asp Val Ile Thr Cys Thr Ser Leu Met Thr Phe
        290                 295                 300

Leu Cys Lys Asn Gly Lys Ser Lys Glu Ala Ala Glu Ile Phe Asp Ser
305                 310                 315                 320

Met Ala Thr Lys Gly Leu Lys His Asp Ala Val Ser Tyr Ala Ile Leu
                325                 330                 335

Leu His Gly Tyr Ala Thr Glu Gly Cys Leu Val Asp Met Ile Asn Leu
                340                 345                 350

Phe Asn Ser Met Asp Arg Asp Cys Ile Leu Pro Asn Cys His Ile Phe
                355                 360                 365

Asn Ile Leu Ile Tyr Ala Tyr Ala Lys Ser Gly Lys Leu Asp Lys Ala
        370                 375                 380

Met Leu Ile Phe Arg Asp Met Gln Lys Gln Gly Val Ser Pro Asp Ala
385                 390                 395                 400

Phe Thr Tyr Ser Thr Leu Ile His Ala Phe Cys Lys Lys Gly Arg Leu
                405                 410                 415

Asp Asp Ala Met Ile Lys Phe Asn Gln Met Val Asp Thr Gly Val Arg
                420                 425                 430

Gln Gly Thr Ala Val Tyr Gly Ser Leu Ile Gln Gly Phe Cys Thr His
        435                 440                 445

Gly Asp Leu Val Lys Gly Lys Glu Leu Val Thr Glu Met Met Asn Lys
450                 455                 460

Gly Ile Pro Pro Asp Ile Met Phe Phe His Ser Ile Met Gln Asn
465                 470                 475                 480

Leu Cys Thr Glu Gly Arg Val Val Glu Ala Arg Asp Ile Leu Gly Leu
                485                 490                 495

Ile Ala His Ile Gly Met Arg Pro Asn Val Cys Thr Phe Asn Ile Leu
                500                 505                 510

Ile Gly Gly Tyr Cys Leu Val Arg Lys Met Glu Asp Ala Ser Lys Ile
                515                 520                 525

Phe His Asp Met Met Ser Tyr Gly Leu Glu Pro Ser Asn Val Thr Tyr
        530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu Arg Lys Gly Leu Lys Pro Thr Thr
                565                 570                 575

Phe Asn Tyr Asn Ile Ile Leu Asp Gly Leu Phe Leu Ala Gly Arg Thr
                580                 585                 590

Val Ala Ala Lys Glu Lys Phe Asp Glu Met Val Glu Ser Gly Val Ser
        595                 600                 605

Met Cys Ile Ser Thr Tyr Ser Ile Val Leu Arg Gly Leu Cys Arg Asn
        610                 615                 620

Asn Cys Ser Gly Glu Ala Ile Thr Leu Phe Gln Thr Leu Ser Ala Met
625                 630                 635                 640

Asp Val Lys Phe Asn Ile Arg Ile Val Asn Ile Met Ile Asp Ala Phe
                645                 650                 655

Phe Arg Val Gln Arg Lys Gln Glu Ala Lys Asp Leu Phe Ala Ala Ile
                660                 665                 670
```

```
Thr Ala Asn Gly Leu Val Ala Asn Val Phe Thr Tyr Ser Leu Met Met
            675                 680                 685

Thr Asn Leu Ile Lys Glu Gly Ser Val Glu Ala Asp Thr Leu Phe
        690                 695                 700

Leu Ser Met Glu Met Ser Gly Cys Thr Ser Asn Ser Trp Met Leu Asn
705                 710                 715                 720

Leu Ile Ile Arg Gly Leu Leu Glu Lys Gly Glu Ile Val Lys Ala Gly
                725                 730                 735

Cys Tyr Met Ser Lys Val Asp Ala Lys Ser Tyr Ser Leu Glu Ala Lys
            740                 745                 750

Thr Val Ser Leu Leu Ile Tyr Leu Phe Ser Gly Lys Gly Lys Tyr Arg
        755                 760                 765

Glu His Ile Arg Leu Leu Pro Thr Lys Tyr Gln Phe Leu Glu Glu Ala
    770                 775                 780

Ala Thr Val Glu Trp Phe Ala Ile
785                 790

<210> SEQ ID NO 16
<211> LENGTH: 978
<212> TYPE: DNA
<213> ORGANISM: Zea mays

<400> SEQUENCE: 16
```

| | | | | | |
|---|---|---|---|---|---|
| gtgcagcgtg | acccggtcgt | gcccctctct | agagataatg | agcattgcat | gtctaagtta | 60 |
| taaaaaatta | ccacatattt | tttttgtcac | acttgtttga | agtgcagttt | atctatcttt | 120 |
| atacatatat | ttaaacttta | ctctacgaat | aatataatct | atagtactac | aataatatca | 180 |
| gtgttttaga | gaatcatata | aatgaacagt | tagacatggt | ctaaaggaca | attgagtatt | 240 |
| ttgacaacag | gactctacag | ttttatcttt | ttagtgtgca | tgtgttctcc | ttttttttg | 300 |
| caaatagctt | cacctatata | atacttcatc | cattttatta | gtacatccat | ttagggttta | 360 |
| gggttaatgg | tttttataga | ctaatttttt | tagtacatct | attttattct | attttagcct | 420 |
| ctaaattaag | aaaactaaaa | ctctatttta | gttttttat | ttaataattt | agatataaaa | 480 |
| tagaataaaa | taaagtgact | aaaaattaaa | caaatacct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggacccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattcctttc | ccaccgctcc | 840 |
| ttcgctttcc | cttcctcgcc | cgccgtaata | aatagacacc | cctccacac | cctctttccc | 900 |
| caacctcgtg | ttgttcggag | cgcacacaca | cacaaccaga | tctcccccaa | atccacccgt | 960 |
| cggcacctcc | gcttcaag | | | | | 978 |

```
<210> SEQ ID NO 17
<211> LENGTH: 1014
<212> TYPE: DNA
<213> ORGANISM: Zea mays

<400> SEQUENCE: 17
```

| | | | | | |
|---|---|---|---|---|---|
| gtacgccgct | cgtcctcccc | ccccccccct | ctctaccttc | tctagatcgg | cgttccggtc | 60 |
| catggttagg | gcccggtagt | tctacttctg | ttcatgtttg | tgttagatcc | gtgtttgtgt | 120 |
| tagatccgtg | ctgctagcgt | tcgtacacgg | atgcgacctg | tacgtcagac | acgttctgat | 180 |

```
tgctaacttg ccagtgtttc tctttgggga atcctgggat ggctctagcc gttccgcaga      240
cgggatcgat ttcatgattt tttttgtttc gttgcatagg gtttggtttg ccctttttcct    300 ttatttcaat atatgccgtg cacttgtttg tcgggtcatc ttttcatgct ttttttttgtc    360 ttggttgtga tgatgtggtc tggttgggcg gtcgttctag atcggagtag aattaattct     420
gtttcaaact acctggtgga tttattaatt ttggatctgt atgtgtgtgc catacatatt     480
catagttacg aattgaagat gatggatgga aatatcgatc taggataggt atacatgttg     540
atgcgggttt tactgatgca tatacagaga tgcttttttgt tcgcttggtt gtgatgatgt    600
ggtgtggttg ggcggtcgtt cattcgttct agatcggagt agaatactgt ttcaaactac     660
ctggtgtatt tattaatttt ggaactgtat gtgtgtgtca tacatcttca tagttacgag     720
tttaagatgg atgaaatat cgatctagga taggtataca tgttgatgtg gttttactg       780 atgcatatac atgatggcat atgcagcatc tattcatatg ctctaacctt gagtacctat     840
ctattataat aaacaagtat gttttataat tattttgatc ttgatatact tggatgatgg     900
catatgcagc agctatatgt ggattttttt agccctgcct tcatacgcta tttatttgct     960
tggtactgtt tcttttgtcg atgctcaccc tgttgtttgg tgttacttct gcag          1014

<210> SEQ ID NO 18
<211> LENGTH: 450
<212> TYPE: DNA
<213> ORGANISM: Sorghum bicolor

<400> SEQUENCE: 18
gcatccatgg acgtggattg aattgaaggt gtactactgc tgtgctggtc cgtggatcgt      60
ggctgtcatg catggtttgc tgtgtcttct acgatatgta cttccctttg ttccgtatat     120
gtacatcttc ctcgtttggt tcatgtattt tcctttgaat aataataaat aaatcgggct     180
ttccatatcg gatgctttta tatctgtgtg tatggagatt gtggtatatg gtttcatctc     240
aagttgttta cgtcaagaac taaagatatt tcctcaaaaa aaaagaacta agatataat      300 caatgtcatt aacataactc atttccatga ggagaggacg aaggacgaag tcataataag     360
tagattggtt gatattttat aatcattcaa aactgcaggg gttataagat cttcattttg     420
tagaagtttt agatcttccg aggggttctc                                      450

<210> SEQ ID NO 19
<211> LENGTH: 43
<212> TYPE: PRT
<213> ORGANISM: Oryza sativa

<400> SEQUENCE: 19

Met Ser Arg Arg His His Leu His Leu Pro Leu Arg Leu Leu Ser Arg
1               5                   10                  15

Asn Asn Pro Ser Ala Pro Leu Phe Arg His Ala Phe Ser Thr Leu Asp
            20                  25                  30

Thr Pro Glu Pro Pro Pro Pro Glu Thr Glu Ala
        35                  40

<210> SEQ ID NO 20
<211> LENGTH: 66
<212> TYPE: PRT
<213> ORGANISM: Oryza sativa

<400> SEQUENCE: 20

Met Ala Thr Arg Arg Ala Leu Thr Ser Val Leu Arg Ser Ala Ser Arg
```

```
                1               5                   10                  15
Leu Arg Ala Ala Ser Pro Ser Pro Cys Pro Arg Arg Ala Pro Leu His
                20                  25                  30

Pro His Arg Arg Pro Ser Pro Ala Gly Phe Leu Leu Asn Arg Ala Ala
                35                  40                  45

Ala Ala Tyr Ala Ser Ser Ala Ala Ala Gln Ala Ala Pro Ala Pro Pro
                50                  55                  60

Pro Ala
65

<210> SEQ ID NO 21
<211> LENGTH: 829
<212> TYPE: PRT
<213> ORGANISM: artificial sequence
<220> FEATURE:
<223> OTHER INFORMATION: SR-256

<400> SEQUENCE: 21

Met Ser Arg Leu Arg Leu Pro Arg Gly Ser Ser Ser Thr Thr Leu
1               5                   10                  15

Ile Pro Arg Leu Arg Leu Leu Arg Arg Cys Ser Thr Phe Thr Ser Thr
                20                  25                  30

Ser Ser Pro Ser Arg Ser Trp Ser Pro Arg Asp Ala Phe Ala Ala Ala
                35                  40                  45

Thr Glu Arg Ile Arg Ala Gly Thr Leu Ser Pro Glu Asp Ala His Lys
                50                  55                  60

Leu Phe Asp Glu Leu Leu Gly Lys Ala Thr Pro Val Pro Glu Arg Ser
65                  70                  75                  80

Leu Asn Gly Phe Leu Ala Ala Leu Ala Arg Ala Pro Ala Ser Gly Asn
                85                  90                  95

Cys Ile Arg Asp Gly Pro Ala Leu Ala Val Ala Leu Phe Asn Arg Val
                100                 105                 110

Cys Arg Glu Glu Ala Gly Pro Gln Val Ala Ala Leu Thr Val Cys Thr
                115                 120                 125

Tyr Asn Ile Leu Met Asp Cys Cys Cys Arg Ala Arg Arg Pro Asp Ile
                130                 135                 140

Gly Leu Ala Val Phe Gly Arg Phe Leu Arg Lys Gly Leu Lys Thr Asp
145                 150                 155                 160

Gln Thr Gly Ala Asn Thr Phe Leu Lys Cys Leu Cys Tyr Ala Lys Arg
                165                 170                 175

Thr Asp Glu Ala Val Asn Val Leu Leu His Arg Met Ser Glu Leu Gly
                180                 185                 190

Cys Val Pro Asn Ala Ile Ser Tyr Asn Thr Val Leu Lys Gly Leu Cys
                195                 200                 205

Asp Asn Ser Met Ser Gln Arg Ala Leu Asp Leu Leu Gln Met Val Ala
                210                 215                 220

Arg Lys Gly Gly Gly Cys Phe Pro Asp Val Val Ala Tyr Ser Thr Val
225                 230                 235                 240

Ile His Gly Phe Phe Lys Glu Gly Glu Thr Gly Lys Ala Cys Ser Leu
                245                 250                 255

Phe His Glu Met Met Gln Gln Gly Ile Val Pro Ser Val Ala Thr Tyr
                260                 265                 270

Asn Ser Ile Ile Asp Ala Leu Cys Lys Val Arg Ala Val Asp Asn Ala
                275                 280                 285

Glu Leu Val Leu Arg Gln Met Val Ala Lys Gly Ala Gln Pro Asp Thr
```

```
                290                 295                 300
Val Thr Tyr Asn Cys Met Ile Asn Gly Tyr Ala Thr Ser Gly Arg Leu
305                 310                 315                 320

Lys Glu Ala Ala Lys Met Phe Arg Glu Met Lys Ser Arg Gly Leu Thr
                325                 330                 335

Pro Asn Val Val Thr Cys Asn Ser Phe Leu Ala Ser Leu Cys Lys His
                340                 345                 350

Gly Thr Ser Lys Glu Ala Ala Glu Phe Phe Asp Ser Met Thr Ala Lys
                355                 360                 365

Gly Gln Lys Pro Asp Ile Ile Ser Tyr Cys Thr Leu Leu Arg Gly Tyr
        370                 375                 380

Ala Ser Glu Gly Cys Phe Thr Asp Met Ile Asp Leu Phe Asn Ser Met
385                 390                 395                 400

Lys Ser Asn Gly Ile Ala Ala Asp Cys His Val Phe Thr Ile Leu Ile
                405                 410                 415

Asp Thr Tyr Ala Lys Arg Gly Met Met Asp Asp Ala Met His Ile Phe
                420                 425                 430

Thr Glu Met Arg Gln Gln Gly Val Ser Pro Asn Val Val Thr Tyr Ser
                435                 440                 445

Thr Val Ile Ser Thr Leu Ser Arg Met Gly Arg Leu Thr Asp Ala Met
        450                 455                 460

Glu Lys Phe Asn Gln Met Val Ala Leu Gly Val Gln Pro Asp Arg Ala
465                 470                 475                 480

Ile Tyr Asn Ser Leu Ile Gln Gly Phe Cys Met His Gly Gly Leu Val
                485                 490                 495

Lys Ala Lys Glu Leu Val Ser Gln Met Ile Asn Lys Gly Ile Pro His
                500                 505                 510

Pro Asn Ile Val Phe Phe Asn Ser Val Ile Asn Ser Met Cys Lys Glu
        515                 520                 525

Gly Arg Val Met Asp Ala His Asp Ile Leu Asp Leu Val Ile Asp Ile
530                 535                 540

Gly Asp Arg Pro Asn Asp Ile Ser Phe Asn Ser Leu Ile Asp Gly Tyr
545                 550                 555                 560

Cys Leu Val Gly Lys Met Asp Lys Ala Phe Gly Met Leu Asn Ala Met
                565                 570                 575

Glu Ser Val Gly Val Glu Pro Asp Ile Val Thr Tyr Asn Thr Leu Val
                580                 585                 590

Lys Gly Tyr Cys Arg Asn Gly Arg Ile Asp Asp Gly Leu Thr Leu Phe
        595                 600                 605

Arg Glu Met Leu Cys Lys Gly Val Lys Pro Asp Thr Val Thr Tyr Asn
610                 615                 620

Ile Val Leu Asn Gly Leu Phe His Ser Gly Arg Thr Val Ala Ala Arg
625                 630                 635                 640

Lys Met Phe His Gln Met Ile Glu Ser Gly Thr Thr Val Asn Ile Ser
                645                 650                 655

Thr Tyr Gly Ile Ile Leu Gly Gly Leu Cys Arg Asn Asn Cys Ala Asp
        660                 665                 670

Glu Ala Ile Ala Leu Phe Gln Lys Leu Gly Ala Met Asn Val Lys Phe
                675                 680                 685

Ser Ile Thr Ile Leu Asn Thr Met Ile Asn Ala Met Tyr Lys Val Gln
        690                 695                 700

Arg Lys Glu Glu Ala Lys Glu Leu Phe Gly Thr Ile Ser Ala Ser Gly
705                 710                 715                 720
```

```
Leu Val Pro Asn Glu Ser Thr Tyr Gly Val Met Ile Lys Asn Leu Leu
                725                 730                 735

Glu Glu Gly Ser Val Glu Ala Asp Asn Met Phe Ser Phe Met Asp
            740                 745                 750

Arg Ser Gly Ile Val Pro Asp Ser Arg Leu Met Asn Asp Ile Ile Arg
        755                 760                 765

Met Leu Leu Glu Lys Gly Glu Ile Ala Lys Ala Gly Tyr Tyr Leu Ser
    770                 775                 780

Lys Val Asp Gly Lys Ser Ile Ser Leu Glu Ala Ser Thr Thr Ser Leu
785                 790                 795                 800

Met Phe Ser Leu Phe Ser Arg Lys Gly Thr Tyr Lys Glu Asp Met Lys
                805                 810                 815

Leu Leu Pro Ala Lys Tyr Gln Phe Phe Gly Gly Val Gly
                820                 825

<210> SEQ ID NO 22
<211> LENGTH: 813
<212> TYPE: PRT
<213> ORGANISM: artificial sequence
<220> FEATURE:
<223> OTHER INFORMATION: SR-279

<400> SEQUENCE: 22

Met Ser Gly Val Cys Leu Arg Arg Arg Leu Ser Ser Thr Ser Thr Ser
1               5                   10                  15

Asn Thr Pro Pro Ser Pro Ser Trp Ser Pro Gln Ala Ala Phe Ala Ala
                20                  25                  30

Ala Thr Glu Arg Ala Arg Ala Gly Thr Leu Ser Pro Gln Asp Ala His
            35                  40                  45

His Leu Phe Asp Glu Leu Phe Arg Gln Ala Thr Pro Val Pro Glu Arg
    50                  55                  60

Ser Leu Glu Gly Phe Leu Ala Ala Leu Gly Arg Ala Ala Ser Ser Glu
65                  70                  75                  80

Ala Cys Arg Asp Gly Pro Ser Leu Ala Leu Thr Leu Phe Asn Arg Leu
                85                  90                  95

Cys Arg Glu Glu Ala Gly Arg Arg Val Ala Pro Pro Thr Ile Tyr Thr
            100                 105                 110

Tyr Asn Ile Leu Met Asn Cys Cys Cys Arg Val Arg Arg Pro Asp Leu
    115                 120                 125

Gly Leu Ala Phe Phe Gly Arg Leu Leu Arg Thr Gly Leu Lys Thr Asn
130                 135                 140

Glu Val Val Ala Ser Thr Leu Leu Lys Cys Leu Cys Cys Ala Lys Arg
145                 150                 155                 160

Ala Asp Glu Ala Val Asn Val Leu Leu His Arg Met Ser Val Leu Gly
                165                 170                 175

Cys Val Pro Asn Ser Phe Ser Tyr Asn Ile Val Leu Lys Ser Leu Cys
            180                 185                 190

Asp Asp Ser Arg Ser Gln Arg Ala Leu Gly Leu Leu Gln Met Met Ala
    195                 200                 205

Lys Gly Gly Val Cys Ser Pro Asn Val Leu Ser Tyr Asn Thr Val Ile
210                 215                 220

His Gly Phe Phe Lys Glu Gly Glu Ile Asp Lys Ala Cys Asn Leu Phe
225                 230                 235                 240

His Glu Met Thr Lys Gln Gly Phe Val Pro Asn Val Val Thr Tyr Asn
                245                 250                 255
```

```
Ser Val Ile Asn Ala Leu Cys Lys Ala Arg Ala Met Asp Asn Ala Glu
            260                 265                 270

Ser Phe Leu Arg Gln Met Val Asp Asn Gly Val Pro Pro Asp Lys Val
            275                 280                 285

Thr Tyr Thr Ser Ile Ile His Gly Tyr Ser Thr Leu Gly Arg Trp Lys
        290                 295                 300

Glu Ala Thr Lys Met Phe Arg Glu Met Thr Ser Arg Gly Leu Ile Pro
305                 310                 315                 320

Asp Ile Val Thr Arg Asn Ser Phe Met Asp Ser Leu Cys Lys His Gly
                325                 330                 335

Arg Ser Lys Glu Ala Ala Glu Ile Phe Phe Ser Met Ala Ala Arg Gly
            340                 345                 350

His Lys Pro Asp Ile Val Ser Tyr Thr Ile Leu Leu His Gly Tyr Gly
        355                 360                 365

Asn Glu Gly Ser Phe Ser Asp Met Met Ser Leu Phe Asn Ser Met Glu
    370                 375                 380

Gly Gly Gly Ile Val Ala Asp Cys Gln Val Phe Asn Ile Leu Ile Asp
385                 390                 395                 400

Ala Tyr Ala Lys Arg Gly Met Ile Asp Glu Ala Met Leu Ile Phe Thr
                405                 410                 415

Glu Met Leu Gly Gln Gly Val Asn Pro Ser Val Val Thr Tyr Ser Thr
            420                 425                 430

Leu Ile Ala Ala Leu Cys Arg Thr Gly Arg Leu Ala Asp Ala Met Asp
        435                 440                 445

Lys Phe Ser Gln Met Val Gly Thr Gly Val Gln Pro Asn Thr Val Val
    450                 455                 460

Tyr His Ser Leu Ile Gln Gly Phe Cys Thr His Gly Asp Leu Val Lys
465                 470                 475                 480

Ala Lys Glu Leu Ile Ser Glu Met Met Asn Lys Gly Ile Ile Cys Pro
                485                 490                 495

Asn Ile Ala Phe Phe Asn Ser Ile Val Asp Ser Leu Cys Lys Glu Gly
            500                 505                 510

Arg Val Met Asp Ala His His Ile Phe Asp Leu Val Lys Asp Ile Gly
        515                 520                 525

Glu Lys Pro Asp Ala Ile Met Phe Asn Thr Leu Ile Asp Gly Tyr Cys
    530                 535                 540

Leu Val Gly Glu Met Gly Lys Ala Phe Met Val Leu Asp Val Met Thr
545                 550                 555                 560

Ser Ala Gly Ile Glu Pro Asp Ala Ile Thr Tyr Ser Thr Leu Val Ser
                565                 570                 575

Gly Tyr Cys Lys Ser Gly Arg Ile Asp Asp Gly Leu Ile Leu Phe Arg
            580                 585                 590

Glu Glu Met Leu His Lys Lys Val Lys Pro Thr Ile Val Thr Tyr Asn
        595                 600                 605

Ile Ile Leu Glu Gly Leu Phe Arg Ala Gly Arg Thr Val Ala Ala Lys
    610                 615                 620

Lys Met Leu His Glu Ile Ile Gly Ser Gly Thr Pro Val Asp Met His
625                 630                 635                 640

Thr Tyr Asn Ile Phe Leu Arg Gly Leu Cys Arg Asn Cys Ala Asp
                645                 650                 655

Glu Ala Ile Val Leu Phe Gln Lys Ser Arg Ala Met Asn Val Lys Phe
            660                 665                 670
```

Asn Ile Thr Thr Leu Asn Thr Met Ile Asn Ala Phe Tyr Lys Gly Asp
              675                 680                 685

Arg Arg Glu Glu Ala Asn Asp Leu Phe Ala Ala Leu Pro Ala Ser Gly
    690                 695                 700

Leu Val Pro Asp Ala Ser Thr Tyr Gly Val Met Ile Gln Asn Leu Leu
705                 710                 715                 720

Lys Glu Gly Ala Val Glu Ala Asp Asn Met Phe Ser Ser Met Glu
                725                 730                 735

Lys Ser Gly Cys Ala Pro Ser Ser Arg Leu Val Asn Asp Val Ile Arg
                740                 745                 750

Thr Leu Leu Glu Lys Gly Glu Ile Val Lys Ala Gly Lys Tyr Met Ser
            755                 760                 765

Lys Val Tyr Gly Lys Ser Leu Ser Leu Asp Ala Ser Thr Ser Ser Leu
    770                 775                 780

Leu Leu Ser Leu Phe Ser Gly Asn Gly Lys Tyr Arg Glu Gln Ile Gln
785                 790                 795                 800

Leu Leu Pro Ala Lys Tyr Gln Phe Phe Gly Gly Ile Ser
                805                 810

<210> SEQ ID NO 23
<211> LENGTH: 5010
<212> TYPE: DNA
<213> ORGANISM: artificial sequence
<220> FEATURE:
<223> OTHER INFORMATION: proZmUBI_intZmUBI_SR_256_terSbHSP

<400> SEQUENCE: 23

| | | | | | |
|---|---|---|---|---|---|
| gtgcagcgtg | acccggtcgt | gccctctct | agagataatg | agcattgcat | gtctaagtta | 60 |
| taaaaaatta | ccacatattt | tttttgtcac | acttgtttga | agtgcagttt | atctatcttt | 120 |
| atacatatat | ttaaactttta | ctctacgaat | aatataatct | atagtactac | aataaatca | 180 |
| gtgttttaga | gaatcatata | aatgaacagt | tagacatggt | ctaaaggaca | attgagtatt | 240 |
| ttgacaacag | gactctacag | ttttatcttt | ttagtgtgca | tgtgttctcc | tttttttttg | 300 |
| caaatagctt | cacctatata | atacttcatc | cattttatta | gtacatccat | ttagggttta | 360 |
| gggttaatgg | ttttttataga | ctaatttttt | tagtacatct | attttattct | attttagcct | 420 |
| ctaaattaag | aaaactaaaa | ctctatttta | gttttttat | ttaataattt | agatataaaa | 480 |
| tagaataaaa | taaagtgact | aaaaattaaa | caaatacct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggaccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattcctttc | ccaccgctcc | 840 |
| ttcgctttcc | cttcctcgcc | cgccgtaata | aatagacacc | cctccacac | cctctttccc | 900 |
| caacctcgtg | ttgttcggag | cgcacacaca | cacaaccaga | tctcccccaa | atccacccgt | 960 |
| cggcacctcc | gcttcaaggt | acgccgctcg | tcctccccc | ccccccctct | ctaccttctc | 1020 |
| tagatcggcg | ttccggtcca | tggttagggc | ccggtagttc | tacttctgtt | catgtttgtg | 1080 |
| ttagatccgt | gtttgtgtta | gatccgtgct | gctagcgttc | gtacacggat | gcgacctgta | 1140 |
| cgtcagacac | gttctgattg | ctaacttgcc | agtgtttctc | tttggggaat | cctgggatgg | 1200 |
| ctctagccgt | tccgcagacg | ggatcgattt | catgattttt | tttgtttcgt | tgcatagggt | 1260 |

```
ttggtttgcc cttttcctttt atttcaatat atgccgtgca cttgtttgtc gggtcatctt   1320
ttcatgcttt tttttgtctt ggttgtgatg atgtggtctg gttgggcggt cgttctagat   1380
cggagtagaa ttaattctgt ttcaaactac ctggtggatt tattaattt ggatctgtat   1440 gtgtgtgcca tacatattca tagttacgaa ttgaagatga tggatggaaa tatcgatcta   1500
ggataggtat acatgttgat gcgggtttta ctgatgcata tacagagatg cttttgttc   1560 gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg   1740
ttgatgtggg ttttactgat gcatatacat gatggcatat gcagcatcta ttcatatgct   1800
ctaaccttga gtacctatct attataataa acaagtatgt tttataatta ttttgatctt   1860
gatatacttg gatgatggca tatgcagcag ctatatgtgg attttttag ccctgccttc   1920 atacgctatt tatttgcttg gtactgtttc ttttgtcgat gctcaccctg ttgtttggtg   1980
ttacttctgc aggtctccac catgtctcgc ctccgcctcc cccgcggcag ctcctcctcc   2040
accacgctga tccccgcct ccggctcctc cgccgctgct ccaccttcac ctccacctcg   2100
tcgccctcac gctcctggtc tccccagac gcctttgccg cggccacgga gcgtattcgc   2160
gccgggacgc tcagcccgga agacgctcac aaactgttcg acgaattgct cggtaaggcc   2220
accccggtcc cggagcgctc cctgaacgga ttccttgccg ccctcgcccg tgcgcccgcc   2280
tccggcaact gcatcagaga tggccccgcc ctcgcagtgg ctctcttcaa ccgtgtgtgc   2340
agagaggaag ccgcccgca ggtggcggcg ctcacagttt gcacctacaa catcctcatg   2400
gactgctgct gccgtgcgcg tcgtccggac atagggcttg ccgtatttgg ccgcttcctc   2460
aggaagggcc tgaagacaga ccagaccggc gccaacacct tcctcaagtg cctctgctac   2520
gcgaaacgga cggatgaggc tgtgaacgtg ctgctccaca ggatgtccga gctcggctgt   2580
gtgcctaatg ccatttcgta caacactgtt ctgaagggct tatgcgacaa tagcatgagt   2640
cagcgggcgc tcgacctgct ccagatggtg gcgagaaaag gaggtggctg cttccctgat   2700
gtggtggcgt atagcacggt catccatggc ttttttaagg agggtgaaac agggaaggca   2760
tgcagtctat tccatgaaat gatgcaacaa gggattgtgc ccagtgtggc gacatataac   2820
tcgattattg atgcgttgtg caaggtcaga gcagtggaca atgcagagct agtccttcgt   2880
cagatggttg ctaaaggtgc tcaacccgat acagtgacat ataattgcat gatcaatgga   2940
tatgccacat ctgggcggtt gaaagaggct gctaaaatgt tcagagaaat gaaaagccgg   3000
ggtcttacac caaatgttgt tacttgcaac tcgttcctgg cctccctttg caagcacgga   3060
acaagcaaag aagctgcaga atttttgat tctatgacag ccaagggcca aaaacctgat   3120
atcatctcgt actgtacttt gcttcgtggg tatgccagtg aaggatgctt tactgatatg   3180
attgatctct ttaattcaat gaaaagcaat ggtattgcag ctgactgcca tgttttcacc   3240
atattaattg ataccatgc taaacgcgga atgatggatg atgcaatgca catatttacg   3300
gaaatgcggc aacaaggtgt gagtccaaat gttgtcacat attcaactgt aatatcaaca   3360
ctttctagaa tgggtaggtt gaccgatgct atggaaaaat ttaatcagat ggttgccttg   3420
ggagtacagc cagatagagc tatttataac tccctaattc agggattttg tatgcatggt   3480
ggtttggtta aagctaagga gttggttct caaatgataa acaaaggtat tcctcatcct   3540
aacattgtgt tcttcaattc agtaataaac agtatgtgca aggaaggcag ggttatggat   3600
gcacatgata tccttgactt ggttatagac ataggtgata ggcctaatga catttcattt   3660
```

```
aattcactga ttgatggata ttgcttagtc gggaagatgg ataaagcatt cggaatgctt    3720
aatgccatgg aatcagttgg tgttgagcct gatattgtta cttacaatac acttgttaag    3780
ggctattgta gaaatggaag gatcgatgat ggtttaactc tgtttagaga aatgttgtgc    3840
aagggagtta aacctgacac tgtgacatat aacatcgtac tgaatgggtt gtttcattct    3900
gggagaactg ttgctgcaag gaaaatgttc catcagatga ttgaaagtgg aacaacagtg    3960
aacatttcca catacggtat aatacttgga ggtctttgta gaaataattg tgcagacgaa    4020
gcgattgccc tgttccagaa attaggagca atgaatgtaa agttcagtat tacaatactc    4080
aataccatga ttaatgcaat gtacaaggtt caaagaaaag aagaagctaa ggagttgttc    4140
ggtacaatat cagccagtgg gttggtgcct aatgaatcta cttatggagt aatgataaaa    4200
aatcttctcg aagaaggatc agtggaagaa gctgacaata tgttttcgtt tatggacagg    4260
agtggtatag tccccgactc ccgtctcatg aatgatatca tcagaatgtt gttggaaaaa    4320
ggtgagatcg ccaaggccgg atattatctg tctaaagttg atggcaagag catatcactt    4380
gaagcttcaa ctacttcatt gatgtttcct ctcttctcaa ggaaaggcac atataaggag    4440
gacatgaaat tgctccctgc aaagtatcaa ttttccggtg gagttggtga ttacaaggat    4500
cacgacgggg actacaaaga ccatgatatt gactacaaag acgatgacga caaatgaaac    4560
gcatccatgg acgtggattg aattgaaggt gtactactgc tgtgctggtc cgtggatcgt    4620
ggctgtcatg catggtttgc tgtgtcttct acgatatgta cttccctttg ttccgtatat    4680
gtacatcttc ctcgtttggt tcatgtattt tcctttgaat aataataaat aaatcgggct    4740
ttccatatcg gatgctttta tatctgtgtg tatggagatt gtggtatatg gtttcatctc    4800
aagttgttta cgtcaagaac taaagatatt tcctcaaaaa aaaagaacta agatataat    4860 caatgtcatt aacataactc atttccatga ggagaggacg aaggacgaag tcataataag    4920
tagattggtt gatattttat aatcattcaa aactgcaggg gttataagat cttcattttg    4980
tagaagtttt agatcttccg aggggttctc                                     5010
```

<210> SEQ ID NO 24
<211> LENGTH: 4962
<212> TYPE: DNA
<213> ORGANISM: artificial sequence
<220> FEATURE:
<223> OTHER INFORMATION: proZmUBI_intZmUBI_SR_279_terSbHSP

<400> SEQUENCE: 24

```
gtgcagcgtg acccggtcgt gcccctctct agagataatg agcattgcat gtctaagtta     60
taaaaaatta ccacatattt ttttgtcac acttgtttga agtgcagttt atctatcttt     120
atacatatat ttaaactta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg    300 caaatagctt cacctatata atacttcatc catttttatta gtacatccat ttagggttta   360
gggttaatgg ttttttataga ctaattttttt tagtacatct attttattct attttagcct   420
ctaaattaag aaaactaaaa ctctatttta gttttttttat ttaataattt agatataaaa   480
tagaataaaa taaagtgact aaaaattaaa caaataccct ttaagaaatt aaaaaaacta   540
aggaaacatt ttcttgtttt cgagtagata atgccagcct gttaaacgcc gtcgacgagt   600
ctaacggaca ccaaccagcg aaccagcagc gtcgcgtcgg gccaagcgaa gcagacggca   660
```

```
cggcatctct gtcgctgcct ctggaccect ctcgagagtt ccgctccacc gttggacttg      720
ctccgctgtc ggcatccaga aattgcgtgg cggagcggca gacgtgagcc ggcacggcag      780
gcggcctcct cctcctctca cggcaccggc agctacgggg gattcctttc ccaccgctcc     840
ttcgctttcc cttcctcgcc cgccgtaata aatagacacc cctccacac cctctttccc      900 caacctcgtg ttgttcggag cgcacacaca cacaaccaga tctcccccaa atccacccgt    960
cggcacctcc gcttcaaggt acgccgctcg tcctccccec cccccctct ctaccttctc     1020 tagatcggcg ttccggtcca tggttagggc ccggtagttc tacttctgtt catgtttgtg   1080
ttagatccgt gttttgtgtta gatccgtgct gctagcgttc gtacacggat gcgacctgta   1140
cgtcagacac gttctgattg ctaacttgcc agtgtttctc tttggggaat cctgggatgg    1200
ctctagccgt tccgcagacg ggatcgattt catgatttt tttgtttcgt tgcatagggt    1260
ttggtttgcc ctttttccttt atttcaatat atgccgtgca cttgtttgtc gggtcatctt   1320
ttcatgcttt tttttgtctt ggttgtgatg atgtggtctg gttgggcggt cgttctagat   1380
cggagtagaa ttaattctgt ttcaaactac ctggtggatt tattaatttt ggatctgtat    1440
gtgtgtgcca tacatattca tagttacgaa ttgaagatga tggatggaaa tatcgatcta   1500
ggataggtat acatgttgat gcgggtttta ctgatgcata tacagagatg ctttttgttc   1560
gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg    1740
ttgatgtggg ttttactgat gcatatacat gatggcatat gcagcatcta ttcatatgct   1800
ctaaccttga gtacctatct attataataa acaagtatgt tttataatta ttttgatctt    1860
gatatacttg gatgatggca tatgcagcag ctatatgtgg attttttag ccctgccttc    1920 atacgctatt tatttgcttg gtactgtttc ttttgtcgat gctcaccctg ttgtttggtg   1980
ttacttctgc aggtctccac catgtccggc gtctgcctcc gccgccgcct ctcctccacc   2040
tccacctcca acacgccacc ctcaccttcc tggtcacccc aggccgcctt tgccgcggcc   2100
acggagcgcg cccgcgccgg aacgctcagc cctcaagacg cacaccacct gttcgacgaa   2160
ttgtttcggc aggccactcc ggttcccgag cgctcccttg aaggattcct tgccgccctc   2220
ggccgtgctg catcctctga agcctgcaga gacggcccct cccttgccct cactctcttc    2280
aaccgtctct gccgagaaga agccggccgg cgggtggcgc cgcccacaat ctacacctac   2340
aatatcctga tgaactgctg ctgccgcgtg cgtcgtccag acctagggct cgccttcttc   2400
ggccgcctcc taaggaccgg cctcaaaaca aatgaggtcg tcgccagcac cctcctcaag   2460
tgcctctgct gtgcaaaacg ggcagatgaa gctgtgaacg tgctgcttca taggatgtcc    2520
gtcctcggct gtgtgcctaa ttccttctca tacaacatag ttctaaagag cttatgtgat   2580
gacagcagga gccagcgagc gctcggcctg ctccagatga tggcaaaagg aggtgtctgc   2640
tcccccaacg ttctgtcata taacacagtc atccacggct tctttaagga aggtgaaata   2700
gacaaggcct gcaatctatt ccatgaaatg acgaagcaag ggtttgtgcc taatgtggtg   2760
acatataact cggttatcaa tgcattgtgc aaggcccgag caatggacaa tgcagagtcg   2820
ttccttcggc agatggttga taacggtgtt ccacctgata aggtgacata tactagcatc   2880
atccatggat attccacttt gggccgatgg aaagaggcaa ctaaaatgtt cagagaaatg   2940
acaagcaggg gtcttatacc agatattgtc actcggaact cattcatgga ctcactctgc    3000
aagcatggaa gaagcaaaga agctgcagaa attttcttt ccatggctgc aaggggccac    3060
```

-continued

```
aagcctgata tcgtctccta cactattctt ctccatgggt atggcaatga aggaagcttt    3120
tctgatatga tgagtctctt taattcaatg aaggcggcg gtattgtggc cgattgccaa    3180
gttttcaaca tattaattga tgcatatgct aaacgaggaa tgatcgacga agctatgctc   3240
atatttactg aaatgctagg acaaggagtc aatccgagtg tagtcaccta ctcaactctg   3300
atagctgcac tttgcagaac aggtaggcta gctgatgcta tggataagtt tagtcagatg   3360
gttggtacgg gagtacaacc gaacacagtt gtttatcact ccctaattca gggtttctgt   3420
acacatggcg atttggtcaa agcgaaggaa ttgatttctg aaatgatgaa taaaggtatt   3480
atttgtccaa acattgcatt cttcaattca atagtagaca gtctatgcaa agaaggaagg   3540
gttatggatg cacaccatat ctttgacttg gttaaagaca taggtgagaa acctgatgcc   3600
atcatgttta tacgctaat tgacggatat tgcttagttg gtgagatggg caaagcattc   3660
atggtacttg atgtcatgac atcagctggc attgagcctg atgccattac gtatagtaca   3720
cttgtcagtg atattgtaa aagtggaagg atcgatgatg ggttgattct gttcagagaa   3780
gaaatgttgc ataagaaagt taaaccaaca attgttacat ataacatcat attggagggg   3840
ttatttcgtg ctgggagaac agttgctgca aagaaaatgc tccatgaaat tatcggaagt   3900
gggacacctg tggacatgca tacatacaac atatttctta gaggactttg tagaaataat   3960
tgcgcggatg aagcgatcgt cctattccag aaatcacgtg caatgaatgt gaagttcaat   4020
atcacaacac tcaataccat gattaatgca ttctacaagg gtgacagaag agaagaagct   4080
aatgatttgt ttgctgcatt accagccagc gggttggtgc ctgatgcttc cacttacgga   4140
gtaatgatac aaaaccttct aaaagaagga gcagtggagg aagctgacaa tatgttctca   4200
tcaatggaga agagtggttg tgctcctagc tctcgtcttg tgaatgatgt catcagaact   4260
ttattggaaa aggggagat agtcaaggcc ggaaaatata tgtctaaagt ttatggcaag   4320
agcctatcac ttgatgcttc aactagttcg ttgttgttgt ctctcttttc agggaatggg   4380
aaatatcggg aacaaataca attgctccct gcaaagtacc agttttttcgg tggaatcagt   4440
gattacaagg atcacgacgg ggactacaaa gaccatgata ttgactacaa agacgatgac   4500
gacaaatgaa acgcatccat ggacgtggat tgaattgaag gtgtactact gctgtgctgg   4560
tccgtggatc gtggctgtca tgcatggttt gctgtgtctt ctacgatatg tacttccctt   4620
tgttccgtat atgtacatct tcctcgtttg gttcatgtat tttcctttga ataataataa   4680
ataaatcggg ctttccatat cggatgcttt tatatctgtg tgtatggaga ttgtggtata   4740
tggtttcatc tcaagttgtt tacgtcaaga actaaagata tttcctcaaa aaaaagaac   4800
taaagatata atcaatgtca ttaacataac tcatttccat gaggagagga cgaaggacga   4860
agtcataata agtagattgg ttgatatttt ataatcattc aaaactgcag gggttataag   4920
atcttcattt tgtagaagtt ttagatcttc cgagggttc tc                       4962
```

<210> SEQ ID NO 25
<211> LENGTH: 788
<212> TYPE: PRT
<213> ORGANISM: Triticum aestivum

<400> SEQUENCE: 25

Met Pro Arg Phe Ser Ser Thr Thr Pro Met Ser Pro Arg Leu Arg
1               5                   10                  15

Leu Arg Leu Cys Ala Arg His Ser Ser Thr Ser His Pro Ser Arg
            20                  25                  30

```
Ile Trp Asp Pro His Ala Ala Phe Ala Ala Ala Gln Arg Ala Ser
         35                  40                  45

Ser Gly Thr Leu Thr Thr Glu Asp Ala His His Leu Phe Asp Glu Leu
 50                  55                  60

Leu Arg Arg Gly Asn Pro Val Gln Glu Arg Pro Leu Asn Lys Phe Leu
 65                  70                  75                  80

Ala Ala Leu Ala Arg Ala Pro Ala Ser Ala Ser Cys Cys Asp Gly Pro
                 85                  90                  95

Ala Leu Ala Val Ala Leu Phe Gly Leu Ser Arg Asp Val Gly Arg
             100                 105                 110

Arg Val Ala Gln Pro Asn Val Phe Thr Tyr Gly Val Leu Met Asp Cys
             115                 120                 125

Cys Cys Arg Ala Cys Arg Thr Asp Leu Val Leu Ala Phe Phe Gly Arg
     130                 135                 140

Leu Leu Lys Thr Gly Leu Glu Ala Asn Gln Val Val Phe Asn Thr Leu
 145                 150                 155                 160

Leu Lys Gly Leu Cys His Thr Lys Arg Ala Asp Glu Ala Leu Asp Val
                 165                 170                 175

Leu Leu His Arg Met Pro Glu Leu Gly Cys Thr Pro Asn Val Val Ala
             180                 185                 190

Tyr Asn Thr Val Ile His Gly Phe Lys Glu Gly His Val Ser Lys
             195                 200                 205

Ala Cys Asn Leu Phe His Glu Met Ala Gln Gln Gly Val Lys Pro Asn
     210                 215                 220

Val Val Thr Tyr Asn Ser Val Ile Asp Ala Leu Cys Lys Ala Arg Ala
 225                 230                 235                 240

Met Asp Lys Ala Glu Val Val Leu Arg Gln Met Ile Asp Asp Gly Val
                 245                 250                 255

Gly Pro Asp Asn Val Thr Tyr Ser Ser Leu Ile His Gly Tyr Ser Ser
             260                 265                 270

Ser Gly His Trp Lys Glu Ala Val Arg Val Phe Lys Glu Met Thr Ser
     275                 280                 285

Arg Arg Val Thr Ala Asp Val His Thr Tyr Asn Met Phe Met Thr Phe
 290                 295                 300

Leu Cys Lys His Gly Arg Ser Lys Glu Ala Gly Ile Phe Asp Thr
 305                 310                 315                 320

Met Ala Ile Lys Gly Leu Lys Pro Asp Asn Val Ser Tyr Ala Ile Leu
                 325                 330                 335

Leu His Gly Tyr Ala Ala Glu Gly Cys Leu Val Asp Met Ile Asn Leu
             340                 345                 350

Phe Asn Ser Met Glu Arg Asp Cys Ile Leu Pro Asp Cys Arg Ile Phe
             355                 360                 365

Asn Ile Leu Ile Asn Ala Tyr Ala Lys Ser Gly Lys Leu Asp Lys Ala
 370                 375                 380

Met Leu Ile Phe Asn Glu Met Gln Lys Gln Gly Val Ser Pro Asn Ala
 385                 390                 395                 400

Val Thr Tyr Ser Thr Val Ile His Ala Phe Cys Lys Lys Gly Arg Leu
                 405                 410                 415

Asp Asp Ala Val Ile Lys Phe Asn Gln Met Ile Asp Thr Gly Val Arg
             420                 425                 430

Pro Asp Ala Ser Val Tyr Arg Pro Leu Ile Gln Gly Phe Cys Thr His
             435                 440                 445

Gly Asp Leu Val Lys Ala Lys Glu Tyr Val Thr Glu Met Met Lys Lys
```

```
        450                 455                 460
Gly Met Pro Pro Asp Ile Met Phe Phe Ser Ser Ile Met Gln Asn
465                 470                 475                 480

Leu Cys Thr Glu Gly Arg Val Thr Glu Ala Arg Asp Ile Leu Asp Leu
                485                 490                 495

Ile Val His Ile Gly Met Arg Pro Asn Val Ile Phe Asn Leu Leu
            500                 505                 510

Ile Gly Gly Tyr Cys Leu Val Arg Lys Met Ala Asp Ala Leu Lys Val
            515                 520                 525

Phe Asp Asp Met Val Ser Tyr Gly Leu Glu Pro Cys Asn Phe Thr Tyr
530                 535                 540

Gly Ile Leu Ile Asn Gly Tyr Cys Lys Asn Arg Ile Asp Asp Gly
545                 550                 555                 560

Leu Ile Leu Phe Lys Glu Met Leu His Lys Gly Leu Lys Pro Thr Thr
                565                 570                 575

Phe Asn Tyr Asn Val Ile Leu Asp Gly Leu Phe Leu Ala Gly Gln Thr
                580                 585                 590

Val Ala Ala Lys Glu Lys Phe Asp Glu Met Val Glu Ser Gly Val Ser
                595                 600                 605

Val Cys Ile Asp Thr Tyr Ser Ile Ile Leu Gly Gly Leu Cys Arg Asn
610                 615                 620

Ser Cys Ser Ser Glu Ala Ile Thr Leu Phe Arg Lys Leu Ser Ala Met
625                 630                 635                 640

Asn Val Lys Phe Asp Ile Thr Ile Val Asn Ile Ile Gly Ala Leu
                645                 650                 655

Tyr Arg Val Glu Arg Asn Gln Glu Ala Lys Asp Leu Phe Ala Ala Met
                660                 665                 670

Pro Ala Asn Gly Leu Val Pro Asn Ala Val Thr Tyr Thr Val Met Met
                675                 680                 685

Thr Asn Leu Ile Lys Glu Gly Ser Val Glu Glu Ala Asp Asn Leu Phe
            690                 695                 700

Leu Ser Met Glu Lys Ser Gly Cys Thr Ala Asn Ser Cys Leu Leu Asn
705                 710                 715                 720

His Ile Ile Arg Arg Leu Leu Glu Lys Gly Glu Ile Val Lys Ala Gly
                725                 730                 735

Asn Tyr Met Ser Lys Val Asp Ala Lys Ser Tyr Ser Leu Glu Ala Lys
                740                 745                 750

Thr Val Ser Leu Leu Ile Ser Leu Phe Ser Arg Lys Gly Lys Tyr Arg
                755                 760                 765

Glu His Ile Lys Leu Leu Pro Thr Lys Tyr Gln Phe Leu Glu Glu Ala
            770                 775                 780

Ala Thr Val Glu
785

<210> SEQ ID NO 26
<211> LENGTH: 2178
<212> TYPE: DNA
<213> ORGANISM: Triticum aestivum

<400> SEQUENCE: 26
gtaggatgtg tgcggggtga ttggaagatc aactataaa tattattgat actctcttaa   60
aagatgggat ggtgatcacc ttgcaataaa gagttatttt ttcgcgaata gcaataaaga  120
gttatttgat ggcaaaaaaa aatcagatga tgtgggctgg cctaggatat atagatatat  180
```

```
aacacttccc cttttatatt agaatactta aacatttcgt acattgcatg ttgttatata      240
gcctgcaaaa aaggctttcg cgctgcttta tataaaagc aacatagtca aactgatgta       300
tggtgatgag aagatcgtct tataaaacag atcatatgga aaaacaagaa acaatagag       360
tgcacaccct atcacaaaac aatctagact acaactaggg ggagacttgc accaagggaa     420
aacgcatgac ctcgttgcgc aactcgtacc aaggtgacac cagagagagc ccctaccctc      480
ccgctcctga tcgtggagcc taagcctgct tgcggacaac aaggatcgcg atggatgcca      540
ataagggctc gtgtaaaaag ataaggagga aaaacgacag cccacgcgcg aagccaagga      600
aacttcgatc cagcatccga acatgcctgc caattggcga cacggtgcac cgaaggtaac      660
ctaggcccca tgacgacgcc cacaggaggg agacgacgta aggagtcgcc atcgtcaaaa      720
ccgaagagac aatcaagggt tttcatccgg agccctggct ccaagagagg gaccacatcg      780
acggccccaa gagagatgcg acacccatgt gcatcactgc cactagtgtc gaagcacaag      840
gctttcgcct agagcctctt acaggcgtca catcgaggaa ccccgagcat cagcccaccc      900
gagggaagag atatcactac caaacaaggc ctccatggtt ctgggagccg tcactgccga      960
ggcaccaccg acaccgggat caccaagcgt ggcatccttt gccatccaca caaccaaaag    1020
atgtccccac caccgctgcc aaggcgcctg ctgaaaagcc gctctgacgg tccgccaccc    1080
taggccgccg ctccggcgtc aatatccca acctcgactc cacacgcggg caccaacccc     1140
cgaaaaccgc actcaccggt ggtgacacgg aaagcgaaac tactccatgc acgacgttca    1200
gtgaacgatc tctggacgac aaggaatcaa atggctggag ctgtactttg tctattcatg    1260
atcggtgtga tcaatagcgt cgtccacaga tcgggcaaag gccgtcgtcc gcataacatc    1320
gctccatgga aaggctcttc cttcccagtc ccacggcaca ccacgccgac accagcacca    1380
tctgcggcgg tgaccactga ccagcgaacc taactcggtc aaggagacca aacctggctg    1440
ggagcacgct accccatctg cctccacccc acagcacgag cacgggtgtc cattcaggta    1500
caacagggga tccacatcag aacatctcca acaatttgta tgttagtttg ttggtaaaat    1560
atgccatgtc atcaaccaac accgtaacat acaacaactt caatggatta tatctagcct    1620
gcccaataga atgtgagata taaataaggg tgctctctca ttctacattg gagcttgtgc    1680
aaggagtgtt gattcatgta catacaacct tcttctcttt cttcatttat tgtatgacac    1740
atcatcaaaa attctactac acccttccg atttataagg catgcacgta tccctaggtt    1800
tataatttga gcaatataaa ataagttgta tattctaaaa attacaccat tagaaagtag    1860
aaaatctgaa attttaata atatatttt tgtgacaaat agcttgtttt acgttggttt      1920
atttgtcaac ctagatatac gtgcaagccc tataaatcgg aaaggaggta gtatgtgaca    1980
aagtctacca agaaatatct tataactatt gagatgccct tagcgagagc tggctgccga    2040
ttgactgatg aatgaacaaa aatcctatat gacaaagtct accaagaact atttataac    2100
tattgccgat tgactgatga atgaaccgtt accgtcttct tgtacagaag taaacacttg    2160
tatacctcca ccgccccg                                                  2178

<210> SEQ ID NO 27
<211> LENGTH: 1716
<212> TYPE: DNA
<213> ORGANISM: Triticum aestivum

<400> SEQUENCE: 27
catatttcct tcactagctt ggtgcgaggc ttgcaacttt ctcctgtgat gctcatcaac       60
aaaatcggag ctgtcggtcc tcgacgcctg cggccgatcg tttggcttgg ctgtcgaggt     120
```

```
catcgggtgt cgtttgttca gagggg tctt gatgggtcgt cagcgaggaa accagagttg      180
cctgctcgca gagaggcgat gacgatgaca ttgcttgcag cctcgacggt gtcctctcct      240
cagcggtatg tgtgtggtct tgtcagtgcc aggtcggccg gagcgcccta ttcgatgggc      300
gtgttttaat taaccgagca actctcttct tcttaatcaa tgaaaatggc aagtctttta      360
ccttgtttca aaagagtta gatgcactgg aggtcctaaa ggtttcgtcg aggtgtcagt       420
ttagtcctat gtcttccaaa atgcgccttt aggtcctaat tctttcttaa gtggttcacc      480
cgaggtcctt ttccacgacc actcgctgac cagcccacgt gccgcattga cccacgccac      540
gtcgacagag gtccaaccg ccaggcgaga agcttcgcaa agagcacccc ccctcttag       600 tggcacccct ctcctctttc acggtacttt ggcgacattg gaggcgagtg gcagaggcaa      660
ccggaggtga tctggaggca atctgagtgg gtgcccgtga agatgcccct tctacgacgg     720
ccagtgagcg atcctcctcc atgttaccgt gagaaccca atcttgtcga tgctcttctc      780
ctgtagctct tctaatatgc cataactctg ccataatcaa tagttgtagt ccttgattta     840
ctttgatttg cataacggtg ctacggacac ggcaaaaagg acacaccacc ggcgacaaca     900
tacccgccga agttggagct tgcttcgccg cgccggtggc ggtgctgacg atgctgccat     960
gctcctcatc ttcagttgtt tccttgccga ggagcttgaa gttccggcca tggataggtt    1020
tagggcacac gagagagcag atttggggaa gaaataaagt cagggactgg ggaatgagaa    1080
ggtaatgttc ataagggggtt ttctgtaaaa agaaagagca acctaagcga ccccttttgtc    1140 gacttggcgt gggtcaatgc gccacacagg caggtcaatg agcgcttgtg agaaaaaggt    1200
cctcgggtaa accacttgct taaagaatta ctccctccgt cccatattat aagaacgttt    1260
ttgacactag tgtagtgtca aaacgttct tatattatgg gacggaggga gtagtaccta     1320
aaggtgcatt ttggactaaa taagactaaa gtgacaccca gacgaaactt ttaggacctc    1380
gagtgcatct aactcttaaa aaaacaaga tgctaaaaaa actaaatgct aaaaatata     1440 tttttctatg gaatactta aaaatactat tataattta tggcttccta gtatatttct      1500
agggcttaca actaaattta tattcttggt ctaaataaaa ttataatctg ataaattatg    1560
tgatatgaat atgtcatata ggcatatgag accataattt aattttacct gcaaaaaata    1620
agtaatagta gtagtactac tagataagat aacttggtaa agcactagcc ccgtcgtctc    1680
ccagttcagg atctacctac actgcacacc aaggcc                              1716

<210> SEQ ID NO 28
<211> LENGTH: 2500
<212> TYPE: DNA
<213> ORGANISM: Triticum aestivum

<400> SEQUENCE: 28
ggtggcggcc cccctttcct gcctttggtc attcgtctcc gcgcaggtcg gctgctctgg       60
ccggcccttg gtggttgctg tagtgctgcg gcaagggggt gccagatcca tcggttcttc     120
attcggatcc agctcgtctc ttgccttact cagggtcggt caccccgtga ccttgcctgc     180
ggcagtgagg gggtgtgcgt gctctgtgat gggccttgtg aggcgatggc gcgcttgctg     240 cgcagggggtg tgcgggccaa cttgtgtcgg ctgcgtgagg gtgttggttg agtctgctcc     300
aagcgcaagc ttgcccggct atggccggcc ggtggtggcg gcgcctacgg tgtcgtttc      360 ccttgttgaa ggcgttgttg tggagttctt cgacctacta caatctcgaa tctggttctt     420
cgggcgaaag ccttgcccca tctgggtcgg gcaacgacgt cgtccgtacg atgttttccc    480
```

```
ccttttggggc gttgctttga aggccggtta acctttcccg tgctaccttt gggttggtcg      540
tgcatggtgt catggttggc tggtgctcaa ccggtgatgc gagtggttgg cgttgcgact      600
cgtgcggcga cgaagatggt gatgtgcaga gctgggtcgc ggcttgtcct tctgatgtcg      660
gcggttcgat tcccctttgg gtgcatctgt gcttgtttct cactatgaca gagaagttga      720
agctgcatgc agcggggccc ttgcagcaat gatgactcca tgagggtggt tcggcagac      780 ggtgctctcc gtaggttgca ctggactagc ttggtgcgag gcttgcaact ttctcctgtg      840
atgctcatca acaaaatcgg agctgtcggt cctcgacgcc tgcggccgat catttggctt      900
ggctgtcgag gtcatcgggt gtcgtttgtt cagaggggtc ttgatgggtc gtcagcgagg      960
aaaccagagt tgcctgctcg cggagaggcg atgacgatga cattgcttgc agcctcgacg     1020
gtgtcctctc ctcagcggta tgtgtgtggt cttgtcagtg ccaggtcggc cggagcgtcc     1080
tattcgatgg gcgtgtttta attaaccgag caactctctt cttcttaatc aatgaaaatg     1140
gcaagtcttt tacctcgttt caaaaagagt tagatgcact ggaggtatcg agatgtcagt     1200
ttagtcctat gtcttccaaa atgcgccttt aggtcctaat tctttcttaa ttggttcacc     1260
cgaggtcctt ttccacgacc actcgctgac cagcccacgt gccgcattga cccacgccac     1320
gtcgacagag ggtccaaccg ccaggcgaga agcttcgcaa agagacaccc ccctcttag     1380 tggcacccct ctcctctttc acggtacttt ggcgacattg gaggcgagtg gcagaggcaa     1440
ccggaggtga tctggaggca atctgagtgg gtgcccgtga agatgcccct tctatgacgg     1500
ccagtgagcg gtcctcctcc atgttaccgt gagaacccta atcttgtcga tgctcttctc     1560
ctgtagctct tctattatgc cataactctg ccataatcaa tagttgtagt ccttgattta     1620
cttcgatttg cataacggtg ctacggacac ggcaaaaaag acacaccacc agcggcaaca     1680
tactcgccga agttggagct tgcttcgccg cgccggtggc ggtgctgacg atgctgccat     1740
gctcctcatc ttcagttgtt tccttgccga ggagcttgaa gttccggcca tggataggtt     1800
tagggcacac gagagagcag atttggggaa gaaataaagc cagggactgg ggaatgagaa     1860
ggtaatgttc ataaggggtt ttctgtaaaa agaaagagca acctaagcgg cccctttgtc     1920
gacttggcgt gggtcaatgc gccacatagg caggtcaatg agcgcttgtg agaaaaaggt     1980
cctcgggtaa accacttgct taagaattac tccctccgt cctataatat aagaacgttt     2040
ttgacactca ctagtgtagt gtcaaaaacg tttttatatt atgggacgga gggagtagta     2100
cctaaaggtg catttttggac taaataagac taaagtgaca ccccgacgaa acttttagga     2160
cctcgagtgc atttaactct taaaaaaaca aagatgctaa aaaaactaaa tgcttaaaaa     2220
tatatttttc tatgggaata cttaaaaata ctattataat tttatggctt cctagtatat     2280
ttctagggct tacaactaaa tttatattct tggtctaaat aaaattataa tctgataaat     2340
tatgtgatat gaatatgtca tatagccata tgagaccata atttaatttt acctgcaaaa     2400
aataagtaat agtagtagta ctactagata agataacttg gtaaagcact agccccgtcg     2460
tctcccagtt caggatctac ctacactgca caccaaggcc                             2500
```

<210> SEQ ID NO 29
<211> LENGTH: 4833
<212> TYPE: DNA
<213> ORGANISM: artificial sequence
<220> FEATURE:
<223> OTHER INFORMATION: proZmUBI_intZmUBI_TaRFL79_terSbHSP

<400> SEQUENCE: 29

```
gtgcagcgtg acccggtcgt gcccctctct agagataatg agcattgcat gtctaagtta      60
```

```
taaaaaatta ccacatattt tttttgtcac acttgtttga agtgcagttt atctatcttt      120
atacatatat ttaaacttta ctctacgaat aatataatct atagtactac aataatatca      180
gtgttttaga gaatcatata aatgaacagt tagacatggt ctaaaggaca attgagtatt      240
ttgacaacag gactctacag ttttatcttt ttagtgtgca tgtgttctcc tttttttttg      300
caaatagctt cacctatata atacttcatc cattttatta gtacatccat ttagggttta      360
gggttaatgg ttttttataga ctaattttttt tagtacatct attttattct attttagcct    420
ctaaattaag aaaactaaaa ctctatttta gttttttttat ttaataatttt agatataaaa    480 tagaataaaa taaagtgact aaaaattaaa caaatacccct ttaagaaatt aaaaaaacta    540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggaccccct ctcgagagtt ccgctccacc gttggacttg     720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca cacaaccaga tctcccccaa atccacccgt      960
cggcacctcc gcttcaaggt acgccgctcg tcctccccccc cccccctct ctaccttctc    1020 tagatcggcg ttccggtcca tggttagggc ccggtagttc tacttctgtt catgtttgtg     1080
ttagatccgt gtttgtgtta gatccgtgct gctagcgttc gtacacggat gcgacctgta     1140
cgtcagacac gttctgattg ctaacttgcc agtgtttctc tttggggaat cctgggatgg     1200
ctctagccgt tccgcagacg ggatcgattt catgattttt tttgtttcgt tgcatagggt     1260
ttggtttgcc ctttttcctttt atttcaatat atgccgtgca cttgtttgtc gggtcatctt   1320
ttcatgcttt tttttgtctt ggttgtgatg atgtggtctg gttgggcggt cgttctagat     1380
cggagtagaa ttaattctgt ttcaaactac ctggtggatt tattaatttt ggatctgtat     1440
gtgtgtgcca tacatattca tagttacgaa ttgaagatga tggatggaaa tatcgatcta     1500
ggataggtat acatgttgat gcgggttttta ctgatgcata tacagagatg cttttttgttc   1560 gcttggttgt gatgatgtgg tgtggttggg cggtcgttca ttcgttctag atcggagtag     1620
aatactgttt caaactacct ggtgtattta ttaattttgg aactgtatgt gtgtgtcata     1680
catcttcata gttacgagtt taagatggat ggaaatatcg atctaggata ggtatacatg     1740
ttgatgtggg ttttactgat gcatatacat gatggcatat gcagcatcta ttcatatgct    1800
ctaaccttga gtacctatct attataataa acaagtatgt tttataatta ttttgatctt     1860
gatatacttg gatgatggca tatgcagcag ctatatgtgg attttttttag ccctgccttc    1920 atacgctatt tatttgcttg gtactgtttc ttttgtcgat gctcaccctg ttgtttggtg     1980
ttacttctgc aggtctccac catgcctcgc ttctcctcca ccacgccaat gtcgccaccc     2040
cgcctcctcc tccggctcgg cgcccgccac tcctcctcca cctctcatcc ctcacgcatc    2100
tgggatcccc acgccgcctt cgccgctgcg acgcagcggg cgcgctctgg cacgctcacc    2160
acggaggacg cacaccacct gtttgatgaa ttgctgcggg agggcaatcc tgtccaggag    2220
cgtcccttga ctaactttct ggctgccctc gcccgcgcgc ccgcgtccgc attctgcagc    2280 gatgccctg ccctggccgt cgccctcttc ggccgtttgt cccgaggcgc cggacgacgg      2340
gtggcgcagc caaatgtctt cacctatggc gtcctcatgg actgctgctg ccgtgcgcgc    2400
```

```
cgcctggatc tagcgatcgc cttcttcgcc cgtctcctca agacgggact ggaggcaaac    2460
caagtcatct tctgcaccct cctcaaggga ctctgccacg caaagcgctc agatgaggct    2520
ttggacgtgg tgcttcacag gatgcctgag ctaggctgca cccccaacgt ggtggcctat    2580
accacggtca tccacggctt cttgaaggaa ggccaagtag gcaaggcatg caatctattc    2640
catggaatgg cgcagcaggg cgttgcgcct gatgtggtga catataactc ggttatcgat    2700
gcgttgtgca aggccagagc aatggacaag gcagagtatt ccttcgtga aatggttgat     2760 aatggtgtcg tacctaataa tgtgacatat aatagcctca tccatggata ttcctctttg    2820
ggccatcaga aggaggctgt tagggtgctg aaagaaatga caagacaggg tatcatacca    2880
gatgtcatta cctgcacctc actcatgacc ttcctttgca agaatggaaa aagcaaggaa    2940
gctgcagaaa ttttttgattc aatgccacg aagggcctga acatgacgc cgtttcatat     3000 gctattctcc ttcatgggta tgccactgaa ggatgcttgg ttgatatgat taatctcttc    3060
aattcgatgg acagagactg tattctacct aactgtcata tcttcaacat actgattta     3120 gcatatgcta aatctgggaa gcttgataag gctatgctta tatttagaga tatgcagaaa    3180
caaggagtga gcccagatgc attcacatat tcaaccttaa tacatgcatt ttgtaaaaag    3240
ggtcggttgg acgatgctat gataaagttt aatcagatgg ttgatacagg agtacgacag    3300
ggcacagctg tttatggttc tctaatccag ggtttttgta cacacggcga tttggtgaaa    3360
ggaaaggaat tggttactga aatgatgaac aaaggtatac ctcctcctga cattatgttc    3420
ttccattcaa tcatgcagaa cctatgcaca gaaggaaggg tagtagaagc acgggatatc    3480
cttggcttga tagcacacat aggtatgagg cctaatgttt gcacatttaa tatactgatt    3540
ggtggatact gcctagtccg caagatggag gatgcctcaa aaatatttca tgatatgatg    3600
tcatatggtt tagaaccttc taatgttacg tatggtattc ttattaatgg ctattgcaaa    3660
aacagaagga ttgatgacgg gctgattctg ttcaaagaaa tgttgcgcaa gggacttaaa    3720
cctacaactt ttaattacaa catcatactg gatggattat ttctggctgg acgaactgtt    3780
gctgcaaagg aaaagtttga tgagatggtt gaatctggag taagtatgtg catcagtact    3840
tactctatag ttcttcgtgg actttgtaga aataattgta gcggcgaagc catcacgcta    3900
ttccagacat taagcgcaat ggatgtgaaa ttcaatatta gaattgtcaa tatcatgatt    3960
gatgccttct tcagggttca gcgaaagcaa gaagctaagg attttgtttgc tgcaataaca   4020 gccaatgggt tggttgctaa tgttttttacc tacagcctaa tgatgacaaa tcttataaaa    4080
gaagggtcag tggaagaggc tgacacactc ttttttatcga tggagatgag cggctgtact    4140
tcgaactcgt ggatgttaaa tcttattatc agagggttgc tggaaaaagg agagatagtc    4200
aaggctggat gttatatgtc taaagttgat gccaagagct actcacttga agctaaaact    4260
gtttcgttgc tgatctatct cttttcaggg aaagggaaat acagagaaca cataagattg    4320
ctacctacaa agtatcagtt tctcgaagaa gcagccacag ttgaatggtt tgctatatag    4380
aacgcatcca tggacgtgga ttgaattgaa ggtgtactac tgctgtgctg gtccgtggat    4440
cgtggctgtc atgcatggtt tgctgtgtct tctacgatat gtacttccct tgttccgta    4500 tatgtacatc ttcctcgttt ggttcatgta ttttcctttg aataataata ataaatcgg    4560 gctttccata tcggatgctt ttatatctgt gtgtatggag attgtggtat atggtttcat    4620
ctcaagttgt ttacgtcaag aactaaagat atttcctcaa aaaaaaagaa ctaaagatat    4680
aatcaatgtc attaacataa ctcatttcca tgaggagagg acgaaggacg aagtcataat    4740
aagtagattg gttgatattt tataatcatt caaaactgca ggggttataa gatcttcatt    4800
```

```
ttgtagaagt tttagatctt ccgaggggtt ctc                            4833
```

<210> SEQ ID NO 30
<211> LENGTH: 4821
<212> TYPE: DNA
<213> ORGANISM: artificial sequence
<220> FEATURE:
<223> OTHER INFORMATION: proZmUBI_intZmUBI_TaRFL29a_terSbHSP

<400> SEQUENCE: 30

```
gtgcagcgtg acccggtcgt gcccctctct agagataatg agcattgcat gtctaagtta    60
taaaaaatta ccacatattt tttttgtcac acttgtttga agtgcagttt atctatcttt   120
atacatatat ttaaacttta ctctacgaat aatataatct atagtactac aataatatca   180
gtgttttaga gaatcatata aatgaacagt tagacatggt ctaaaggaca attgagtatt   240
ttgacaacag gactctacag ttttatcttt ttagtgtgca tgtgttctcc tttttttttg   300
caaatagctt cacctatata atacttcatc cattttatta gtacatccat ttagggttta   360
gggttaatgg ttttttataga ctaatttttt tagtacatct atttttattct attttagcct   420
ctaaattaag aaaactaaaa ctctatttta gtttttttat ttaataattt agatataaaa   480
tagaataaaa taaagtgact aaaaattaaa caaatacccct ttaagaaatt aaaaaaacta   540
aggaaacatt tttcttgttt cgagtagata atgccagcct gttaaacgcc gtcgacgagt   600
ctaacggaca ccaaccagcg aaccagcagc gtcgcgtcgg gccaagcgaa gcagacggca   660
cggcatctct gtcgctgcct ctggaccccct ctcgagagtt ccgctccacc gttggacttg   720
ctccgctgtc ggcatccaga aattgcgtgg cggagcggca gacgtgagcc ggcacggcag   780
gcggcctcct cctcctctca cggcaccggc agctacgggg gattcctttc ccaccgctcc   840
ttcgctttcc cttcctcgcc cgccgtaata aatagacacc ccctccacac cctctttccc   900
caacctcgtg ttgttcggag cgcacacaca caaccagatctccccccaa atccacccgt   960
cggcacctcc gcttcaaggt acgccgctcg tcctccccccc cccccctct ctaccttctc  1020
tagatcggcg ttccggtcca tggttagggc ccggtagttc tacttctgtt catgtttgtg  1080
ttagatccgt gtttgtgtta gatccgtgct gctagcgttc gtacacggat gcgacctgta  1140
cgtcagacac gttctgattg ctaacttgcc agtgtttctc tttggggaat cctgggatgg  1200
ctctagccgt tccgcagacg ggatcgattt catgattttt tttgtttcgt tgcataggat  1260
ttggtttgcc cttttccttt atttcaatat atgccgtgca cttgtttgtc gggtcatctt  1320
ttcatgcttt tttttgtctt ggttgtgatg atgtggtctg gttgggcggt cgttctagat  1380
cggagtagaa ttaattctgt ttcaaactac ctggtggatt tattaatttt ggatctgtat  1440
gtgtgtgcca tacatattca tagttacgaa ttgaagatga tggatggaaa tatcgatcta  1500
ggataggtat acatgttgat gcgggtttta ctgatgcata tacagagatg cttttttgttc  1560
gcttggttgt gatgatgtgg tgtggttggg cggtcgttca ttcgttctag atcggagtag  1620
aatactgttt caaactacct ggtgtattta ttaattttgg aactgtatgt gtgtgtcata  1680
catcttcata gttacgagtt taagatggat ggaaatatcg atctaggata ggtatacatg  1740
ttgatgtggg tttttactgat gcatatacat gatggcatat gcagcatcta ttcatatgct  1800
ctaaccttga gtacctatct attataataa acaagtatgt tttataatta ttttgatctt  1860
gatatacttg gatgatggca tatgcagcag ctatatgtgg attttttttag ccctgccttc  1920
atacgctatt tatttgcttg gtactgtttc ttttgtcgat gctcaccctg ttgtttggtg  1980
```

```
ttacttctgc aggtctccac catgccccgc ttctcctcca ccacgccaat gtcgccaccc    2040
cgcctccgcc tccgactctg cgcccgccac tcctcctcca cctctcatcc ctcacgcatc    2100
tgggatcccc acgccgcctt cgccgccgcg gcacagcggg cgagctctgg cacgctcact    2160
acggaggacg cacaccacct gtttgacgaa ttgctgcggc ggggcaatcc tgtccaggag    2220
cgtcccttga ataaatttct ggctgccctc gcccgcgcgc ccgcgtccgc atcctgctgc    2280
gatggccccg ccctggcagt cgccctcttc ggccgttttgt cccgagacgt cggacgacgg    2340
gtggcgcagc caaatgtctt cacctatggc gtcctcatgg actgctgctg ccgcgcttgc    2400
cgcacagatc tggtgctcgc cttctttggc cgtctcctca agacgggcct ggaggcaaac    2460
caagtcgtct tcaacaccct cctcaagggc ctttgccaca caaagcgggc ggatgaggct    2520
ctggacgtgc tgcttcacag gatgcctgag ctgggctgca ctcctaatgt ggtggcgtat    2580
aacaccgtta tccatggctt cttttaaggaa ggccatgtaa gcaaggcctg caatctgttc    2640
catgaaatgg cgcagcaggg cgttaagcct aatgtggtga catataactc agttatcgat    2700
gcgctgtgca aggccagagc catggacaag gcagaggtga tccttcgtca gatgattgat    2760
gatggtgttg gacctgataa tgtgacgtat agtagcctca tccatggata ttcctcttca    2820
ggccactgga aggaggcagt tagggtattc aaagagatga caagtcggag ggttacagca    2880
gatgtgcata cttacaacat gtttatgacc tttctttgca aacatggaag aagcaaagaa    2940
gctgcaggaa ttttttgatac catggctatc aagggcctga aacctgacaa cgtttcatat    3000
gctattctcc ttcatgggta tgccgccgaa ggatgcttag ttgatatgat taatctcttc    3060
aattcaatgg aaagagattg tattctacct gactgtcgta tcttcaacat actgattaat    3120
gcatatgcta aatctgggaa gcttgataag gctatgctta tcttcaatga aatgcagaaa    3180
caaggagtga gtccaaatgc agtcacatat tcaaccgtaa tacatgcatt ttgcaagaag    3240
ggtaggttgg atgatgctgt gataaagttt aatcagatga ttgatacagg agtacgaccg    3300
gacgcatctg tttatcgtcc cctaatccag ggttttttgta cacatggcga tttggtgaaa    3360
gcaaaggaat atgttactga aatgatgaag aaaggtatgc ctcctcctga tattatgttc    3420
ttcagttcaa tcatgcagaa cctatgcaca gaaggaaggg taacagaagc acgggatatc    3480
cttgacttga tagtgcacat tggtatgagg cctaatgtta tcatatttaa tttgctgatc    3540
ggtggatact gcctagtccg caagatggca gatgcattga agtatttgga tgatatggtg    3600
tcatatggtt tagaaccttg taactttacg tatggtatac ttattaatgg ctattgcaaa    3660
aatagaagga ttgatgacgg gcttattctg ttcaaagaga tgctgcacaa gggacttaaa    3720
cctacaactt ttaattataa cgtcatactg gatggattat ttctggctgg acaaactgtt    3780
gctgcaaaag agaagtttga tgagatggtt gaatctggag taagtgtgtg cattgataca    3840
tactctataa ttcttggtgg actttgtaga aatagctgca gtagcgaagc gatcacccctt    3900
ttccggaaat taagcgcaat gaatgtgaaa tttgatatta caattgtcaa tatcattatt    3960
ggtgccttat acagggtcga gagaaaccaa gaggctaagg atttgtttgc tgctatgcca    4020
gccaatggct tggttcctaa tgctgttacc tacaccgtaa tgatgacaaa tcttataaaa    4080
gaaggttcag tggaagaagc tgacaatctt ttccttatcca tggagaagag tggctgtact    4140
gccaactctt gcctgttaaa tcatatcatc agaaggttac tggaaaaagg agagatagtc    4200
aaggctggaa attatatgtc taaagttgat gcaagagagct actcacttga agctaaaact    4260
gtttcgctgc tgatctctct gttttcaagg aaagggaaat atagagaaca catcaaattg    4320
cttcctacaa agtatcagtt tctggaagaa gcagccacag ttgaatagaa cgcatccatg    4380
```

```
gacgtggatt gaattgaagg tgtactactg ctgtgctggt ccgtggatcg tggctgtcat    4440
gcatggtttg ctgtgtcttc tacgatatgt acttcccttt gttccgtata tgtacatctt    4500
cctcgtttgg ttcatgtatt ttcctttgaa taataataaa taaatcgggc tttccatatc    4560
ggatgctttt atatctgtgt gtatggagat tgtggtatat ggtttcatct caagttgttt    4620
acgtcaagaa ctaaagatat ttcctcaaaa aaaagaact  aaagatataa tcaatgtcat    4680
taacataact catttccatg aggagaggac gaaggacgaa gtcataataa gtagattggt    4740 tgatattta  taatcattca aaactgcagg ggttataaga tcttcatttt gtagaagttt    4800
tagatcttcc gagggttct c                                               4821
```

<210> SEQ ID NO 31
<211> LENGTH: 24
<212> TYPE: DNA
<213> ORGANISM: artificial sequence
<220> FEATURE:
<223> OTHER INFORMATION: primer GSP1

<400> SEQUENCE: 31
ggatttgccc gcaaatggtt gatc                                             24

<210> SEQ ID NO 32
<211> LENGTH: 47
<212> TYPE: DNA
<213> ORGANISM: artificial sequence
<220> FEATURE:
<223> OTHER INFORMATION: primer GSP2

<400> SEQUENCE: 32
gattacgcca agcttaagaa tcagaattac tgagctaccc cgctctt                    47

<210> SEQ ID NO 33
<211> LENGTH: 22
<212> TYPE: DNA
<213> ORGANISM: artificial sequence
<220> FEATURE:
<223> OTHER INFORMATION: primer P1

<400> SEQUENCE: 33
atgacaaata tggttcgatg gc                                               22

<210> SEQ ID NO 34
<211> LENGTH: 18
<212> TYPE: DNA
<213> ORGANISM: artificial sequence
<220> FEATURE:
<223> OTHER INFORMATION: primer P2

<400> SEQUENCE: 34
gcttggggat cctgaatc                                                    18

<210> SEQ ID NO 35
<211> LENGTH: 19
<212> TYPE: DNA
<213> ORGANISM: artificial sequence
<220> FEATURE:
<223> OTHER INFORMATION: primer P3

<400> SEQUENCE: 35
gctgtcacta gaacggacc                                                   19

<210> SEQ ID NO 36

```
<211> LENGTH: 22
<212> TYPE: DNA
<213> ORGANISM: artificial sequence
<220> FEATURE:
<223> OTHER INFORMATION: primer Ta_Actin_F

<400> SEQUENCE: 36
gccacactgt tccaatctat ga                                            22

<210> SEQ ID NO 37
<211> LENGTH: 22
<212> TYPE: DNA
<213> ORGANISM: artificial sequence
<220> FEATURE:
<223> OTHER INFORMATION: primer Ta_Actin_R

<400> SEQUENCE: 37
gccacactgt tccaatctat ga                                            22

<210> SEQ ID NO 38
<211> LENGTH: 24
<212> TYPE: DNA
<213> ORGANISM: artificial sequence
<220> FEATURE:
<223> OTHER INFORMATION: primer WORF256_F

<400> SEQUENCE: 38
atccccaagc tctagctcat ttag                                          24

<210> SEQ ID NO 39
<211> LENGTH: 22
<212> TYPE: DNA
<213> ORGANISM: artificial sequence
<220> FEATURE:
<223> OTHER INFORMATION: primer WORF256_R

<400> SEQUENCE: 39
gggggctgga agagaaaaga at                                            22

<210> SEQ ID NO 40
<211> LENGTH: 22
<212> TYPE: PRT
<213> ORGANISM: artificial sequence
<220> FEATURE:
<223> OTHER INFORMATION: FLAG

<400> SEQUENCE: 40

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 41
<211> LENGTH: 18
<212> TYPE: RNA
<213> ORGANISM: Triticum timopheevii

<400> SEQUENCE: 41
caccugugca cuuauuua                                                 18

<210> SEQ ID NO 42
<211> LENGTH: 18
<212> TYPE: RNA
<213> ORGANISM: Triticum timopheevii

<400> SEQUENCE: 42
```

```
ucuaucugag ccuuuacg                                                        18
```

<210> SEQ ID NO 43
<211> LENGTH: 20
<212> TYPE: RNA
<213> ORGANISM: Triticum timopheevii

<400> SEQUENCE: 43

```
caccugugca cuuauuuaug                                                      20
```

<210> SEQ ID NO 44
<211> LENGTH: 788
<212> TYPE: PRT
<213> ORGANISM: artificial sequence
<220> FEATURE:
<223> OTHER INFORMATION: Optimized RFL29a 1

<400> SEQUENCE: 44

```
Met Pro Arg Phe Ser Ser Thr Thr Pro Met Ser Pro Pro Arg Leu Arg
1               5                   10                  15

Leu Arg Leu Cys Ala Arg His Ser Ser Ser Thr Ser His Pro Ser Arg
            20                  25                  30

Ile Trp Asp Pro His Ala Ala Phe Ala Ala Ala Ala Gln Arg Ala Ser
        35                  40                  45

Ser Gly Thr Leu Thr Thr Glu Asp Ala His His Leu Phe Asp Glu Leu
    50                  55                  60

Leu Arg Arg Gly Asn Pro Val Gln Glu Arg Pro Leu Asn Lys Phe Leu
65                  70                  75                  80

Ala Ala Leu Ala Arg Ala Pro Ala Ser Ala Ser Cys Cys Asp Gly Pro
                85                  90                  95

Ala Leu Ala Val Ala Leu Phe Gly Arg Leu Ser Arg Asp Val Gly Arg
            100                 105                 110

Arg Val Ala Gln Pro Asn Val Phe Thr Tyr Gly Val Leu Met Asp Cys
        115                 120                 125

Cys Cys Arg Ala Cys Arg Thr Asp Leu Val Leu Ala Phe Phe Gly Arg
    130                 135                 140

Leu Leu Lys Thr Gly Leu Glu Ala Asn Gln Val Val Phe Asn Thr Leu
145                 150                 155                 160

Leu Lys Gly Leu Cys His Thr Lys Arg Ala Asp Glu Ala Leu Asp Val
                165                 170                 175

Leu Leu His Arg Met Pro Glu Leu Gly Cys Thr Pro Asn Val Val Ala
            180                 185                 190

Tyr Asn Thr Val Ile His Gly Phe Phe Lys Glu Gly His Val Ser Lys
        195                 200                 205

Ala Cys Asn Leu Phe His Glu Met Ala Gln Gln Gly Val Lys Pro Asn
    210                 215                 220

Val Val Thr Tyr Asn Ser Val Ile Asp Ala Leu Cys Lys Ala Arg Ala
225                 230                 235                 240

Met Asp Lys Ala Glu Val Val Leu Arg Gln Met Ile Asp Asp Gly Val
                245                 250                 255

Gly Pro Asp Asn Val Thr Tyr Ser Ser Leu Ile His Gly Tyr Ser Ser
            260                 265                 270

Ser Gly His Trp Lys Glu Ala Val Arg Val Phe Lys Glu Met Thr Ser
        275                 280                 285

Arg Arg Val Thr Ala Asp Val His Thr Tyr Asn Met Phe Met Thr Phe
    290                 295                 300
```

```
Leu Cys Lys His Gly Arg Ser Lys Glu Ala Ala Gly Ile Phe Asp Thr
305                 310                 315                 320

Met Ala Ile Lys Gly Leu Lys Pro Asp Asn Val Ser Tyr Ala Ile Leu
            325                 330                 335

Leu His Gly Tyr Ala Ala Glu Gly Cys Leu Val Asp Met Ile Asn Leu
                340                 345                 350

Phe Asn Ser Met Glu Arg Asp Cys Ile Leu Pro Asp Cys Arg Ile Phe
            355                 360                 365

Asn Ile Leu Ile Asn Ala Tyr Ala Lys Ser Gly Lys Leu Asp Lys Ala
370                 375                 380

Met Leu Ile Phe Asn Glu Met Gln Lys Gln Gly Val Ser Pro Asn Ala
385                 390                 395                 400

Val Thr Tyr Ser Thr Val Ile His Ala Phe Cys Lys Lys Gly Arg Leu
                405                 410                 415

Asp Asp Ala Val Ile Lys Phe Asn Gln Met Ile Asp Thr Gly Val Arg
                420                 425                 430

Pro Asn Ala Ser Val Tyr Arg Pro Leu Ile Gln Gly Phe Cys Thr His
            435                 440                 445

Gly Asp Leu Val Lys Ala Lys Glu Tyr Val Thr Glu Met Met Lys Lys
450                 455                 460

Gly Met Pro Pro Asp Ile Met Phe Phe Asn Ser Ile Met Gln Asn
465                 470                 475                 480

Leu Cys Thr Glu Gly Arg Val Thr Glu Ala Arg Asp Ile Leu Asp Leu
                485                 490                 495

Ile Val His Ile Gly Met Arg Pro Asn Val Ile Phe Asn Leu Leu
                500                 505                 510

Ile Gly Gly Tyr Cys Leu Val Arg Lys Met Ala Asp Ala Leu Lys Val
            515                 520                 525

Phe Asp Asp Met Val Ser Tyr Gly Leu Glu Pro Cys Asn Phe Thr Tyr
            530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu His Lys Gly Leu Lys Pro Thr Thr
                565                 570                 575

Phe Asn Tyr Asn Val Ile Leu Asp Gly Leu Phe Leu Ala Gly Gln Thr
            580                 585                 590

Val Ala Ala Lys Glu Lys Phe Asp Glu Met Val Glu Ser Gly Val Ser
                595                 600                 605

Val Cys Ile Asp Thr Tyr Ser Ile Ile Leu Gly Gly Leu Cys Arg Asn
            610                 615                 620

Ser Cys Ser Ser Glu Ala Ile Thr Leu Phe Arg Lys Leu Ser Ala Met
625                 630                 635                 640

Asn Val Lys Phe Asp Ile Thr Ile Val Asn Ile Ile Gly Ala Leu
            645                 650                 655

Tyr Arg Val Glu Arg Asn Gln Glu Ala Lys Asp Leu Phe Ala Ala Met
                660                 665                 670

Pro Ala Asn Gly Leu Val Pro Asn Ala Val Thr Tyr Thr Val Met Met
            675                 680                 685

Thr Asn Leu Ile Lys Glu Gly Ser Val Glu Glu Ala Asp Asn Leu Phe
            690                 695                 700

Leu Ser Met Glu Lys Ser Gly Cys Thr Ala Asn Ser Cys Leu Leu Asn
705                 710                 715                 720
```

His Ile Ile Arg Arg Leu Leu Glu Lys Gly Glu Ile Val Lys Ala Gly
            725                 730                 735

Asn Tyr Met Ser Lys Val Asp Ala Lys Ser Tyr Ser Leu Glu Ala Lys
        740                 745                 750

Thr Val Ser Leu Leu Ile Ser Leu Phe Ser Arg Lys Gly Lys Tyr Arg
        755                 760                 765

Glu His Ile Lys Leu Leu Pro Thr Lys Tyr Gln Phe Leu Glu Glu Ala
    770                 775                 780

Ala Thr Val Glu
785

<210> SEQ ID NO 45
<211> LENGTH: 788
<212> TYPE: PRT
<213> ORGANISM: artificial sequence
<220> FEATURE:
<223> OTHER INFORMATION: Optimized RFL29a 2

<400> SEQUENCE: 45

Met Pro Arg Phe Ser Ser Thr Thr Pro Met Ser Pro Arg Leu Arg
1               5                   10                  15

Leu Arg Leu Cys Ala Arg His Ser Ser Ser Thr Ser His Pro Ser Arg
            20                  25                  30

Ile Trp Asp Pro His Ala Ala Phe Ala Ala Ala Ala Gln Arg Ala Ser
        35                  40                  45

Ser Gly Thr Leu Thr Thr Glu Asp Ala His His Leu Phe Asp Glu Leu
    50                  55                  60

Leu Arg Arg Gly Asn Pro Val Gln Glu Arg Pro Leu Asn Lys Phe Leu
65                  70                  75                  80

Ala Ala Leu Ala Arg Ala Pro Ala Ser Ala Ser Cys Cys Asp Gly Pro
                85                  90                  95

Ala Leu Ala Val Ala Leu Phe Gly Arg Leu Ser Arg Asp Val Gly Arg
            100                 105                 110

Arg Val Ala Gln Pro Asn Val Phe Thr Tyr Gly Val Leu Met Asp Cys
        115                 120                 125

Cys Cys Arg Ala Cys Arg Thr Asp Leu Val Leu Ala Phe Phe Gly Arg
    130                 135                 140

Leu Leu Lys Thr Gly Leu Glu Ala Asn Gln Val Val Phe Asn Thr Leu
145                 150                 155                 160

Leu Lys Gly Leu Cys His Thr Lys Arg Ala Asp Glu Ala Leu Asp Val
                165                 170                 175

Leu Leu His Arg Met Pro Glu Leu Gly Cys Thr Pro Asn Val Val Ala
            180                 185                 190

Tyr Asn Thr Val Ile His Gly Phe Phe Lys Glu Gly His Val Ser Lys
        195                 200                 205

Ala Cys Asn Leu Phe His Glu Met Ala Gln Gln Gly Val Lys Pro Asn
    210                 215                 220

Val Val Thr Tyr Asn Ser Val Ile Asp Ala Leu Cys Lys Ala Arg Ala
225                 230                 235                 240

Met Asp Lys Ala Glu Val Val Leu Arg Gln Met Ile Asp Asp Gly Val
                245                 250                 255

Gly Pro Asp Asn Val Thr Tyr Ser Ser Leu Ile His Gly Tyr Ser Ser
            260                 265                 270

Ser Gly His Trp Lys Glu Ala Val Arg Val Phe Lys Glu Met Thr Ser
        275                 280                 285

```
Arg Arg Val Thr Ala Asp Val His Thr Tyr Asn Met Phe Met Thr Phe
    290             295             300

Leu Cys Lys His Gly Arg Ser Lys Glu Ala Ala Gly Ile Phe Asp Thr
305             310             315             320

Met Ala Ile Lys Gly Leu Lys Pro Asp Asn Val Ser Tyr Ala Ile Leu
                325             330             335

Leu His Gly Tyr Ala Ala Glu Gly Cys Leu Val Asp Met Ile Asn Leu
            340             345             350

Phe Asn Ser Met Glu Arg Asp Cys Ile Leu Pro Asp Cys Arg Ile Phe
        355             360             365

Asn Ile Leu Ile Asn Ala Tyr Ala Lys Ser Gly Lys Leu Asp Lys Ala
370             375             380

Met Leu Ile Phe Asn Glu Met Gln Lys Gln Gly Val Ser Pro Asn Ala
385             390             395             400

Val Thr Tyr Ser Thr Val Ile His Ala Phe Cys Lys Lys Gly Arg Leu
                405             410             415

Asp Asp Ala Val Ile Lys Phe Asn Gln Met Ile Asp Thr Gly Val Arg
            420             425             430

Pro Asn Ala Ser Val Tyr Asn Pro Leu Ile Gln Gly Phe Cys Thr His
        435             440             445

Gly Asp Leu Val Lys Ala Lys Glu Tyr Val Thr Glu Met Met Lys Lys
450             455             460

Gly Met Pro Pro Asp Ile Met Phe Phe Asn Ser Ile Met Gln Asn
465             470             475             480

Leu Cys Thr Glu Gly Arg Val Thr Glu Ala Arg Asp Ile Leu Asp Leu
                485             490             495

Ile Val His Ile Gly Met Arg Pro Asn Val Ile Phe Asn Leu Leu
            500             505             510

Ile Gly Gly Tyr Cys Leu Val Arg Lys Met Ala Asp Ala Leu Lys Val
        515             520             525

Phe Asp Asp Met Val Ser Tyr Gly Leu Glu Pro Cys Asn Phe Thr Tyr
530             535             540

Gly Ile Leu Ile Asn Gly Tyr Cys Lys Asn Arg Arg Ile Asp Asp Gly
545             550             555             560

Leu Ile Leu Phe Lys Glu Met Leu His Lys Gly Leu Lys Pro Thr Thr
                565             570             575

Phe Asn Tyr Asn Val Ile Leu Asp Gly Leu Phe Leu Ala Gly Gln Thr
            580             585             590

Val Ala Ala Lys Glu Lys Phe Asp Glu Met Val Glu Ser Gly Val Ser
        595             600             605

Val Cys Ile Asp Thr Tyr Ser Ile Ile Leu Gly Gly Leu Cys Arg Asn
610             615             620

Ser Cys Ser Ser Glu Ala Ile Thr Leu Phe Arg Lys Leu Ser Ala Met
625             630             635             640

Asn Val Lys Phe Asp Ile Thr Ile Val Asn Ile Ile Gly Ala Leu
                645             650             655

Tyr Arg Val Glu Arg Asn Gln Glu Ala Lys Asp Leu Phe Ala Ala Met
            660             665             670

Pro Ala Asn Gly Leu Val Pro Asn Ala Val Thr Tyr Thr Val Met Met
        675             680             685

Thr Asn Leu Ile Lys Glu Gly Ser Val Glu Glu Ala Asp Asn Leu Phe
690             695             700

Leu Ser Met Glu Lys Ser Gly Cys Thr Ala Asn Ser Cys Leu Leu Asn
```

His Ile Ile Arg Arg Leu Leu Glu Lys Gly Glu Ile Val Lys Ala Gly
705                 710                 715                 720

Asn Tyr Met Ser Lys Val Asp Ala Lys Ser Tyr Ser Leu Glu Ala Lys
            725                 730                 735

Thr Val Ser Leu Leu Ile Ser Leu Phe Ser Arg Lys Gly Lys Tyr Arg
        740                 745                 750

Glu His Ile Lys Leu Leu Pro Thr Lys Tyr Gln Phe Leu Glu Glu Ala
    755                 760                 765

Ala Thr Val Glu
            770                 775                 780

785

<210> SEQ ID NO 46
<211> LENGTH: 2367
<212> TYPE: DNA
<213> ORGANISM: artificial sequence
<220> FEATURE:
<223> OTHER INFORMATION: Optimized RFL29a 3

<400> SEQUENCE: 46

| | | | | | |
|---|---|---|---|---|---|
| atgccccgct | tctcctccac | cacgccaatg | tcgccacccc | gcctccgcct | ccgactctgc | 60 |
| gcccgccact | cctcctccac | ctctcatccc | tcacgcatct | gggatcccca | cgccgccttc | 120 |
| gccgccgcgg | cacagcgggc | gagctctggc | acgctcacta | cggaggacgc | acaccacctg | 180 |
| tttgacgaat | tgctgcggcg | gggcaatcct | gtccaggagc | gtcccttgaa | taaatttctg | 240 |
| gctgccctcg | cccgcgcgcc | cgcgtccgca | tcctgctgcg | atggcccccgc | cctggcagtc | 300 |
| gccctcttcg | gccgttttgtc | ccgagacgtc | ggacgacggg | tggcgcagcc | aaatgtcttc | 360 |
| acctatggcg | tcctcatgga | ctgctgctgc | cgcgcttgcc | gcacagatct | ggtgctcgcc | 420 |
| ttctttggcc | gtctcctcaa | gacgggcctg | gaggcaaacc | aagtcgtctt | caacaccctc | 480 |
| ctcaagggcc | tttgccacac | aaagcgggcg | gatgaggctc | tggacgtgct | gcttcacagg | 540 |
| atgcctgagc | tgggctgcac | tcctaatgtg | gtggcgtata | caccgttat | ccatggcttc | 600 |
| tttaaggaag | ccatgtaag | caaggcctgc | aatctgttcc | atgaaatggc | gcagcagggc | 660 |
| gttaagccta | atgtggtgac | atataactca | gttatcgatg | cgctgtgcaa | ggccagagcc | 720 |
| atggacaagg | cagaggtggt | ccttcgtcag | atgattgatg | atggtgttgg | acctgataat | 780 |
| gtgacgtata | gtagcctcat | ccatggatat | tcctcttcag | gccactggaa | ggaggcagtt | 840 |
| agggtattca | agagatgac | aagtcggagg | gttacagcag | atgtgcatac | ttacaacatg | 900 |
| tttatgacct | tctttgcaa | acatggaaga | agcaaagaag | ctgcaggaat | ttttgatacc | 960 |
| atggctatca | agggcctgaa | acctgacaac | gtttcatatg | ctattctcct | tcatgggtat | 1020 |
| gccgccgaag | gatgcttagt | tgatatgatt | aatctcttca | attcaatgga | aagagattgt | 1080 |
| attctacctg | actgtcgtat | cttcaacata | ctgattaatg | catatgctaa | atctgggaag | 1140 |
| cttgataagg | ctatgcttat | cttcaatgaa | atgcagaaac | aaggagtgag | tccaaatgca | 1200 |
| gtcacatatt | caaccgtaat | acatgcattt | tgcaagaagg | gtaggttgga | tgatgctgtg | 1260 |
| ataaagttta | atcagatgat | tgatacagga | gtacgaccga | acgcatctgt | ttatcgtccc | 1320 |
| ctaatccagg | gttttttgtac | acatggcgat | ttggtgaaaa | caaaggaata | tgttactgaa | 1380 |
| atgatgaaga | aaggtatgcc | tcctcctgat | attatgttct | tcaattcaat | catgcagaac | 1440 |
| ctatgcacag | aaggaagggt | aacagaagca | cggatatcc | ttgacttgat | agtgcacatt | 1500 |
| ggtatgaggc | ctaatgttat | catatttaat | ttgctgatcg | gtggatactg | cctagtccgc | 1560 |

| | |
|---|---|
| aagatggcag atgcattgaa agtatttgat gatatggtgt catatggttt agaaccttgt | 1620 |
| aactttacgt atggtatact tattaatggc tattgcaaaa atagaaggat tgatgacggg | 1680 |
| cttattctgt tcaaagagat gctgcacaag ggacttaaac ctacaacttt taattataac | 1740 |
| gtcatactgg atggattatt tctggctgga caaactgttg ctgcaaaaga gaagtttgat | 1800 |
| gagatggttg aatctggagt aagtgtgtgc attgatacat actctataat tcttggtgga | 1860 |
| ctttgtagaa atagctgcag tagcgaagcg atcacccttt tccggaaatt aagcgcaatg | 1920 |
| aatgtgaaat ttgatattac aattgtcaat atcattattg gtgccttata cagggtcgag | 1980 |
| agaaaccaag aggctaagga tttgtttgct gctatgccag ccaatggctt ggttcctaat | 2040 |
| gctgttacct acaccgtaat gatgacaaat cttataaaag aaggttcagt ggaagaagct | 2100 |
| gacaatcttt tcttatccat ggagaagagc ggctgtactg ccaactcttg cctgttaaat | 2160 |
| catatcatca gaaggttact ggaaaaagga gagatagtca aggctggaaa ttatatgtct | 2220 |
| aaagttgatg caaagagcta ctcacttgaa gctaaaactg tttcgctgct gatctctctg | 2280 |
| ttttcaagga aagggaaata tagagaacac atcaaattgc ttcctacaaa gtatcagttt | 2340 |
| ctggaagaag cagccacagt tgaatag | 2367 |

<210> SEQ ID NO 47
<211> LENGTH: 2367
<212> TYPE: DNA
<213> ORGANISM: artificial sequence
<220> FEATURE:
<223> OTHER INFORMATION: Optimized RFL29a 4

<400> SEQUENCE: 47

| | |
|---|---|
| atgccccgct tctcctccac cacgccaatg tcgccacccc gcctccgcct ccgactctgc | 60 |
| gcccgccact cctcctccac ctctcatccc tcacgcatct gggatcccca cgccgccttc | 120 |
| gccgccgcgg cacagcgggc gagctctggc acgctcacta cggaggacgc acaccacctg | 180 |
| tttgacgaat gctgcggcg gggcaatcct gtccaggagc gtcccttgaa taaatttctg | 240 |
| gctgccctcg cccgcgcgcc cgcgtccgca tcctgctgcg atggccccgc cctggcagtc | 300 |
| gccctcttcg gccgttttgtc ccgagacgtc ggacgacggg tggcgcagcc aaatgtcttc | 360 |
| acctatggcg tcctcatgga ctgctgctgc cgcgcttgcc gcacagatct ggtgctcgcc | 420 |
| ttctttggcc gtctcctcaa gacgggcctg gaggcaaacc aagtcgtctt caacaccctc | 480 |
| ctcaagggcc tttgccacac aaagcgggcg gatgaggctc tggacgtgct gcttcacagg | 540 |
| atgcctgagc tgggctgcac tcctaatgtg gtggcgtata caccgttat ccatggcttc | 600 |
| tttaaggaag gccatgtaag caaggcctgc aatctgttcc atgaaatggc gcagcagggc | 660 |
| gttaagccta atgtggtgac atataactca gttatcgatg cgctgtgcaa ggccagagcc | 720 |
| atggacaagg cagaggtggt ccttcgtcag atgattgatg atggtgttgg acctgataat | 780 |
| gtgacgtata gtagcctcat ccatggatat tcctcttcag gccactggaa ggaggcagtt | 840 |
| agggtattca aagagatgac aagtcggagg gttacagcag atgtgcatac ttacaacatg | 900 |
| tttatgacct ttcttttgcaa acatggaaga agcaaagaag ctgcaggaat ttttgatacc | 960 |
| atggctatca agggcctgaa acctgacaac gtttcatatg ctattctcct tcatgggtat | 1020 |
| gccgccgaag gatgcttagt tgatatgatt aatctcttca attcaatgga aagagattgt | 1080 |
| attctacctg actgtcgtat cttcaacata ctgattaatg catatgctaa atctggggaag | 1140 |
| cttgataagg ctatgcttat cttcaatgaa atgcagaaac aaggagtgag tccaaatgca | 1200 |
| gtcacatatt caaccgtaat acatgcattt tgcaagaagg gtaggttgga tgatgctgtg | 1260 |

```
ataaagttta atcagatgat tgatacagga gtacgaccga acgcatctgt ttataatccc   1320
ctaatccagg gtttttgtac acatggcgat ttggtgaaag caaaggaata tgttactgaa   1380
atgatgaaga aaggtatgcc tcctcctgat attatgttct tcaattcaat catgcagaac   1440
ctatgcacag aaggaagggt aacagaagca cgggatatcc ttgacttgat agtgcacatt   1500
ggtatgaggc ctaatgttat catatttaat ttgctgatcg gtggatactg cctagtccgc   1560
aagatggcag atgcattgaa agtatttgat gatatggtgt catatggttt agaaccttgt   1620
aactttacgt atggtatact tattaatggc tattgcaaaa atagaaggat tgatgacggg   1680
cttattctgt tcaaagagat gctgcacaag ggacttaaac ctacaacttt taattataac   1740
gtcatactgg atggattatt tctggctgga caaactgttg ctgcaaaaga agtttgat    1800 gagatggttg aatctggagt aagtgtgtgc attgatacat actctataat tcttggtgga   1860
ctttgtagaa atagctgcag tagcgaagcg atcacccttt tccggaaatt aagcgcaatg   1920
aatgtgaaat ttgatattac aattgtcaat atcattattg gtgccttata cagggtcgag   1980
agaaaccaag aggctaagga tttgtttgct gctatgccag ccaatggctt ggttcctaat   2040
gctgttacct acaccgtaat gatgacaaat cttataaaag aaggttcagt ggaagaagct   2100
gacaatcttt tcttatccat ggagaagagc ggctgtactg ccaactcttg cctgttaaat   2160
catatcatca aaggttact ggaaaaagga gagatagtca aggctggaaa ttatatgtct   2220
aaagttgatg caaagagcta ctcacttgaa gctaaaactg tttcgctgct gatctctctg   2280
ttttcaagga aagggaaata tagagaacac atcaaattgc ttcctacaaa gtatcagttt   2340
ctggaagaag cagccacagt tgaatag                                      2367
```

<210> SEQ ID NO 48
<211> LENGTH: 2000
<212> TYPE: DNA
<213> ORGANISM: triticum aestivum

<400> SEQUENCE: 48

```
tttcggcgga cgatgctctc cgcaggttgc actggactag cttggtgtga ggcttgcaac    60
tttctcctgt gatgctcatc aacaaaatcg gagatgtcgg tcctcgacgc ctgcggccga   120
tcatttggct tggctgtcga ggtcctcggg tgccgtttgt tcggaggggt cttgatgggt   180
cgtcagcgag gaaatcggag ttgcctgctc gtggagaggc gatgacgatg acattgcagc   240
ctcgacggtg tcctctcgtc agcagtatgt gtgtgatctt gtcagtgcca ggtcggctgg   300
agtgccctat tcgatgggcg tgttttaatt aaccgggcaa ctctcttctt cttaatcagt   360
gaaaatggca agtcttttac ctcgtttcaa aaagagttaa atgcactgga ggtcctaaag   420
gtttcgtcgg ggtgtcactt tagtcctatt tcttccaaaa tgcacccttta ggtcctaatt   480 ctttattaat tggttcaccc gaggtccttt tccacgagcg ctcgctgacc agcacacgtg   540
ccgcattgac ccatgccaca tcgatagagg gtctaaccgc caggcgagaa gcttcgcaaa   600 gagaccccc cccctcttag tggcaccctc tctcctcttt cacggtactt tggcgacatt   660
ggaggcgagc gacagaggca accggaggtg atctggaggt aatttgtgtg ggtgcccgtg   720
aagatgcccc ttctatgacg gccagtgagc aatcctcctc catgttaccg taagaaccct   780
aatcttgtcg atgatcttct cctgtacctc ttctaatatg tcataacttt gtcataatca   840
atagttgtag tccttgattt actttgattt gcataacggt gatacggaca cggcaaaaag   900
gacacaccac cagcggcaac ataccgcgg aagttggagc ttgcttcgcc gcgccggcgg   960
```

```
cggtgctgag gatgttgcca tgctcctcat cttagttgtt tccttgccga ggagcttgaa    1020
gttccggcca tggataggtt taggggacgc gcgcgccgag agagagagca gatttgggga    1080
agaaataaag ccagggactg gggaatgaga agataatgtt tataagggt tttctgtaaa     1140 aagaaagagc aacctacgca gcccttctgt cgatttggca tgggtcaacg caccacacga    1200
gcaggtcaac gagcgctcgt gagaaaaagg acctaggta aaccacttac taaagaatta    1260
ggacctaaag gtgcattttg gacgaaataa gactaaagtg acaccctgac gaattttta    1320 ggaccttgag tgcatttaac tctttcaaaa aataaagatg ctaaaaaaac taaatgctta    1380
aaaatacatt ttctctatggg aatacttaaa aatactagta taatttgatg cttcctagt    1440 atatttctag ggcttacaac taaatttata ttcttggtct aaataaaatt ataatctgat    1500
aaattatgtg atatgaatat agccatatga gaccataatt taattttacc tgcaaaaagt    1560
aagtaatagt agtagtagta ctacatactc cctccgtccg gaaatacttg tcgaagaatt    1620
tgatgaaaat ggatgcatct agaacaagaa tacatctaga tacatcaatc tccctgacaa    1680
gtatttccga gcggagggag tactagataa tactccctcc gttcctaaat aattgtcttt    1740
ctagctatct caaataaact acaacatacg gatgtatgta gacatgtttt agagtgtaga    1800
ttcactcatt ttgttccgta tgtagtcatt tgttgaaatc tctagagaga caattattta    1860
ggaacggagg gagtaagata actaccctaa aaaaaaagat aactgaaggt tgccacctag    1920
cacattcaca ttggtacaac ttggaaaagc acagccccgt cgtcctgctc ccagttgagt    1980
tcgcgaccta cacaccggcc                                                2000

<210> SEQ ID NO 49
<211> LENGTH: 812
<212> TYPE: DNA
<213> ORGANISM: triticum aestivum

<400> SEQUENCE: 49
ttggtacatg atatctgaaa tttaatttgc atcgcttgcc atgggtccgt ctgcttgtac       60
aagaaatgca ttttctattt gtaaatagga agtcagttta gaacaagcca tcaggatgac      120
gcaaagagta caattcagtt gcaccaccaa taaaaaggca gaactagggc tgccaaaaca      180
acactgaatc aaaactcaaa cagaaggagc agcaaacttt ttttttttg aagctggaca      240 gtctgctagc caaacaacta caggagactg tcaggcgggg catgtagtgg ctggcgtcta      300
agcgcctttg cttcttccac catccatggc ttagcctcac acggaatcga gtcaaccaat      360
tcccgtcggt tttgggtggc tcccttgaag atgcaattgt tttcagcggc cagatacgca      420
tggtcagatt aatcagcgag tgtgccctt ctgtctggtt cgagaaagaa tttgaagagc      480
tgagcttgtc cctgctggaa ccagtttgag gttagttaat cataacaggg tactagagag      540
gtgttttatt gactgttgat gtgtaatatg ttatatgcca tcctcttgat gattacggtg      600
atctgtgaag aggcagcatg caaaagtctg aatcacatat gcttatgtaa ttgtgttatt      660
atttgtgcag cttctagacc ttttgccttg tagatggcta catggatcta gttgtagcaa      720
tctgtaactg ttagtgtttt gtatatgctg gcattgatga ttagggtgac ttgtgaagca      780
tgcagaagtc tgaatcgtac atgcttgtct ag                                    812

<210> SEQ ID NO 50
<211> LENGTH: 5179
<212> TYPE: DNA
<213> ORGANISM: artificial sequence
<220> FEATURE:
<223> OTHER INFORMATION: optimised RFL29a expression cassette 1
```

<400> SEQUENCE: 50

```
tttcggcgga cgatgctctc cgcaggttgc actggactag cttggtgtga ggcttgcaac     60
tttctcctgt gatgctcatc aacaaaatcg gagatgtcgg tcctcgacgc ctgcggccga    120
tcatttggct tggctgtcga ggtcctcggg tgccgtttgt tcggagggggt cttgatgggt   180
cgtcagcgag gaaatcggag ttgcctgctc gtggagaggc gatgacgatg acattgcagc    240
ctcgacggtg tcctctcgtc agcagtatgt gtgtgatctt gtcagtgcca ggtcggctgg    300
agtgccctat tcgatgggcg tgttttaatt aaccgggcaa ctctcttctt cttaatcagt    360
gaaaatggca agtcttttac ctcgtttcaa aagagttaa atgcactgga ggtcctaaag     420
gtttcgtcgg ggtgtcactt tagtcctatt tcttccaaaa tgcacccttta ggtcctaatt   480
ctttattaat tggttcaccc gaggtccttt tccacgagcg ctcgctgacc agcacacgtg    540
ccgcattgac ccatgccaca tcgatagagg gtctaaccgc caggcgagaa gcttcgcaaa   600
gagaccccc ccctcttag tggcaccctc tctcctcttt cacggtactt tggcgacatt     660
ggaggcgagc gacagaggca accggaggtg atctggaggt aatttgtgtg ggtgcccgtg   720
aagatgcccc ttctatgacg gccagtgagc aatcctcctc catgttaccg taagaaccct   780
aatcttgtcg atgatcttct cctgtacctc ttctaatatg tcataacttt gtcataatca   840
atagttgtag tccttgattt actttgattt gcataacggt gatacggaca cggcaaaaag    900
gacacaccac cagcggcaac ataccgccg aagttggagc ttgcttcgcc cgcccggcgg     960
cggtgctgag gatgttgcca tgctcctcat cttagttgtt tccttgccga ggagcttgaa   1020
gttccggcca tggataggtt taggggacgc gcgcgccgag agagagagca gatttgggga   1080
agaaataaag ccagggactg gggaatgaga agataatgtt tataagggt tttctgtaaa    1140
aagaaagagc aacctacgca gcccttctgt cgatttggca tgggtcaacg caccacacga    1200
gcaggtcaac gagcgctcgt gagaaaaagg acctagggta aaccacttac taaagaatta   1260
ggacctaaag gtgcattttg gacgaaataa gactaaagtg acaccctgac gaatttttta    1320
ggaccttgag tgcatttaac tctttcaaaa aataaagatg ctaaaaaaac taaatgctta    1380
aaaatacatt tttctatggg aatacttaaa aatactagta taatttgatg gcttcctagt    1440
atatttctag ggcttacaac taaatttata ttcttggtct aaataaaatt ataatctgat    1500
aaattatgtg atatgaatat agccatatga gaccataatt taattttacc tgcaaaaagt   1560
aagtaatagt agtagtagta ctacatactc cctccgtccg gaaatacttg tcgaagaatt   1620
tgatgaaaat ggatgcatct agaacaagaa tacatctaga tacatcaatc tccctgacaa    1680
gtatttccga gcggagggag tactagataa tactccctcc gttcctaaat aattgtcttt    1740
ctagctatct caaataaact acaacatacg gatgtatgta gacatgtttt agagtgtaga    1800
ttcactcatt ttgttccgta tgtagtcatt tgttgaaatc tctagagaga caattattta    1860
ggaacggagg gagtaagata actaccctaa aaaaaaagat aactgaaggt tgccacctag    1920
cacattcaca ttggtacaac ttggaaaagc acagccccgt cgtcctgctc ccagttgagt    1980
tcgcgaccta cacaccggcc atgcccgct tctcctccac acgccaatg tcgccacccc     2040
gcctccgcct ccgactctgc gcccgccact cctcctccac ctctcatccc tcacgcatct   2100
gggatcccca cgccgccttc gccgccgcgg cacagcgggc gagctctggc acgctcacta    2160
cggaggacgc acaccacctg tttgacgaat tgctgcggcg gggcaatcct gtccaggagc    2220
gtcccttgaa taaatttctg gctgccctcg cccgcgcgcc cgcgtccgca tcctgctgcg    2280
```

-continued

| | |
|---|---|
| atggccccgc cctggcagtc gccctcttcg gccgtttgtc ccgagacgtc ggacgacggg | 2340 |
| tggcgcagcc aaatgtcttc acctatggcg tcctcatgga ctgctgctgc cgcgcttgcc | 2400 |
| gcacagatct ggtgctcgcc ttctttggcc gtctcctcaa gacgggcctg gaggcaaacc | 2460 |
| aagtcgtctt caacaccctc ctcaaggggc tttgccacac aaagcgggcg gatgaggctc | 2520 |
| tggacgtgct gcttcacagg atgcctgagc tgggctgcac tcctaatgtg gtggcgtata | 2580 |
| acaccgttat ccatggcttc tttaaggaag gccatgtaag caaggcctgc aatctgttcc | 2640 |
| atgaaatggc gcagcagggc gttaagccta atgtggtgac atataactca gttatcgatg | 2700 |
| cgctgtgcaa ggccagagcc atggacaagg cagaggtggt ccttcgtcag atgattgatg | 2760 |
| atggtgttgg acctgataat gtgacgtata gtagcctcat ccatggatat tcctcttcag | 2820 |
| gccactggaa ggaggcagtt agggtattca agagatgac aagtcggagg ttacagcag | 2880 |
| atgtgcatac ttacaacatg tttatgacct ttctttgcaa acatggaaga agcaaagaag | 2940 |
| ctgcaggaat ttttgatacc atggctatca agggcctgaa acctgacaac gtttcatatg | 3000 |
| ctattctcct tcatgggtat gccgccgaag gatgcttagt tgatatgatt aatctcttca | 3060 |
| attcaatgga aagagattgt attctacctg actgtcgtat cttcaacata ctgattaatg | 3120 |
| catatgctaa atctgggaag cttgataagg ctatgcttat cttcaatgaa atgcagaaac | 3180 |
| aaggagtgag tccaaatgca gtcacatatt caaccgtaat acatgcattt gcaagaagg | 3240 |
| gtaggttgga tgatgctgtg ataaagttta atcagatgat tgatacagga gtacgaccga | 3300 |
| acgcatctgt ttatcgtccc ctaatccagg ttttttgtac acatggcgat ttggtgaaag | 3360 |
| caaaggaata tgttactgaa atgatgaaga aggtatgcc tcctcctgat attatgttct | 3420 |
| tcaattcaat catgcagaac ctatgcacag aaggaagggt aacagaagca cgggatatcc | 3480 |
| ttgacttgat agtgcacatt ggtatgaggc ctaatgttat catatttaat ttgctgatcg | 3540 |
| gtggatactg cctagtccgc aagatggcag atgcattgaa agtatttgat gatatggtgt | 3600 |
| catatggttt agaaccttgt aactttacgt atggtatact tattaatggc tattgcaaaa | 3660 |
| atagaaggat tgatgacggg cttattctgt tcaaagagat gctgcacaag ggacttaaac | 3720 |
| ctacaacttt taattataac gtcatactgg atggattatt tctggctgga caaactgttg | 3780 |
| ctgcaaaaga gaagtttgat gagatggttg aatctggagt aagtgtgtgc attgatacat | 3840 |
| actctataat tcttggtgga cttttgtagaa atagctgcag tagcgaagcg atcacccttt | 3900 |
| tccggaaatt aagcgcaatg aatgtgaaat ttgatattac aattgtcaat atcattattg | 3960 |
| gtgccttata cagggtcgag agaaaccaag aggctaagga tttgtttgct gctatgccag | 4020 |
| ccaatggctt ggttcctaat gctgttacct acaccgtaat gatgacaaat cttataaaag | 4080 |
| aaggttcagt ggaagaagct gacaatcttt tcttatccat ggagaagagc ggctgtactg | 4140 |
| ccaactcttg cctgttaaat catatcatca gaaggttact ggaaaaagga gagatagtca | 4200 |
| aggctggaaa ttatatgtct aaagttgatg caaagagcta ctcacttgaa gctaaaactg | 4260 |
| tttcgctgct gatctctctg ttttcaagga aagggaaata tagagaacac atcaaattgc | 4320 |
| ttcctacaaa gtatcagttt ctggaagaag cagccacagt tgaatagttg gtacatgata | 4380 |
| tctgaaattt aatttgcatc gcttgccatg ggtccgtctg cttgtacaag aaatgcatt | 4440 |
| tctatttgta aataggaagt cagtttagaa caagccatca ggatgacgca aagagtacaa | 4500 |
| ttcagttgca ccaccaataa aaaggcagaa ctagggctgc aaaacaaca ctgaatcaaa | 4560 |
| actcaaacag aaggagcagc aaacttttt ttttttgaag ctggacagtc tgctagccaa | 4620 |
| acaactacag gagactgtca ggcggggcat gtagtggctg gcgtctaagc gcctttgctt | 4680 |

```
cttccaccat ccatggctta gcctcacacg gaatcgagtc aaccaattcc cgtcggtttt    4740
gggtggctcc cttgaagatg caattgtttt cagcggccag atacgcatgg tcagattaat    4800
cagcgagtgt gccccttctg tctggttcga gaaagaattt gaagagctga gcttgtccct    4860
gctggaacca gtttgaggtt agttaatcat aacagggtac tagagaggtg ttttattgac    4920
tgttgatgtg taatatgtta tatgccatcc tcttgatgat tacggtgatc tgtgaagagg    4980
cagcatgcaa aagtctgaat cacatatgct tatgtaattg tgttattatt tgtgcagctt    5040
ctagaccttt tgccttgtag atggctacat ggatctagtt gtagcaatct gtaactgtta    5100
gtgttttgta tatgctggca ttgatgatta gggtgacttg tgaagcatgc agaagtctga    5160
atcgtacatg cttgtctag                                                 5179
```

<210> SEQ ID NO 51
<211> LENGTH: 5179
<212> TYPE: DNA
<213> ORGANISM: artificial sequence
<220> FEATURE:
<223> OTHER INFORMATION: optimised RFL29a expression cassette 2

<400> SEQUENCE: 51

```
tttcggcgga cgatgctctc cgcaggttgc actggactag cttggtgtga ggcttgcaac      60
tttctcctgt gatgctcatc aacaaaatcg gagatgtcgg tcctcgacgc ctgcggccga     120
tcatttggct tggctgtcga ggtcctcggg tgccgtttgt tcgagggggt cttgatgggt     180
cgtcagcgag gaaatcggag ttgcctgctc gtggagaggc gatgacgatg acattgcagc     240
ctcgacggtg tcctctcgtc agcagtatgt gtgtgatctt gtcagtgcca ggtcggctgg     300
agtgccctat tcgatgggcg tgttttaatt aaccgggcaa ctctcttctt cttaatcagt     360
gaaaatggca agtcttttac ctcgtttcaa aaagagttaa atgcactgga ggtcctaaag     420
gtttcgtcgg ggtgtcactt tagtcctatt tcttccaaaa tgcacccttta ggtcctaatt    480 ctttattaat tggttcaccc gaggtccttt tccacgagcg ctcgctgacc agcacacgtg     540
ccgcattgac ccatgccaca tcgatagagg gtctaaccgc caggcgagaa gcttcgcaaa    600
gagacccccc cccctcttag tggcaccctc tctcctcttt cacggtactt tggcgacatt     660
ggaggcgagc gacagaggca accggaggtg atctggaggt aatttgtgtg ggtgcccgtg     720
aagatgcccc ttctatgacg gccagtgagc aatcctcctc catgttaccg taagaaccct     780
aatcttgtcg atgatcttct cctgtacctc ttctaatatg tcataacttt gtcataatca     840
atagttgtag tccttgattt actttgattt gcataacggt gatacggaca cggcaaaaag     900
gacacaccac cagcggcaac ataccccgccg aagttggagc ttgcttcgcc gcgccggcgg     960
cggtgctgag gatgttgcca tgctcctcat cttagttgtt tccttgccga ggagcttgaa    1020
gttccggcca tggataggtt taggggacgc gcgcgccgag agagagagca gatttgggga    1080
agaaataaag ccaggactg gggaatgaga agataatgtt tataagggt tttctgtaaa    1140 aagaaagagc aacctacgca gcccttctgt cgatttggca tgggtcaacg caccacacga    1200
gcaggtcaac gagcgctcgt gagaaaaagg acctaggta aaccacttac taaagaatta    1260
ggacctaaag gtgcattttg gacgaaataa gactaaagtg acaccctgac gaattttta    1320 ggaccttgag tgcatttaac tctttcaaaa aataaagatg ctaaaaaaac taaatgctta    1380
aaaatacatt ttctatggg aatacttaaa aatactagta taatttgatg gcttcctagt    1440
atatttctag ggcttacaac taaatttata ttcttggtct aaataaaatt ataatctgat    1500
```

```
aaattatgtg atatgaatat agccatatga gaccataatt taattttacc tgcaaaaagt    1560
aagtaatagt agtagtagta ctacatactc cctccgtccg gaaatacttg tcgaagaatt    1620
tgatgaaaat ggatgcatct agaacaagaa tacatctaga tacatcaatc tccctgacaa    1680
gtatttccga gcggagggag tactagataa tactccctcc gttcctaaat aattgtcttt    1740
ctagctatct caaataaact acaacatacg gatgtatgta gacatgtttt agagtgtaga    1800
ttcactcatt ttgttccgta tgtagtcatt tgttgaaatc tctagagaga caattattta    1860
ggaacggagg gagtaagata actaccctaa aaaaaaagat aactgaaggt tgccacctag    1920
cacattcaca ttggtacaac ttggaaaagc acagccccgt cgtcctgctc ccagttgagt    1980
tcgcgaccta cacaccggcc atgccccgct tctcctccac acgccaatg tcgccacccc    2040
gcctccgcct ccgactctgc gcccgccact cctcctccac ctctcatccc tcacgcatct    2100
gggatcccca cgccgccttc gccgccgcgg cacagcgggc gagctctggc acgctcacta    2160
cggaggacgc acaccacctg tttgacgaat tgctgcggcg gggcaatcct gtccaggagc    2220
gtcccttgaa taaatttctg gctgccctcg cccgcgcgcc cgcgtccgca tcctgctgcg    2280
atggccccgc cctggcagtc gccctcttcg gccgtttgtc ccgagacgtc ggacgacggg    2340
tggcgcagcc aaatgtcttc acctatggcg tcctcatgga ctgctgctgc cgcgcttgcc    2400
gcacagatct ggtgctcgcc ttctttggcc gtctcctcaa gacgggcctg gaggcaaacc    2460
aagtcgtctt caacaccctc ctcaagggcc tttgccacac aaagcgggcg gatgaggctc    2520
tggacgtgct gcttcacagg atgcctgagc tgggctgcac tcctaatgtg gtggcgtata    2580
acaccgttat ccatggcttc tttaaggaag gccatgtaag caaggcctgc aatctgttcc    2640
atgaaatggc gcagcagggc gttaagccta atgtggtgac atataactca gttatcgatg    2700
cgctgtgcaa ggccagagcc atggacaagg cagaggtggt ccttcgtcag atgattgatg    2760
atggtgttgg acctgataat gtgacgtata gtagcctcat ccatggatat tcctcttcag    2820
gccactggaa ggaggcagtt agggtattca aagagatgac aagtcggagg gttacagcag    2880
atgtgcatac ttacaacatg tttatgacct ttctttgcaa acatggaaga agcaaagaag    2940
ctgcaggaat ttttgatacc atggctatca agggcctgaa acctgacaac gtttcatatg    3000
ctattctcct tcatgggtat gccgccgaag gatgcttagt tgatatgatt aatctcttca    3060
attcaatgga aagagattgt attctacctg actgtcgtat cttcaacata ctgattaatg    3120
catatgctaa atctgggaag cttgataagg ctatgcttat cttcaatgaa atgcagaaac    3180
aaggagtgag tccaaatgca gtcacatatt caaccgtaat acatgcattt tgcaagaagg    3240
gtaggttgga tgatgctgtg ataaagttta atcagatgat tgatacagga gtacgaccga    3300
acgcatctgt ttataatccc ctaatccagg gtttttgtac acatggcgat ttggtgaaag    3360
caaaggaata tgttactgaa atgatgaaga aaggtatgcc tcctcctgat attatgttct    3420
tcaattcaat catgcagaac ctatgcacag aaggaagggt aacagaagca cgggatatcc    3480
ttgacttgat agtgcacatt ggtatgaggc ctaatgttat catatttaat ttgctgatcg    3540
gtggatactg cctagtccgc aagatggcag atgcattgaa agtatttgat gatatggtgt    3600
catatggttt agaaccttgt aactttacgt atggtatact tattaatggc tattgcaaaa    3660
atagaaggat tgatgacggg cttattctgt tcaaagagat gctgcacaag ggacttaaac    3720
ctacaacttt taattataac gtcatactgg atggattatt tctggctgga caaactgttg    3780
ctgcaaaaga gaagtttgat gagatggttg aatctggagt aagtgtgtgc attgatacat    3840
actctataat tcttggtgga cttttgtagaa atagctgcag tagcgaagcg atcacccttt    3900
```

```
tccggaaatt aagcgcaatg aatgtgaaat ttgatattac aattgtcaat atcattattg    3960 gtgcctttata cagggtcgag agaaaccaag aggctaagga tttgtttgct gctatgccag   4020
ccaatggctt ggttcctaat gctgttacct acaccgtaat gatgacaaat cttataaaag    4080
aaggttcagt ggaagaagct gacaatcttt tcttatccat ggagaagagc ggctgtactg    4140
ccaactcttg cctgttaaat catatcatca gaaggttact ggaaaaagga gagatagtca    4200
aggctggaaa ttatatgtct aaagttgatg caaagagcta ctcacttgaa gctaaaactg    4260
tttcgctgct gatctctctg ttttcaagga aagggaaata tagagaacac atcaaattgc    4320
ttcctacaaa gtatcagttt ctggaagaag cagccacagt tgaatagttg gtacatgata    4380
tctgaaattt aatttgcatc gcttgccatg ggtccgtctg cttgtacaag aaatgcattt    4440
tctatttgta aataggaagt cagtttagaa caagccatca ggatgacgca agagtacaa     4500 ttcagttgca ccaccaataa aaaggcagaa ctagggctgc aaaacaaca ctgaatcaaa     4560 actcaaacag aaggagcagc aaactttttt tttttgaag ctggacagtc tgctagccaa     4620
acaactacag gagactgtca ggcggggcat gtagtggctg gcgtctaagc gccttttgctt   4680 cttccaccat ccatggctta gcctcacacg gaatcgagtc aaccaattcc cgtcggtttt    4740
gggtggctcc cttgaagatg caattgtttt cagcggccag atacgcatgg tcagattaat    4800
cagcgagtgt gccccttctg tctggttcga gaaagaattt gaagagctga gcttgtccct    4860
gctggaacca gtttgaggtt agttaatcat aacagggtac tagagaggtg ttttattgac    4920
tgttgatgtg taatatgtta tatgccatcc tcttgatgat tacggtgatc tgtgaagagg    4980
cagcatgcaa aagtctgaat cacatatgct tatgtaattg tgttattatt tgtgcagctt    5040 ctagacctttt tgccttgtag atggctacat ggatctagtt gtagcaatct gtaactgtta    5100
gtgttttgta tatgctggca ttgatgatta gggtgacttg tgaagcatgc agaagtctga    5160
atcgtacatg cttgtctag                                                 5179

<210> SEQ ID NO 52
<211> LENGTH: 22
<212> TYPE: DNA
<213> ORGANISM: artificial sequence
<220> FEATURE:
<223> OTHER INFORMATION: Primer KASPar AS1

<400> SEQUENCE: 52
agaggcaaat tgggcaaagg ac                                             22

<210> SEQ ID NO 53
<211> LENGTH: 25
<212> TYPE: DNA
<213> ORGANISM: artificial sequence
<220> FEATURE:
<223> OTHER INFORMATION: Primer KASPar AS2

<400> SEQUENCE: 53
agaatctgtc tctccattcc tcgtg                                          25
```

-continued

```
<210> SEQ ID NO 54
<211> LENGTH: 26
<212> TYPE: DNA
<213> ORGANISM: artificial sequence
<220> FEATURE:
<223> OTHER INFORMATION: Primer KASPar C

<400> SEQUENCE: 54
atggtgtaag accgtcgact atttgg                                    26
```

GENE RESPONSIBLE FOR CYTOPLASMIC MALE STERILITY

BACKGROUND

By 2050 the world's human population is projected to exceed nine billion (United Nations, 2017). At the same time the area of arable land is predicted to shrink from 0.38 ha per person in 1970 to 0.15 ha per person in 2050 (FAOSTAT 2017). Thus, in order to meet future food demands, the yield per hectare needs to increase, ideally without elevated usage of water or fertilizer. By contributing 11% to the total crop production, wheat is one of the most important small grain crops cultivated worldwide (FAOSTAT 2017, Langridge 2017). After the introduction of Green Revolution crops in 1960, the creation of hybrid varieties in crops such as rice, corn and sorghum lifted their productivity significantly and contributed greatly to overall cereal seed production that today makes up 50% of global food production (FAOSTAT 2017). Due to lack of an efficient pollination control system, hybrid production in wheat relies mainly on the use of chemical hybridizing agents (CHA) and is only marginally applied (Whitford et al., 2013). Likely as a result of this, the rate of wheat yield gains has been slower over the last decade compared to corn or rice yield gains (FAOSTAT 2017, Whitford et al., 2013).

The main goal of hybrid production is to take advantage of heterosis to produce more resource- and energy-efficient plants with higher and more stable yields. It is estimated that yield improvements associated with heterosis in wheat could reach up to 15% (Longin et al., 2012). Hybrid production requires a method to block self-pollination of autogamous plants, like wheat, where manual separation of male and female sexual organs is labour-intensive and thus inapplicable on an industrial scale (Chase et al., 2007). A system that has been successfully used for production of hybrids in several crop plants including maize, rice and sorghum is the three-line breeding system based on cytoplasmic male sterility (CMS), a genetically conditioned trait that leads to plant sterility (Chen and Liu 2014; Bohra et al., 2016; Yamagishi and Bhat 2014; Saxena et al., 2015). It requires three types of breeding lines: a cytoplasmic male sterile line (A line), which carries the CMS-causing gene, a maintainer line (B line) which is required for propagating the A line whilst maintaining the sterility and a restorer line (R line) which carries a restorer-of-fertility (Rf) gene able to restore fertility of F1 plants (Chen and Liu 2014). Historically, the strong inbreeding nature governed by the unique architecture and development of wheat flowers complemented by the lack of suitable Rf genes are the major factors limiting the application of CMS to hybrid seed production in wheat (Whitford et al., 2013).

CMS in cultivated wheats originates from interspecific crosses between bread wheat (*Triticum aestivum*) as a pollen donor and wild wheat e.g. *Triticum timopheevii*. or related species such as *Aegilops* or *Hordeum*, and backcrossing to bread wheat (Whitford et al., 2013). The first case of male sterility in wheat was reported in 1951 when the nucleus of *Aegilops caudata* cells was substituted by the nucleus from *Triticum aestivum* (Kihara, 1951). Subsequently the T-type CMS wheat (also known as G-type CMS) was derived from cross between *Triticum timopheevii* as female parent and bread wheat as the male parent (Wilson and Ross 1962).

It was proposed that the T-CMS is caused by a single gene designated orf256 in the mitochondrial genome of *T. timopheevii* (Rathburn and Hedgcoth, 1991). Sequence analysis has revealed that the region from −228 to +33 (relative to the start codon) of orf256 is identical to the analogous region from cox1 (encoding subunit 1 of mitochondrial complex IV) in *T. aestivum*, whereas the rest of orf256, including the 3' flanking region, is not related to cox1 (Rathburn and Hedgcoth, 1991; Song and Hedgcoth, 1994A). Most probably, a single recombination event has led to the formation of orf256 in *T. timopheevii* mitochondrial DNA (mtDNA) (Rathburn and Hedgcoth, 1991; Song and Hedgcoth, 1994A). It has been documented that although the gene organization of orf256 fragments from *T. timopheevi*, CMS (*T. aestivum* nucleus, *T. timopheevii* mitochondria), and fertility-restored lines are identical, orf256 transcript processing is altered by different nuclear backgrounds (Rathburn and Hedgcoth 1991; Song and Hedgcoth, 1994A). The name Orf256 originates from the 256 amino acids that are encoded by the orf256 coding sequence (Rathburn and Hedgcoth, 1991). Antibodies directed towards a peptide corresponding to a part of the encoded amino acid sequence of orf256 detect a 7 kDa protein on western blots of mitochondrial proteins from T-CMS wheat but not on blots of mitochondrial proteins from *T. aestivum*, *T. timopheevi*, or T-CMS plants restored to fertility by introduction of nuclear genes for fertility restoration (Song and Hedgcoth 1994B). Moreover, it has been shown that Orf256 is anchored in the inner mitochondrial membrane (Song and Hedgcoth 1994B). Since the first molecular studies on T-CMS performed by Hedgcoth and colleagues, no follow-up studies were initiated for the next 25 years.

It is known today that restorer of fertility (Rf) proteins are encoded in the nucleus and post-translationally targeted to mitochondria, where they prevent the accumulation of RNA encoding CMS-specific ORFs (Kazama et al., 2008; Bentolia et al., 2002). The majority of Rf genes in higher plants identified to date encode pentatricopeptide repeat (PPR) proteins (Kotchoni et al., 2010; Chen and Liu 2013). The PPR family has highly expanded in land plants, and the members of the family involved in CMS, referred to as Restorer-of-fertility-like (Rfl) tend to exist as gene clusters at two to three genomic positions (Schmitz-Linneweber and Small, 2008, Fujii et al., 2011; Melonek et al, 2016). For example, several Rf genes map to a gene cluster on chromosome 10 in rice, including Rf1a and Rf1b for CMS-Chinsurash Boro II and Rf4 for CMS-wild abortive (Akagi et al., 2004; Wang et al., 2004; Zhang et al., 2002). Recent global analysis of the PPR family in the wheat RefSeq v1.0 genome revealed the presence of 207 Rf1 genes, the majority of which are organised in clusters on chromosome 1, 2 and 6 (The International Wheat Genome Sequencing Consortium, 2018).

Several restorer genes controlling fertility in the T-CMS system have been reported in *Triticum aestivum*, namely Rf1 (chr1A) (Du et al. 1991), Rf2 (chr7D) (Bahl and Maan 1972; Maan et al. 1984), Rf3 (chr1B) (Tahir and Tsunewak. K 1969), Rf4 (chr6B) (Maan et al. 1984), Rf5 (chr6D) (Bahl and Maan 1972), Rf6 (chr5D) (Bahl and Maan 1972), Rf7 (chr7B) (Bahl and Maan 1972) and Rf8 (chr2D) (Sinha et al. 2013). The Rf1 locus was first described in the *T. timopheevii* introgression line R3 (Livers 1964; Bahl and Maan 1973) and was later found to be located on chromosome 1A (Robertson and Curtis 1967). A restorer locus on this chromosome was also found in three other *T. timopheevii* introgression lines, the spring wheat accession R113 and its descendants (Bahl and Maan 1973; Maan et al. 1984; Maan 1985; Du et al. 1991). Recently, the Rf1 locus was genetically mapped to a 8.17 Mbp region on chromosome 1A (Greyer et al., 2017). In addition, a modifier locus for Rf1 was identified on chromosome 1B (Greyer et al., 2017). Rf3 was reported as one of the most effective restorer loci (Ma and Sorrells, 1995; Kojima et al, 1997; Ahmed et al 2001; Geyer et al 2016). Two SNP markers allowed the location of the Rf3 locus within a 2 cM fragment on chromosome 1B (Geyer et al, 2017). The genomic location of both Rf1 and Rf3 overlaps with the location of RFL clusters described to be present on the wheat chromosome 1A and 1B (International Wheat Genome Sequencing Consortium, 2018).

For effective use of CMS and Rf genes in hybrid breeding programs, it is crucial to understand the molecular mechanisms linking them in plant mitochondria. The present invention deals with the identification of a new gene, orf279 that causes male sterility in T-CMS wheat, through molecular characterization of the Rf1- and Rf3-associated restoration mechanism. The present invention deals with new molecular and breeding tools developed from orf279 gene sequence information.

SUMMARY

A first aspect of the invention is an isolated nucleic acid encoding Orf279 protein of amino acid sequence at least 95% identical to SEQ ID NO: 4.

In a second aspect, the present application concerns methods for detecting orf279 DNA, orf279 RNA or Orf279 protein in a sample.

In a third aspect, the present invention relates to a method for identifying a functional Rf gene encoding a protein able to bind to orf279 RNA.

In a fourth aspect, the present invention concerns a method for the design and the optimization of a synthetic PPR protein capable of binding and preventing expression of orf279 RNA.

In a fifth aspect, the present invention relates to a method for obtaining a sterile plant.

In a sixth aspect, the present invention relates to a method for obtaining a fertile wheat plant.

DETAILED DESCRIPTION

Definitions

Whenever reference to a "plant" or "plants" is made, it is understood that also plant parts (cells, tissues or organs, seed pods, seeds, severed parts such as roots, leaves, flowers, pollen, etc.), progeny of the plants which retain the distinguishing characteristics of the parents (especially, male fertility associated with the claimed Rf nucleic acids), such as seed obtained by selfing or crossing, e.g. hybrid seeds (obtained by crossing two inbred parent plants), hybrid plants and plant parts derived therefrom are encompassed herein, unless otherwise indicated.

As used herein, the term "wheat plant" refers to species of the genus *Triticum* as for example, *T. aestivum*, *T. aethiopicum*, *T. araraticum*, *T. boeoticum*, *T. carthlicum*, *T. compactum*, *T. dicoccoides*, *T. dicoccon*, *T. durum*, *T. ispahanicum*, *T. karamyschevii*, *T. macha*, *T. militinae*, *T. monococcum*, *T. polonicum*, *T. spelta*, *T. sphaerococcum*, *T. timopheevii*, *T. turanicum*, *T. turgidum*, *T. urartu*, *T. vavilovii*, *T. zhukovskyi* Faegi. Wheat plant also refers to species of the genera *Aegilops* and *Triticale*.

As used herein, the term "restorer of fertility of *T. timopheevii* CMS cytoplasm" refers to a protein whose expression in a wheat plant containing *T. timopheevii* CMS cytoplasm contributes to the restoration of the production of pollen.

New Gene Responsible for CMS

The inventors have discovered that the orf279 gene is responsible for CMS in wheat plants containing *T. timopheevii* cytoplasm. For clarity, this cytoplasm is herein referred to as T-CMS. It refers to any cytoplasm expressing orf279, a representative cytoplasm is the cytoplasm of *T. timopheevii*. For example, T-CMS can be present in wheat plant derived from *T. timopheevii*. T-CMS can also be a wheat plant from which *T. timopheevii* is derived, like *T. araraticum* the cultivated form of *T. timopheevii*.

The invention relates to the isolated nucleic acid encoding Orf279 protein of amino acid sequence at least 95% identical to SEQ ID NO: 4.

In a specific embodiment, the present invention relates to an isolated nucleic acid wherein the sequence is depicted in SEQ ID NO: 1.

As demonstrated in the example, orf279 results from a recombination event in the genome. The 5' part depicted in SEQ ID NO:2, corresponds to the 5'part of the gene encoding ATP synthase subunit 8 (the atp8 gene). On the contrary, the 3' part of orf279, depicted in SEQ ID NO: 3, is specific to this gene, and it is called in the present application "orf279-unique region".

The present invention also relates to a method for detecting orf279 DNA in wheat plant, seed or bulk of seeds, wherein the method comprises the step of extracting and isolating a DNA sample from a wheat plant and detecting orf279 DNA by specific means.

In a particular embodiment, the method for detecting orf279 DNA is performed in various lines or various varieties, more particularly in various wheat lines or varieties, for distinguishing the presence/absence of orf279 among different plants or varieties, and in particular among plants with CMS.

The presence of orf279 DNA means that the line or plant is harbouring a cytoplasm capable of inducing T-CMS. A line or plant harbouring such a cytoplasm may have a sterile phenotype or a fertile phenotype. In the latter case, such a fertile plant is likely to carry a functional restorer-of-fertility gene, "Rf".

On the contrary, the absence of orf279 DNA means that the line or plant cannot exhibit T-CMS.

This particular embodiment is especially interesting for use in research for screening the diversity of wheat cytoplasms and in seed production for screening the quality of the sterile female genotype in a hybrid wheat system. The detection of orf279 DNA can be of interest for the creation and increase of parent lines and in seed production for the maintenance of the A-line and for the hybrid production.

In another embodiment, such method is of interest for identifying orf279 DNA in recombinant mitochondrial DNA. Recombinant mitochondrial DNA is obtained after the transfer of mitochondria from one plant to another plant, these plants belonging to the same specie or to different species. Such transfer can be achieved by any method that results in mixing mitochondria from two plant parents (i.e., protoplast fusion, grafting or sexual crosses in case biparental inheritance can be achieved). In the present invention the transfer occurs from a plant characterized by a T-CMS cytoplasm to another plant without a T-CMS cytoplasm.

The term "sterile female genotype" means that the plant which has this genotype is certain to harbour a male sterile cytoplasm.

The present invention also relates to a method for detecting orf279 RNA in a wheat plant, seed or bulk of seeds, wherein the method comprises the step of extracting and isolating an RNA sample from the wheat plant and detecting orf279 RNA by specific means.

In particular, one mean for the detection of orf279 DNA, RNA, are markers recognizing the recombination junction between atp8 and the "orf279-unique region".

In another embodiment, means for detection are primers allowing the amplification of orf279 DNA, RNA. In particular, at least one of the primers hybridizes to the 3' part of orf279 depicted in SEQ ID NO:3, sequence specific to orf279.

In particular, the forward primer and the reverse primer to amplify the orf279 DNA, RNA are chosen among:
forward primers: SEQ ID NO: 12, SEQ ID NO: 6, SEQ ID NO: 10; and
reverse primers: SEQ ID NO: 7, SEQ ID NO: 11, SEQ ID NO: 9;
or are constituted by the forward primer SEQ ID NO: 8 and the reverse primer SEQ ID NO: 9.

In the present invention, the term DNA can include cDNA.

In a particular embodiment, the orf279 RNA expression level or pattern in a wheat line or plant can be quantified and compared to the orf279 RNA expression level and pattern of a reference plant material. The reference can be a sterile wheat line or a group of sterile wheat lines with a cytoplasm containing orf279 or a fertile line or a group of fertile plants. The fertile line can be either a maintainer line (considered as a negative control as it does not have a cytoplasm containing orf279) or a restored line with a cytoplasm containing orf279 and a nuclear genotype containing a restorer-of-fertility gene, Rf.

A similar level and pattern of orf279 RNA in the test plant compared to the sterile wheat line indicates that the plant is likely to present a CMS phenotype. A similar level and pattern of orf279 RNA in the test plant compared to a fertile wheat reference indicates that the plant is likely to present a fertile phenotype. As such, it is possible to screen or identify new Rf genes or assess the level of restoration of the fertility of the combination of different Rf genes in a genetic stack as described for example in WO2019086510.

Typically, but not limited to, the level of the orf279 RNA can be quantified with qRT-PCR or RNA-seq.

The present invention also relates to a method for detecting Orf279 protein in a wheat plant, seed or bulk of seeds, wherein the method comprises the step of extracting and isolating proteins and detecting Orf279 protein by specific means.

The means for detecting a protein in a protein extract are well-known by a person skilled in the art. In particular, Orf279 protein can be detected and quantified using immunological detection with an antibody directed towards an epitope located in the unique part of the Orf279 protein depicted in SEQ ID NO: 5. In particular, the detection of Orf279 protein is carried out by western blot, ELISA or immunostrip assay.

In a particular embodiment, the level or pattern of expression of Orf279 protein in a wheat line is quantified and compared to the level and pattern of Orf279 protein of a reference plant material. The reference can be a sterile wheat line or a group of sterile wheat lines with a cytoplasm containing orf279 or a fertile line or a group of fertile lines. The fertile line can be either a maintainer line (considered as a negative control as it does not have a cytoplasm containing orf279) or a restored line with a cytoplasm containing orf279 and a nuclear genotype containing a restorer-of-fertility gene, Rf.

A similar level and pattern of Orf279 protein in the test plant compared to the sterile wheat line indicates that the plant is likely to present a CMS phenotype. A similar level and pattern of Orf279 protein in the test plant compared to a fertile wheat reference indicates that the plant is likely to present a fertile phenotype.

Thus, the present invention also relates to a method for detecting orf279 DNA, orf279 RNA or Orf279 protein in a wheat plant, seed or bulk of seeds, wherein the method comprises the step of extracting a DNA or RNA or protein sample and detecting by means the orf279 DNA, orf279 RNA or Orf279 protein.

In a particular embodiment, said method comprises the steps of:
Detecting the sterile cytoplasm with a marker at the recombination junction between atp8 and SEQ ID NO:3, or within SEQ ID NO:3, or
Detecting the variation of orf279 expression in male sterile wheat plants.

The present invention also relates to means for Orf279 DNA, RNA or protein detection comprising:
a. molecular markers and primers recognizing orf279 recombination junction between atp8 and SEQ ID NO:3, such as the primers described above, or markers and primers recognizing SEQ ID NO:3; or
b. antibody recognizing Orf279, in particular an antibody directed towards an epitope located in SEQ ID NO:5.

The present invention also relates to a method for determining the sterility or fertility phenotype of a wheat plant, seed or bulk of seeds, comprising:
a step of extracting RNA and proteins
a step of detecting and quantifying orf279 RNA or Orf279 protein
a step of comparison of the orf279 RNA level (or pattern) or the Orf279 protein level (or pattern) with those quantified in sterile wheat lines containing orf279 and a fertile wheat line.

Means used for detecting and quantifying orf279 RNA and Orf279 protein are those previously described.

A similar level of orf279 RNA or Orf279 protein in a wheat plant compared to a sterile wheat line with a cytoplasm containing orf279 indicates that the plant will present a CMS phenotype.

This method allows the screening of diverse wheat cytoplasms or to screen the quality of sterile female genotype used in seed production in a hybrid wheat system.

The present invention also relates to a method for identifying a functional Rf gene encoding a protein able to bind to orf279 RNA, wherein said method comprises the steps of:
a. Predicting a target RNA sequence for protein encoded by each Rf gene identified in a wheat plant genome according to the PPR code.
b. Aligning each predicted target RNA sequence with SEQ ID NO:3
c. Identifying the Rf gene encoding for a protein able to bind to a target RNA sequence that shows at least 95% identity to SEQ ID NO:3.
d. Optionally optimizing the sequence of the selected Rf protein by changing amino acids at position 5 and 35 of selected PPR motifs to improve match according to the PPR code with SEQ ID NO:3.

At step a, all the possible ribonucleotides are determined for each amino acid combination at position 5 and 35, according to the PPR RNA binding code. The target RNA sequence scoring highest for RNA binding to the corresponding PPR is selected. The target RNA sequence is 5 to 50 bases long and preferentially 10 to 20 bases long.

At step b, the predicted target RNA sequence is aligned to the orf279-unique region depicted in SEQ ID NO:3. Alignment can be done over the full length or a fragment of SEQ ID NO:3. Such fragment can be 5 to 50 bases long and preferentially 10 to 20 bases long.

At step c the target RNA sequence has at least 95, 96, 97, 98, 99 or 100% identity with SEQ ID NO:3 over the aligned region.

In a particular embodiment, the method comprises a step e corresponding to the validation of the binding to orf279 RNA, wherein a plant with T-CMS cytoplasm is transformed with a vector expressing the Rf protein candidate, and fertility restoration is analyzed by phenotyping and/or by analyzing orf279 expression.

An alternative method for screening for a functional Rf gene encoding for a PPR protein able to bind to orf279 RNA, comprises the steps of:
 a. Transforming a wheat plant with an expression cassette comprising a candidate Rf gene wherein said wheat plant has a sterile cytoplasm expressing the Orf279 protein.
 b. Detecting the level and pattern of orf279 expression in the transformed plant.
 c. Selecting the plant wherein the level or pattern of orf279 expression is altered compared to the non-transformed plant.
 d. Identifying the functional Rf gene.

Transformation methods of a wheat plant are well-known by the person skilled in the art. For example, it can be carried out using an *Agrobacterium tumefaciens*-mediated approach or a biolistic approach.

In this method, Rf candidate genes, are screened for their capacity to alter the orf279 RNA or Orf279 protein level or pattern compared to a wheat line with a sterile cytoplasm expressing orf279. An alteration can be a decrease of the RNA or protein level in one or more tissues of the plant.

Rf candidate genes able to restore fertility are selected.

Another aspect of the present invention relates to a method for the design and optimization of a synthetic PPR protein capable of binding orf279 RNA, and preventing its expression, whereby said synthetic PPR protein restores fertility.

According to the present invention, the expression "preventing expression of orf279 RNA" means induction of RNA cleavage, RNA degradation, or inhibition of translation.

In a particular embodiment, this method comprises the steps:
 a. Identifying a target RNA sequence of interest in SEQ ID NO:3, said target RNA sequence is 5 to 50 bases long and preferentially 10 to 20 bases long.
 b. assigning to each target RNA base selected from the group comprising adenine (A), guanine (G), cytosine (C), and uracil (U), a pair of amino acids according to the PPR RNA binding code
 c. designing a synthetic PPR sequence comprising PPR RNA binding motifs (each containing an amino acid pair defined in step b) capable of binding the target RNA sequence.

In another particular embodiment, this method comprises the optimization of a candidate Rf protein able to restore the cytoplasmic fertility, more particularly identified as previously described or as described in example C. This optimization aims to improve binding of the Rf protein to the orf279 RNA.

In a particular embodiment, the optimization is carried out as described in FIG. 5. The amino acids at positions 5 and 35 of each motif of the PPR are listed, indicating the number of the motif, and indicating below the RNA sequence. Amino acids at position 5 and/or 35 that do not make a perfect match with the RNA binding site according to the PPR code are changed according to this code in order to improve the binding to the RNA sequence.

The PPR code is described in the international application WO2013/155555A1.

The present invention also concerns synthetic PPR proteins capable of binding orf279 RNA obtained from the method above.

In a particular embodiment, a PPR protein capable of binding orf279 RNA is depicted in SEQ ID NO: 22.

In particular, a synthetic PPR protein capable of binding orf279 RNA, preventing expression of orf279 and thus restoring fertility.

The restoration of fertility can be easily checked by introducing a vector expressing the synthetic PPR into a wheat plant with T-CMS cytoplasm, and then proceeding to fertility restoration phenotyping assays as described in the example, part B.

In another aspect, the present invention relates to a method for obtaining a fertile wheat plant by transforming said plant with a vector expressing a synthetic PPR binding orf279 and preventing its expression. The vector comprises a recombinant expression cassette comprising a nucleic acid sequence encoding the synthetic PPR, downstream of a promoter functional in plants.

In a specific embodiment, such method also comprises transforming said plant with a vector expressing a PPR binding orf256.

The present invention also concerns a plant expressing a synthetic PPR binding orf279 obtained as previously described. Such a plant is therefore of fertile phenotype.

The term "promoter" as used herein refers to a region of DNA upstream of the coding sequence (upstream of start codon) and including DNA regions for recognition and binding of RNA polymerase and other proteins to initiate transcription before the start codon. Examples of constitutive promoters useful for expression include the 35S promoter or the 19S promoter (Kay et al, 1987), the rice actin promoter (McElroy et al, 1990), the pCRV promoter (Depigny-This et al, 1992), the CsVMV promoter (Verdaguer et al. 1996), the ubiquitin 1 promoter of maize (Christensen and Quail, 1996), the regulatory sequences of the T-DNA of *Agrobacterium tumefaciens*, including those from the genes encoding mannopine synthase, nopaline synthase, octopine synthase.

Promoters may be "tissue-preferred", i.e. initiating transcription in certain tissues or "tissue-specific", i.e. initiating transcription only in certain tissues. Examples of such promoters are DHN12, LTR1, LTP1 specific for the embryo, SS1 specific for the phloem, OSG6B specific for the tapetum (Gotz et al 2011 and Jones 2015).

Other suitable promoters could be used. It could be an inducible promoter, or a developmentally regulated promoter. An "inducible" promoter initiates transcription under some environmental control or can be stress-induced, like for example the abiotic stress-induced RD29, COR14b (Gotz et al, 2011).

Typically, the promoter is functional in the nucleus.

Constitutive promoters may be used, such as the ZmUbi promoter, typically the ZmUbi promoter of SEQ ID NO:16, or the promoter CaMV35S. Finally, the promoters of SEQ ID NO:26, SEQ ID NO:27 and SEQ ID NO:28 corresponding to pTaRFL46, 79 and 104 can also be used.

In particular, constitutive promoters used in the present application are: proZmUBI_intUBI depicted in SEQ ID NO:14, proOsActin_intOsActin, proVirCsVMV, proVir35S, pro35S_intZmUBI.

Another aspect of the invention concerns a recombinant expression cassette comprising the nucleic acid sequence encoding for Orf279 of SEQ ID NO:1, downstream of a promoter functional in plants and a sequence encoding a mitochondrial transit peptide.

The mitochondrial transit peptide allows to address the peptide to the mitochondria. Huang et al. (2009) describes the main characteristics of plant mitochondrial transit peptides.

In particular, the mitochondrial transit peptide is a sequence from *Oryza sativa*, and more particularly it corresponds to OsPPR_02g02020 depicted in SEQ ID NO: 19, or Os01g49190 depicted in SEQ ID NO: 20.

Such a recombinant cassette can be used for transforming a plant. Thus, the present invention also relates to a plant expressing a recombinant expression cassette comprising the nucleic acid sequence encoding for Orf279 downstream of a promoter functional in plants and a mitochondrial transit peptide.

In a particular embodiment, said plant is wheat.

The present invention also relates to a method for obtaining a sterile plant by transforming said plant with a recombinant expression cassette comprising the nucleic acid sequence encoding for Orf279 downstream of a promoter functional in plants and a mitochondrial transit peptide.

In a particular embodiment, said plant is also transformed with recombinant expression cassette comprising the nucleic acid sequence encoding for Orf256 downstream of a promoter functional in plants and a mitochondrial transit peptide. In a more particular embodiment, said plant is wheat.

In order to obtain a fertile plant, in particular a wheat plant, from a plant having a cytoplasmic male sterility and having the gene orf279, it is possible to use known means allowing to decrease the transcription of the gene and/or the translation of the orf279 RNA.

In another aspect, the present invention concerns a method for obtaining a fertile wheat plant by transforming said plant with a recombinant expression cassette comprising a gene (or genes) encoding an orf279 DNA/RNA binding or editing complex, said orf279 DNA/RNA binding or editing gene is cloned downstream of a promoter functional in plants and a mitochondrial transit peptide.

The orf279 DNA/RNA binding or editing complex is a DNA or RNA editing tool which is able to either (1) disrupt the orf279 gene directly in the mitochondrial genome or (2) to reduce expression of the orf279 transcript.

Known genome editing tools can be used to target the corresponding orf279 gene within the wheat plant nuclear and mitochondrial genomes by deletion, insertion or partial or total allele replacement at the corresponding locus. Such genome editing tools include without limitation targeted sequence modification provided by double-strand break technologies such as, but not limited to, meganucleases, zing finger nuclease, TALENs (WO2011072246) or CRISPR CAS system, including CRISPR Cas9 (WO2013181440) and CRISPR Cas13a, Cpf1 or their next generations based on double-strand break technologies using engineered nucleases. An RNA editing factor could be designed and used to introduce premature translation termination by introduction of a STOP codon in the coding sequence of orf279 transcripts in wheat mitochondria.

In another aspect, the present invention concerns a method for detecting sterile plants harbouring a orf279 T-CMS cytoplasm or fertile plants harbouring a normal cytoplasm wherein the method comprises the steps of:
a) extracting a DNA or RNA sample from the plants
b) detecting the presence or absence of orf279 T-CMS sequence by PCR amplification with suitable pair of primers, and optionally, detecting the presence or absence of normal cytoplasm sequence by PCR amplification with suitable pair of primers.
c) determining the fertile or sterile status of the plants.

Suitable pair of primer for amplifying orf279 T-CMS can be for example the pair of primers SEQ ID NO: 52 and 54, or variant thereof. Other suitable pair of primers can be obtained by using a forward primer selected from the sequence SEQ ID NO: 12, SEQ ID NO: 6, SEQ ID NO: 10 or SEQ ID NO: 8, and a reverse primer selected from the sequence SEQ ID NO: 7, SEQ ID NO: 11 or SEQ ID NO: 9, preferably by using the pair of primers obtained with forward primer SEQ ID NO: 8 and reverse primer SEQ ID NO: 9.

Suitable pair of primer for amplifying normal cytoplasm sequence can be for example the pair of primers SEQ ID NO: 53 and 54, or variant thereof.

Step c) of determining the fertile or sterile plant status can be performed by detecting the presence or absence of a PCR amplification signal. Particularly, sterile status depends on the presence of an amplification signal using specific primers capable of amplifying of orf279 T-CMS sequence, while fertile status is determined by the absence of said amplification signal.

Optionally, a step of amplifying normal cytoplasm sequence with suitable pair of primers can be performed as positive control to confirm the fertile plant status.

Of course, the skilled person may use variant primers as identified above, said variant primers or nucleic acid probes having at least 90%, and preferably 95% sequence identity with any one of the primers as identified above.

Percentage of sequence identity as used herein is determined by calculating the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. For example, nucleic acid sequences may be aligned using the BLAST 2 sequences (Bl2seq) using BLASTN algorithms (www.ncbi.nlm.nih.gov).

In a further aspect, the present invention concerns a diagnostic marker for determining the presence or absence of orf279 comprising the pair of primers SEQ ID NO: 52 and 54 to amplify orf279 T-CMS sequence and, optionally, the pair of primers SEQ ID NO: 53 and 54 to amplify the normal cytoplasm sequence.

The orf279 diagnostic marker to follow the presence of the *T. timophevii* cytoplasm during the creation or conversion and increase of parent lines and the hybrid production can be used for the following activities:
Breeding schemes for parental lines creation:
Conversions by back-cross of the *T. timophevii* cytoplasm in A lines and R lines, if the restorer is alloplasmic, meaning if the R line carries the T-CMS cytoplasm. Control of Orf279 presence in single seeds, bulk of seeds or plants
Creation of R lines by DH, SSD, pedigree breeding or any other breeding scheme, if the restorer is alloplasmic, meaning if the R line carries the T-CMS cytoplasm. Control of Orf279 presence in single seeds, bulk of seeds or plants Production for research of commercial purposes
Control of single seeds, bulks of seeds or plants of the A line, for maintenance, hybrid production or DUS assessment
Control of single seeds, bulks of seeds or plants of the R line if the restorer is alloplasmic, meaning if the R line carries the T-CMS cytoplasm
Control of single seeds, bulk of seeds or plants of T-CMS hybrids. The marker allows to measure the contamination by non alloplasmic grains (any wheat line on wheat cytoplasm) within the hybrid lots. This can be used to control the purity and hybridity levels of hybrid seed lots.
Control of F1 seed lots sent for DUS trials and official trials. The marker allows to verify if the hybrid is alloplasmic, an essential step to ensure fertility of the hybrid.

FIGURES

Figure 1B:
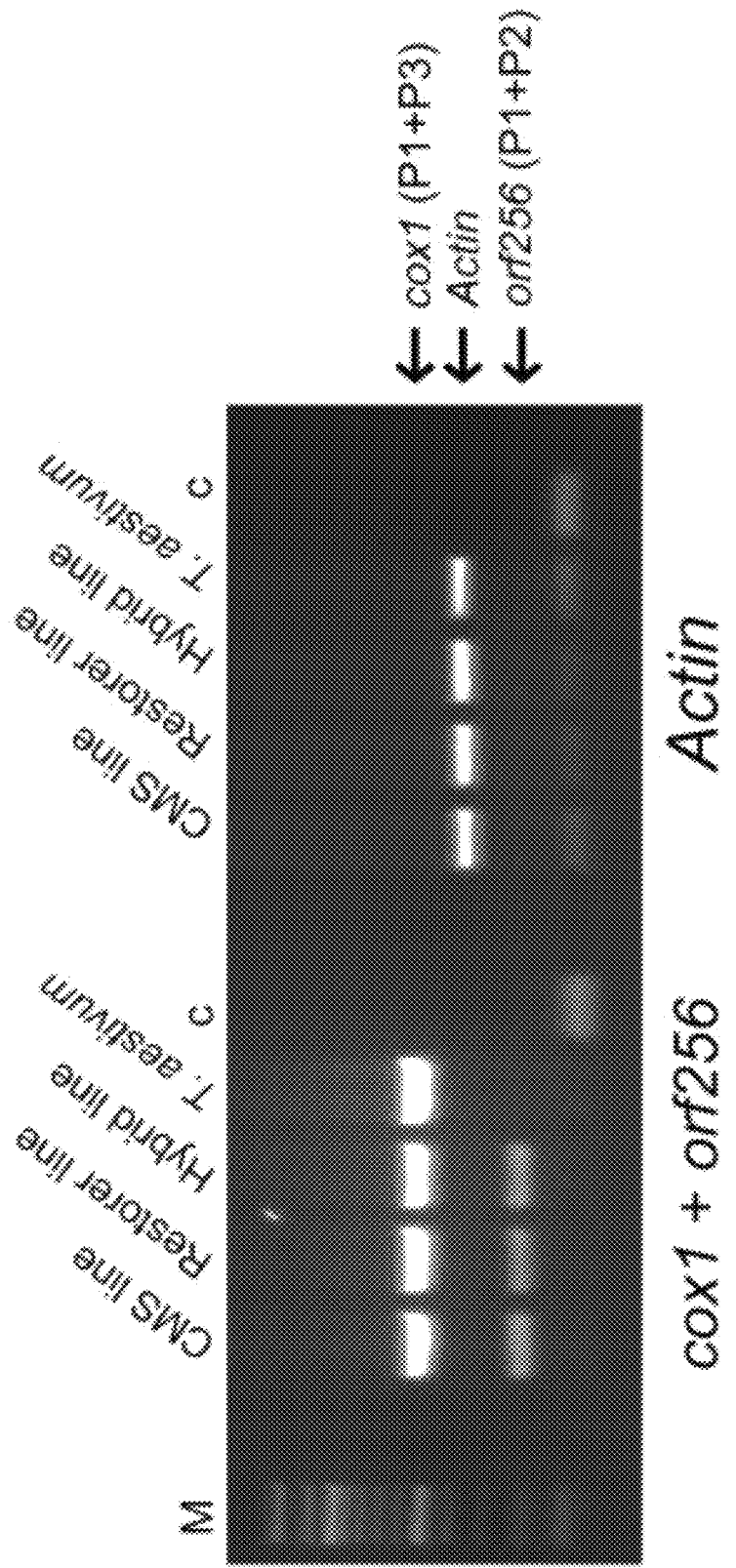
Figure 1C:
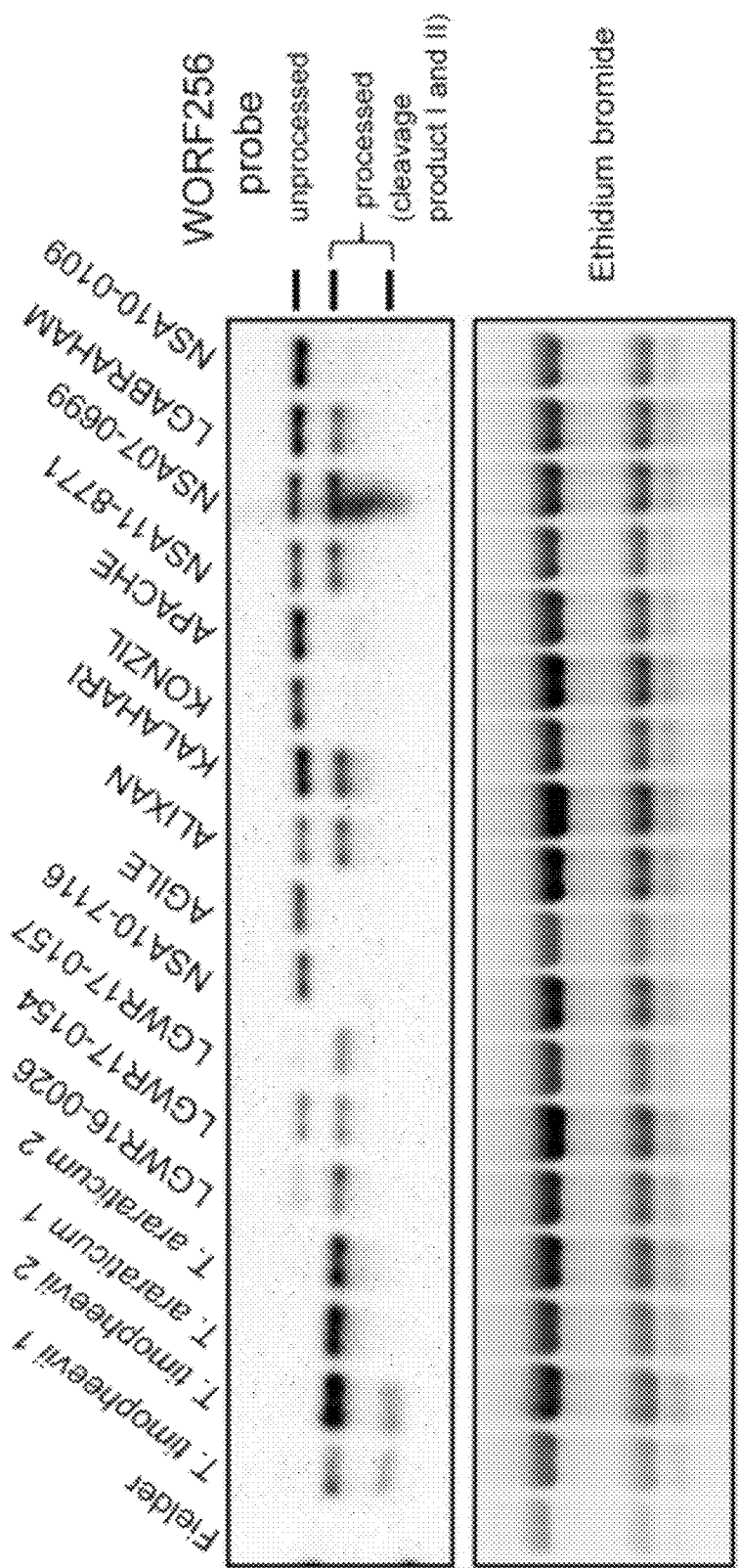
Figure 1D:
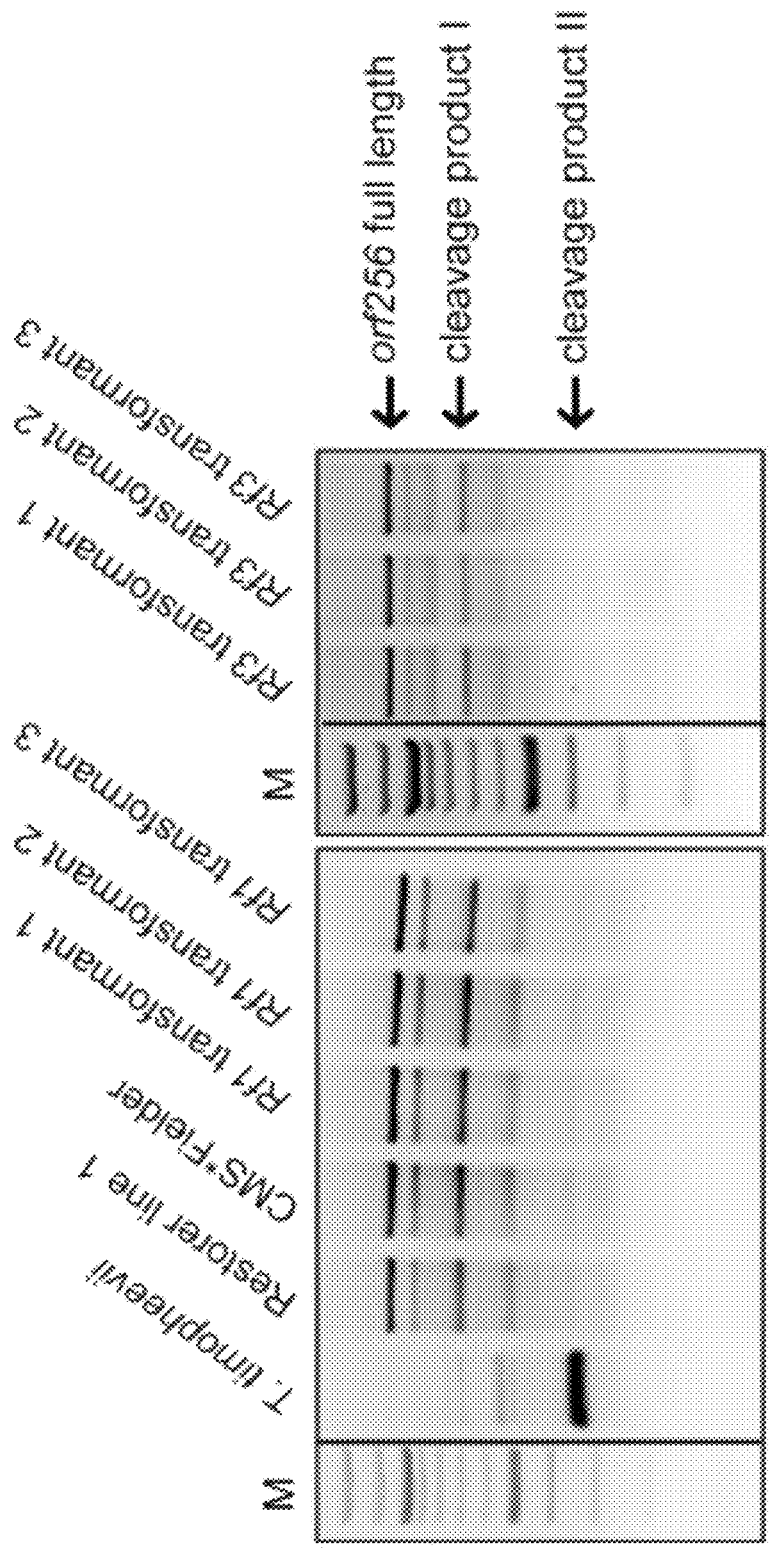

FIGS. 1A-1D. Expression of orf256 is unaltered by Rf1 and Rf3. FIG. 1A. Schematic overview of the orf256 genomic structure. Binding sites of primers P1-P3 used in the RT-PCR analysis are indicated. FIG. 1B. RT-PCR analysis of the expression of orf256 in different wheat genotypes. M—100 bp ladder, c—water control. Actin was used as an internal reference control. FIG. 1C. Survey of several T-CMS accessions in regard to orf256 processing by Northern blot including six wheat varieties. The WORF256 probe used to detect orf256 was prepared as described previously (Song et al., 1994). FIG. 1D. Mapping of the 5'-ends of orf256 RNA species by 5'-RACE approach. GSP2—Gene specific primer 2. M—100 bp ladder.

Figure 2C:
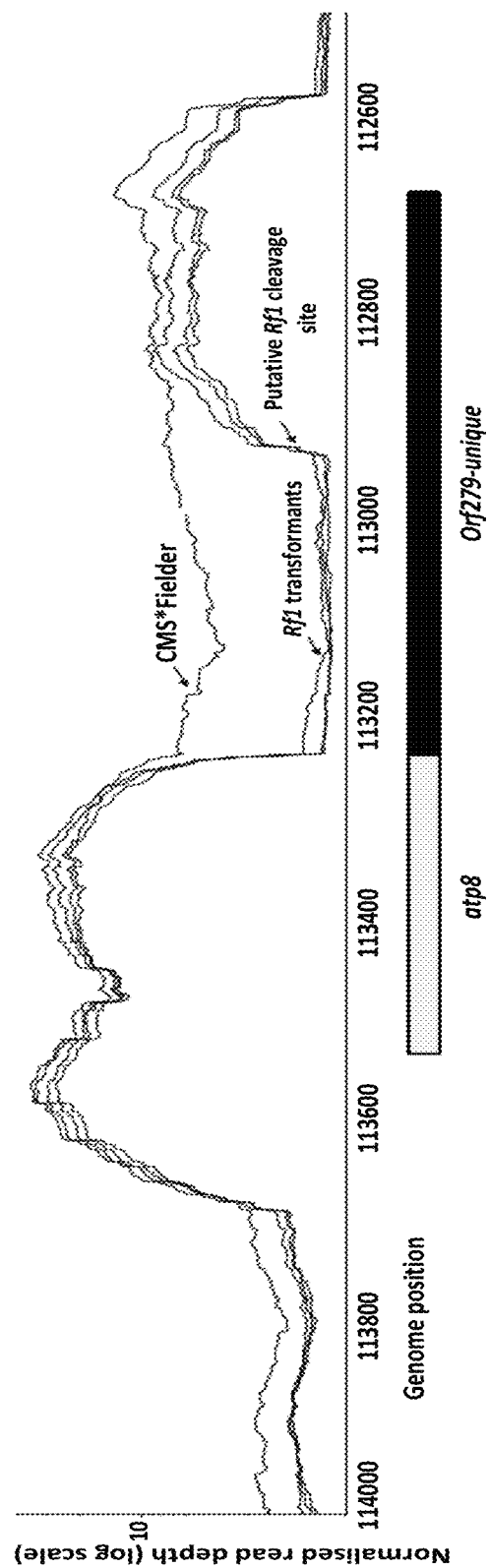

FIGS. 2A-2C. Identification of orf279 as a novel RNA associated with T-CMS in wheat. FIGS. 2A-B. Ratio of strand-specific RNA-seq coverage from sterile and restored (Rf1) samples plotted across the mitochondrial genome. RNA-seq coverage of orf279 (FIG. 2B) is much higher in sterile plants whereas coverage of orf256 (FIG. 2A) is similar in both. FIG. 2C. Normalised RNA-seq coverage in the orf279 region. orf279 is indicated by the boxes below the chart, distinguishing the part of orf279 that is identical to atp8 and the orf279-unique region. The number of RNA-seq reads mapped to the central region of orf279 in Rf1 transformants is much lower than in BGA CMS*Fielder. The sharp transition from low to high coverage indicates the probable site of RNA cleavage induced by Rf1.

FIG. 3. Orf279 as genetic basis of cytoplasmic male sterility in wheat T-CMS plants. A. Schematic drawing of orf279. The first 97 amino acid residues at the N-terminus of Orf279 correspond to ATP synthase subunit 8 encoded by the mitochondrial atp8 gene. B. 5'-RACE analysis of orf279 transcripts. Arrows indicating Rf1 and Rf3 specific cleavage products, respectively, are shown. The binding site of GSP1—Gene specific primer 1 is indicated in panel A. M—100 bp ladder.

FIG. 4: Design of the Synthetic Restorer for orf279 (SRorf279) and Synthetic Restorer for orf256 (SRorf256). Amino acids at position 5 and 35 of each PPR motif were extracted and aligned with an RNA base predicted following the "PPR code" (Barkan et al., 2012). Amino-acid modified during optimization of SRorf279 and SRorf256 proteins are indicated.

FIG. 5: Location of PCR primers on orf279 sequence: primer PP_03004_ORF279-amont-cliv_3_F (SEQ ID NO:6), primer PP_03004_ORF279-amont-cliv_3_R (SEQ ID NO:7), primer PP_03006_ORF279-aval-cliv_4_F (SEQ ID NO:8), primer PP_03006_ORF279-aval-cliv_4_R (SEQ ID NO:9), primer PP_03007_ORF279-cliv_F (SEQ ID NO:10), SEQ ID NO:10 (SEQ ID NO:11), primer PP_03003_atp8_4_F (SEQ ID NO:12), primer PP_03003_atp8_4_R (SEQ ID NO:13).

Figures 6, 7:
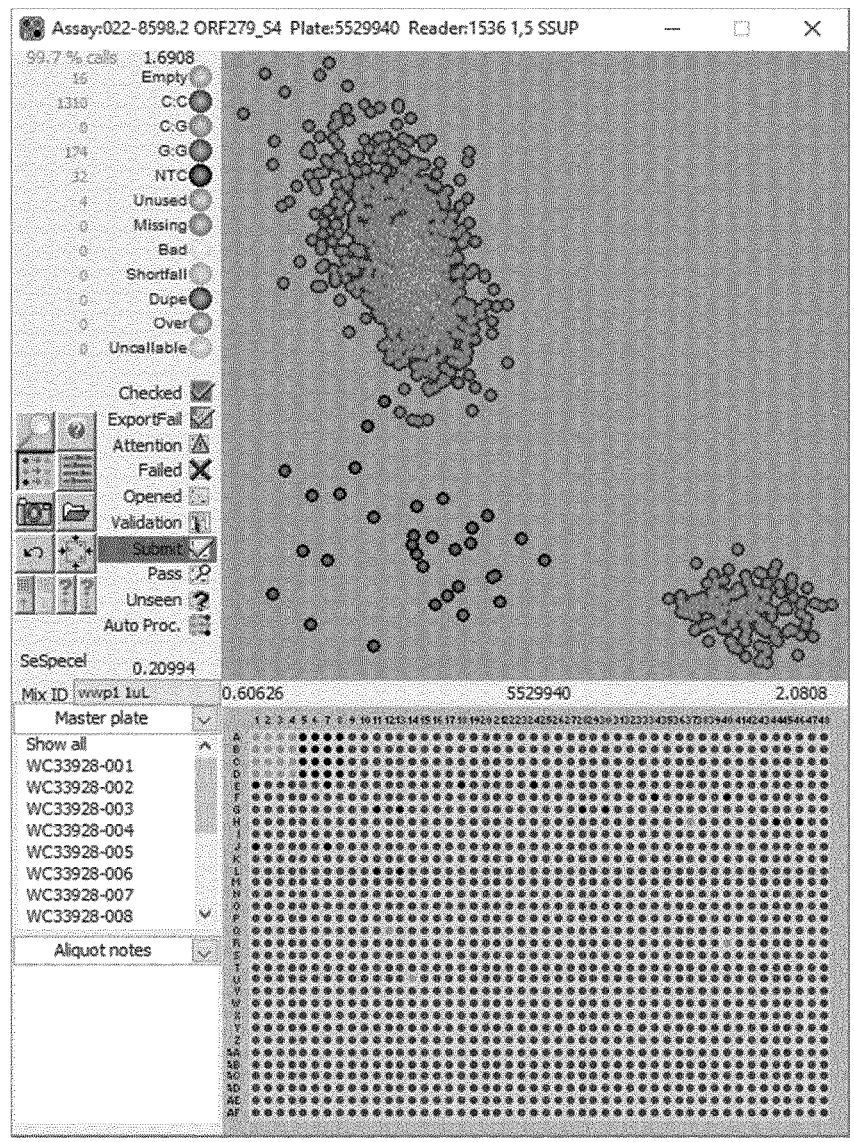

FIG. 6: Design of two optimized RFL29a proteins. Amino acids at position 5 and 35 of each PPR motif were extracted and aligned with an RNA base predicted following the "PPR code" (Barkan et al., 2012). Amino acids modified during optimization of RFL29a protein are indicated.

FIG. 7: PCR amplification results. Right cluster: amplification of the normal cytoplasm with oligonucleotide AS2 in fertile plants. Left cluster: amplification of the orf279 with oligonucleotide AS1 in sterile plants.

EXAMPLES

A—Production and Phenotyping of Rf1 and Rf3 Transformants

Fine mapping of the genomic regions harbouring Rf1 and Rf3 restorer genes in wheat was performed and Rf1 genes present in the Rf1 and Rf3 interval in the IWGSC RefSeqv1.0 reference genome were identified. In parallel, Rf1 genes present in *Triticum timopheevii* and wheat Rf1, Rf3 or maintainer accessions were enriched and sequenced by targeted Rf1 capture. Both mapping and capture analysis allowed to predict candidate Rf1 and Rf3 restorer genes. Restoring capabilities of Rf1 and Rf3 candidate genes were assessed by transgenic approaches.

The nucleic acid encoding TaRFL79 protein of amino acid sequence depicted in SEQ ID NO: 15, was identified as the Rf1 restorer gene. The nucleic acid encoding TaRFL29a protein of amino acid sequence depicted in SEQ ID NO: 25 was identified as the Rf3 restorer gene. Each were separately adapted and cloned via a Golden Gate reaction into the destination binary plasmid pBIOS10746.

The following expression elements were used for each construct: the constitutive *Zea mays* ubiquitin promoter (proZmUbi depicted in SEQ ID NO: 16) associated with the *Zea mays* ubiquitin intron (intZmUbi, depicted in SEQ ID NO: 17 Christensen et al 1992) and a 3' termination sequence of the gene encoding a sorghum heat shock protein, terSbHSP (accession number: Sb03g006880), depicted in SEQ ID NO: 18.

The recombinant constructs of TaRFL79 and TaRFL29a are respectively depicted in SEQ ID NO: 29 and SEQ ID NO: 30.

All the binary plasmids described above were transformed into *Agrobacterium* EHA105 strain. BGA CMS*Fielder wheat as well as conventional Fielder cultivar were transformed with those *Agrobacterium* strains as described by WO2000/063398. Wheat transgenic events were generated for each of the constructs.

BGA CMS*Fielder is a Fielder maintainer line carrying T-CMS cytoplasm. This line was constructed in order to combine both sterility high transformation efficiency and tissue regeneration. The BGA CMS*Fielder plants are sterile.

Fertility restoration phenotyping assays were performed on the different events as following. All wheat transgenic plants generated above and control fertile plants were grown in a glasshouse under standard wheat growth conditions (16 h of light period at 20° C. and 8 h of dark period at 15° C. with constant 60% humidity) until control grains of the wild type Fielder cultivar reached maturity stage.

Fertility of the transgenic plants was evaluated by counting the number of seeds and empty glumes per spike on each plant and comparing with the wild type Fielder and BGA CMS*Fielder control plants. Plants were also evaluated by observing anther extrusion.

16 transformed CMS-Fielder plants overexpressing the TaRFL79 sequence under the ZmUbi promoter derived from 11 independent transformation events and 36 transformed CMS-Fielder plants overexpressing the TaRFL29a sequence under the ZmUbi promoter derived from 19 independent transformation events were analyzed.

100% to 92% respectively of the analyzed plants present restoration of male fertility while 100% of untransformed CMS-Fielder plants grown in parallel are fully sterile with no anther extrusion and no seed produced, and 100% of WT-Fielder plants are fertile.

B—Molecular Characterization of the Rf1 and Rf3 Transformants
1—Material and Method
RNA Analyses RNA was extracted from the plants with the RNeasy Plant Mini kit (Qiagen) according to manufacturer's instructions. For transgene expression analyses cDNA was synthesized with SuperScript™ III Reverse Transcriptase (Invitrogen) kit and the amplification was performed with primers P1, P2 and P3 listed in table 1.

TABLE 1 sequence of the different primers used in the present analysis

| Primer Name | Sequence 5'->3' | SEQ ID NO |
|---|---|---|
| GSP1 | GGA TTT GCC CGC AAA TGG TTG ATC | 31 |
| GSP2 | GAT TAC GCC AAG CTT AAG AAT CAG AAT TAC TGA GCT ACC CCG CTC TT | 32 |
| P1 | ATGACAAATATGGTTCGATGGC | 33 |
| P2 | GCTTGGGGATCCTGAATC | 34 |
| P3 | GCTGTCACTAGAACGGACC | 35 |
| Ta_Actin_F | GCCACACTGTTCCAATCTATGA | 36 |
| Ta_Actin_R | TGATGGAATTGTATGTCGCTTC | 37 |
| WORF256_211_806_for | ATCCCCAAGCTCTAGCTCATTTAG | 38 |
| WORF256_211_806_rev | GGGGGCTGGAAGAGAAAAGAAT | 39 |

Northern Blot 5-10 μg of total RNA was separated on 1.2% denaturing agarose gel and transferred onto Hybond N+ membrane (Amersham). Northern blotting was performed overnight in 10×SSC (1.5 M sodium chloride and 150 mM trisodium citrate pH 7.0) buffer. The membrane was pre-hybridised in PerfectHyb™ Plus Hybridization Buffer (Sigma) for 2 hrs at 65° C. The biotin-labelled probes were hybridized overnight in hybridization buffer. After 3 washing steps with wash solution containing decreasing concentration of the SSC buffer supplemented with SDS the probe signal was detected using the Chemiluminescent Nucleic Acid Detection Module Kit (ThermoFisher) and ImageQuant™ imager (GE Healthcare). For probe synthesis of Actin and orf256 RNA, the DNA fragment was amplified with primers given in table 1. The reaction products were cloned into the pGEM®-T Easy (Promega) vector and confirmed by PCR and sequencing at Macrogen (Macrogen, South Korea). The RNA probe was synthesized with the MAXIscript™ SP6/T7 Transcription Kit (Ambion) and the pGEM®-T Easy plasmid as a template and biotin labeled analog of cytidine triphosphate (CTP) (Roche).

Rapid Amplification of cDNA Ends (5'-RACE)

1 μg of total RNA was used for cDNA synthesis and amplification of 5' ends using the SMARTER@RACE 5'3' Kit following manufacturer's instructions (Takara). PCR products were gel purified, cloned into pGEM®T Easy (Promega) and sequenced at Macrogen (Macrogen). Gene specific primer sequences (GSP1 for orf279 and GPS2 for orf256) are given in table 1.

Mitochondrial DNA Sequencing and Assembly

The extraction of mitochondrial DNA was preceded by enrichment of mitochondrial fractions from seven-day-old wheat coleoptiles grown on vermiculite in a growth cabinet at 22° C. in darkness. For mitochondrial isolation and DNA extraction previously described protocols were adapted (Huang et al., 2004, Triboush et al., 1998). The obtained DNA (50 ng) was ultrasonicated to 550 bp fragments with a Covaris S220 focused ultrasonicator (Covaris, USA). The libraries were prepared with the TruSeq® Nano DNA LT Sample Preparation Kit—Set A (Illumina, USA). The normalized and pooled libraries were used for sequencing on a MiSeq desktop sequencer (Illumina, USA) with the MiSeq® Reagent Kit v3 (600 cycles) (Illumina, USA). Overlapping paired-end reads were merged using the software FLASH [version 1.2.7] and merged reads were assembled using Velvet [version 1.2.08], with a k-mer value of 91 and a coverage cut-off of 20. To identify ORFs unique to the *T. timopheevii* mitochondrial genome, reads from the T-CMS line were mapped to the *T. aestivum* mitochondrial genome reference (DNA Database accession no. AP008982, Ogihara et al., 2005) to filter out the reads that are common to both *T. timopheevii* and *T. aestivum* genomes. The remaining unmapped reads were re-assembled into contigs with Geneious software (www.geneious.com/).

RNAseq Analysis of BGA CMS*Fielder and Rf1 and Rf3 Transformants

RNA was extracted from BGA CMS*Fielder and Rf1 transformants using the RNAeasy Plant Mini Kit (Qiagen) and its quality was estimated on an Agilent 4200 tape station (Agilent). 3 μg of total RNA was sent to Macrogen for NGS sequencing. The libraries were performed with the TruSeq Stranded Total RNA Ribo Zero Samples Prep Kit (Illumina) and sequenced on a Hiseq4000 platform (Illumina) with 100 bp paired-end sequencing kit (Illumina). Reads were adapter-trimmed and mapped to the *T. timopheevii* mitochondrial genome (NC_022714) with BBMap (Bushnell B. sourceforge.net/projects/bbmap/). Multimapped reads were distributed randomly between the best-matching sites and rRNA regions were masked (because rRNA depletion was inconsistent across samples). Regions identical to plastid DNA were masked to avoid cross-mapped plastid reads and read depth was normalized by dividing by mean coverage depth excluding the masked regions.

2—Results
a—Processing of Orf256 does not Correlate with Fertility Restoration in T-CMS Wheat A previous study indicated that fertility restoration of T-CMS plants is correlated with the expression of Orf256 protein (Song and Hedgcoth, 1994A) and that the nuclear background influenced the level of the orf256 transcript in wheat accessions (Song et al., 1994B). To analyse the expression and processing pattern of orf256 in wheat genotypes carrying either *T. aestivum* or *T. timopheevii* cytoplasm and with different restoring capabilities, total RNA was extracted and RT-PCR as well as northern blot analysis with an orf256-specific probe was performed (FIGS. 1A-1D). The RT-PCR results show that orf256 RNA is quite abundant across plant accessions and levels are independent of the presence of a restorer gene (FIG. 1A). The northern blot results revealed that the processing of orf256 did not correlate with the restoration of fertility phenotype as even in wheat lines known not to carry a restorer gene, a processing of orf256 RNA was observed (FIG. 1C). Indeed, several lines including Alixan, Kalahari, Lgabraham known to not carry a restorer gene show processing of orf256 at cleavage site I as compared to lines *T. timopheevii* or LGWR16-0026, LGWR17-0154 and LGWR17-0157 known for carrying restorer genes.

To analyze the processing of orf256 in the different genotypes as well as in the Rf1 and Rf3 transformants in more detail, Rapid Amplification of cDNA Ends (5'-RACE) was performed (FIG. 1D). Cleavage of orf256 is observed in *T. timopheevii* and in T-CMS plants with a maintainer genotype BGA CMS*Fielder plants (FIG. 1D). In addition, a second cleavage site in orf256 was found only in *T. timopheevii* in agreement with the northern blot result (FIG. 1C).

b—Identification of Orf279 as the Genetic Basis of CMS in T-CMS Wheat

As the processing/cleavage of orf256 in T-CMS mitochondria does not correlate with the presence of either Rf1 or Rf3 restorers, the *T. timopheevii* mitochondrial DNA was extracted and sequenced to look for the presence of other chimeric orfs that could be the molecular basis for CMS in *T. timopheevii*. Mitochondrial DNA was sequenced on Illumina MiSeq platform and 17 contigs present in *T. timopheevii* and absent in the *T. aestivum* mitochondrial genome were identified (Table 2). 25 candidate ORFs corresponding to the best ORFs identified between two STOP codons and encoding peptides longer than 100 amino acids were identified (Table 2). Orf256 was found to be encoded within contig 11 as ORF5 (Table 2). The remaining uncharacterised 24 ORFs were screened for regions homologous to other genes from the *T. timopheevii* mitochondrial genome or other sequenced plant genomes by using blastn (https://blast.ncbi.nlm.nih.gov/) (Table 2). The searches revealed that two ORFs were already identified to be encoded by the mitochondrial genomes of *Oryza sativa* (contig 1, orf27=orf194) and *Zea mays* (contig 5, orf21=orf296), respectively. Subsequent RNAseq analysis of RNA samples from BGA CMS*Fielder as well as Rf1 and Rf3 transformants revealed that the biggest proportional reduction in expression was observed within the 1.1 kb region of contig_4_orf13 (FIGS. 2A and B). This region was found to encode a protein composed of 279 amino acids and thus was named orf279. In the Rf1 and Rf3 transformants, the orf279 transcript is cleaved; the 5' end is degraded (preventing translation) but the 3' end persists (FIG. 2C). Most of the reads mapping to the 5' region of the ORF and upstream are probably from the other (complete) copy of atp8 present in the mitochondrial genome (FIG. 2C).

TABLE 2

List of contigs and ORFs found as present in the *T. timopheevii* mitochondrial genome and absent in *T. aestivum* genome.

| Contig No. | length | Location in the mitochondrial genome from | too | in close proximity to | no. of reads assembled | no. of identified ORFs within the contig | best orf |
|---|---|---|---|---|---|---|---|
| 1 | 6 036 | 438 186 | 443 419 | 1476 bp upstream of CobA | 3 626 | 52 | ORF 27 (frame 1) |
| 2 | 7 053 | 205 909 | 212977 | 1173 bp upstream of atp8 | 30 739 | 70 | ORF 21 (frame 2) |
| 3 | 4 901 | 23 198 | 28114 | downstream of cox1 | 14 927 | 45 | ORF 1 (frame 2) ORF 7 (frame 1) ORF 16 (frame 1) |
| 4 | 3 044 | 110 864 | 113 743 | encompasses p-gene atp8 | 11 839 | 23 | ORF 13 (frame 3) |
| 5 | 3 495 | 295 117 | 315 783 | 1760 bp upstream of trnF | 10 524 | 31 | ORF 19 (frame 2) ORF 21 (frame 1) |
| 6 | 1 920 | 248 389 | 250 306 | between orf-240 and p-ccmC | 9 389 | 17 | ORF 10 (frame 3) |
| 7 | 3 239 | 155 448 | 158 643 | encompasses C-terminus of CobB | 8 448 | 29 | ORF 22 (frame 1) ORF 24 (frame 3) ORF 19 (frame 3) |
| 8 | 2 145 | 171 240 | 174 141 | between 236 bp-p-rpl16 and 573 bp-p-orf256 | 8 344 | 23 | ORF 2 (frame 1) |
| 9 | 2 297 | 430 951 | 433 248 | 1478 downstream of cobA | 7 406 | 16 | ORF 10 (frame 3) |
| 10 | 2 378 | 152 704 | 154 048 | 260 bp downstream of atp9 | 6 255 | 21 | ORF 11 (frame 2) |
| 11 | 1 982 | 22 510 | 23 949 | upstream of cox1 | 5 545 | 9 | ORF 5 (frame 3) ORF 9 (frame 3) |
| 12 | 1 810 | 15 652 | 16 704 | 3,106 bp upstream of orf256 | 4 959 | 17 | ORF 1 (frame 1) |
| 13 | 1 531 | 15 652 | 16 704 | downstream of rps7 | 4 185 | 16 | ORF 14 (frame 3) |
| 14 | 1 911 | 132 568 | 134 477 | 2306 bp dpwnstream of rpl16 | 4 120 | 18 | ORF 10 (frame 1) |
| 15 | 1 748 | 165 189 | 166 960 | 1123 bp upstream of rps3 exon 1 | 3 940 | 20 | ORF 15 (frame 2) ORF 8 (frame 2) |

TABLE 2-continued

List of contigs and ORFs found as present in the T. timopheevii
mitochondrial genome and absent in T. aestivum genome.

| | | | | | | | | |
|---|---|---|---|---|---|---|---|---|
| 16 | 1 409 | 221 333 | 222 752 | 2022 upstream of rpl5 | | 3 836 | 14 | ORF 11 (frame 3) ORF 5 (frame 3) |
| 17 | 1 320 | 172 302 | 172 622 | encompasses p-rpl16 (R8) and rps2 (R7) | | 1 773 | 12 | ORF 2 (frame 2) |

| Contig No. | length | orientation | best hit | NCBI | Repeat region | cp genome hit |
|---|---|---|---|---|---|---|
| 1 | 411 | forward | hypothetical protein [Oryza sativa Indica Group] | ref|XP_005502205.1 | R1 | no |
| 2 | 507 | forward | no significant similarity found | | no | no |
| 3 | 690 | forward | cox1 C-terminus | | | |
| | 351 | forward | no significant similarity found | | no | no |
| | 321 | forward | no significant similarity found | | | |
| 4 | 924 | reverse | p-gene atp8 (T. timopheevi) or atp8-1 [Triticum aestivum] YP_398423 partially | | R9 | no |
| 5 | 699 | reverse | hypothetical protein YYE_00847 [Plasmodium vinckei vinckei] | | no | no |
| | 420 | reverse | hypothetical protein (mitochondrion) [Zea mays subsp. mays] | | | |
| 6 | >268 | forward | no significant similarity found | | R2, R4 | no |
| 7 | 375 | reverse | puroindoline B [Triticum timopheevii subsp. timopheevii] see alignment | | R1 | no |
| | 366 | reverse | no significant similarity found | | | |
| | 249 | reverse | CobB C-terminus | | | |
| 8 | 354 | forward | similarity to rps2 (maybe pseudo rps2??) see contig 13 | gb|AGI48804.1 | R7 | no |
| 9 | 249 | reverse | slight similarity to hypothetical protein JAAARDRAFT_207845 [Jaapia argillacea MUCL 33604] Sequence ID: | gb|KDQ56778.1| | no | no |
| 10 | 1 773 | reverse | photosystem I P700 chlorophyll a apoprotein A1 [Triticum aestivum] | NP_114259.1 GI:14017572 | R6 | yes, insertion in T. timopheevi genome |
| 11 | 771 | forward | ORF256 | | | no |
| | >543 | forward | cox1 N-terminus | | | |
| 12 | 273 | forward | no significant similarity found | | no | no |
| 13 | >458 | reverse | similarity to rps2 see contig 8 | | R7 | no |
| 14 | 381 | forward | no significant similarity found | | no | no |
| 15 | 348 | reverse | no significant similarity found | | R1 | no |
| | 204 | forward | no significant similarity found | | R1 | |
| 16 | 249 | reverse | no significant similarity found | | no | no |
| | 216 | forward | no significant similarity found | | | |
| 17 | 594 | forward | rpl-16 (partially) and rps2 see contig 8 and 13 | | R8 and R7 | no | c—Processing of Orf279 Correlates with the Fertility Restoration Phenotype of Rf1 and Rf3 Transformants Detailed analysis of Orf279 revealed that the first 96 amino acids are identical with the N-terminus of the ATP synthase subunit 8 (FIG. 3A). In addition, the 171 nt upstream of the translation start are identical with the 5' UTR region of the atp8 gene (FIG. 3A).

To analyze the processing of the orf279 transcripts a 5'-RACE analysis was performed. A major amplification product of ~300 nt was detected with GSP1 primers in the Rf1 transformants, whereas in Rf3 transformants a major amplicon of ~400 nt was found (FIG. 3B). In agreement with the origin of the Rf1 restorer from *T. timopheevii* and the Rf3 restorer gene from *T. aestivum*, only the Rf1-specific amplicon was detected in *T. timopheevii* and not the Rf3-specific amplicon. Neither of these two amplicons was detected in the BGA CMS*Fielder sample (FIG. 3B). These results indicate that: (1) orf279 is processed at two different sites—cleavage induced by Rf3 generally occurs upstream of the RNA cleavage induced by Rf1; (2) the endonuclease attracted by Rf3 may sometimes skip the first cleavage site and continue to cleavage site targeted by Rf1.

C—RF Protein Optimization for Improving Suppression of Orf279 Expression

1—Designing and Obtaining Synthetic Rf Proteins SR Orf279 and SR Orf256

A library of 2973 RFL proteins identified by targeted sequence capture from 52 wheat accessions as well as RFL proteins annotated in the Refseqv1.1 Chinese Spring wheat genome (IWGSC) was screened for RFL sequences which according to the PPR code described in Barkan et al. (2012) and patent application WO2013155555 scored highest for RNA binding within orf279 or orf256. The best candidates were analyzed for the presence of a mitochondrial targeting sequence with Predotar (Small et al., 2004) and TargetP (Emanuelsson et al., 2007). The best candidates for either Synthetic Restorer binding to orf279 (SRorf279) or Synthetic Restorer binding to orf256 (SRorf256) were optimized by altering the amino acid combinations at position 5 and 35 according to the PPR code in the PPR motifs that did not form a perfect match with the RNA binding site (FIG. 4). Optimized SRorf279 is depicted in SEQ ID NO: 22 and optimized SRorf256 is depicted in SEQ ID NO: 21. The expression of these optimized sequences can be fused with the expression of a tag sequence depicted in SEQ ID NO: 40, in C-terminal of the optimized sequences.

2—Cloning and Transformation of Optimized SR Orf279 and SR Orf256 Proteins

The optimized SRorf279 and SRorf256 sequences were cloned via Golden Gate reactions between the constitutive *Zea mays* Ubiquitin promoter (proZmUbi, SEQ ID NO: 16) with the *Zea mays* ubiquitin intron (intZmUbi, exemplified in SEQ ID NO: 17) (Christensen, Sharrock, et Quail 1992) and a 3' *Sorghum bicolor* Heat Shock protein (HSP) termination sequence (terSbHSP, depicted in SEQ ID NO: 18) (Putative uncharacterized protein Sb03g006880). The SRorf279 expression cassette depicted in SEQ ID NO: 24 and the SRorf256 expression cassette depicted in SEQ ID NO: 23 were separately cloned into the destination binary plasmid pBIOS10746. The binary destination vector pBIOS10746 is a derivative of the binary vector pMRT (WO2001018192).

Each binary plasmid described above was transformed into *Agrobacterium* EHA105. Each strain obtained was used for transforming BGA CMS*Fielder wheat cultivars as described in WO2000/063398. Wheat transgenic events were generated for each construct described above.

3—Fertility Restoration Phenotyping Assays

All wheat transgenic plants generated above and control fertile plants were grown in a glasshouse under standard wheat growth conditions (16 h of light period at 20° C. and 8 h of dark period at 15° C. with constant 60% humidity) until control grains of the wild type Fielder cultivar reached maturity stage.

Fertility of the transgenic plants was evaluated by counting the number of seeds and empty glumes per spikes on each plant and comparing with the wild type Fielder and BGA CMS*Fielder control plants. Plants are also evaluated by observing anther extrusion.

D—Identification of Orf279

In order to identify orf279 in genomic DNA or RNA samples, the following primers can be used:
  forward primers: SEQ ID NO: 12, SEQ ID NO: 6, SEQ ID NO: 10; and
  reverse primers: SEQ ID NO: 7, SEQ ID NO: 11, SEQ ID NO: 9;

or are constituted by the forward primer SEQ ID NO: 8 and the reverse primer SEQ ID NO: 9.

In order to identify the region in common with atp8 gene sequence, the following primers can be used:
  forward primer: SEQ ID NO:12
  reverse primer: SEQ ID NO:13

FIG. 5 shows the position of these marker sequences on orf279 genomic sequence.

E—RFL29a Protein Optimization for Improving Suppression of Orf279 Expression

1—Designing and Obtaining Synthetic Optimized RFL29a Proteins

The RNA binding of RFL29a sequence within orf279 was analysed according to the PPR code described in Barkan et al. (2012) and patent application WO2013155555. The RFL29a sequence SEQ ID NO: 25 was optimized by altering the amino acid combinations at position 5 and 35 in the PPR motifs that are predicted (using—ΔG values calculated from Yan et al. 2019) to have weak affinity to the corresponding RNA bases (FIG. 6). Optimized RFL29a sequences are depicted in SEQ ID NO: 44 and SEQ ID NO: 45

2—Cloning and Transformation of Optimized RFL29a Proteins

The optimized Rfl29a sequences SEQ ID NO: 46 and SEQ ID NO: 47 were separately cloned via Golden Gate reactions between the TaRFL29b promoter (pro TaRFL29b, SEQ ID NO: 48) and a TaRFL29a termination sequence (ter TaRFL29a, depicted in SEQ ID NO: 49. The optimised RFL29a expression cassettes respectively depicted in SEQ ID NO: 50 and SEQ ID NO: 51 were separately cloned into the destination binary plasmid pBIOS10746. The binary destination vector pBIOS10746 is a derivative of the binary vector pMRT (WO2001018192).

The binary plasmid described above was transformed into *Agrobacterium* EHA105. Each strain obtained was used for transforming BGA CMS*Fielder wheat cultivars as described in WO2000/063398. Wheat transgenic events were generated for each construct described above.

F—Orf279 Diagnostic Marker for the Identification of Plants Harbouring a T-CMS Cytoplasm A KASP design was developed to determine the presence or absence of the orf279 T-CMS in a plant material.

In order to determine if the orf279 T-CMS is present in a material, three primers were defined according to the PCR-based KASP technology:

the oligonucleotide AS1 (SEQ ID NO: 52) is specific from orf279 (sterile) and the genomic sequence from ChrUn ChineseSpring (IWGSC_V1).

the oligonucleotide AS2 (SEQ ID NO: 53) is specific from the normal cytoplasmic sequence (fertile).

the oligonucleotide C (SEQ ID NO: 54) is common between sequences.

The couple AS2/C is specific from the normal cytoplasmic sequence (fertile). The primer position has been optimized to exclude genomic paralogs amplification (more than 10 genomic paralogs copy from the fertile cytoplasmic sequence have been identified).

The couple AS1/C is specific of the orf279 T-CMS cytoplasmic sequence (sterile).

These three primers may be used simultaneously in a PCR amplification experiment (Kaspar protocol LGC Genomics) starting with genomic DNA (hybridization temperature=57° C.). End point fluorescence read, and clusters analysis of the samples reveal:

Vic fluorescence for sterile plants
Fam fluorescence for fertile plants

In FIG. 7, the cluster on the right side is the amplification of the normal cytoplasm with AS2 in fertile plants. The cluster on the left side is the amplification of the orf279 with AS1 in sterile plants (plants harbouring a T-CMS cytoplasm).

BIBLIOGRAPHY

Kay R, et al. (1987). Duplication of CaMV 35S promoter sequences creates a strong enhancer for plant genes. Science 236:1299-1302.

McElroy D et al. (1990). Isolation of an Efficient Actin Promoter for Use in Rice Transformation. The Plant Cell, Vol. 2, 163-171.

Depigny-This D et al, 1992. The cruciferin gene family in radish. Plant Molecular Biology, 20: 467-479.

Verdaguer et al. (1996). Isolation and expression in transgenic tobacco and rice plants, of the cassava vein mosaic virus (CVMV) promoter. Plant Molecular Biology 31: 1129-1139.

Christensen A H and Quail P H (1996). Ubiquitin promoter-based vectors for high-level expression of selectable and/or screenable marker genes in monocotyledonous plants. Transgenic Res, May; 5(3):213-8.

Götz H et al. (2011). Transgene Expression Systems in the Triticeae Cereals. Journal of Plant Physiology 168, no. 1: 30-44. doi:10.1016/j.jplph.2010.07.007.

Jones H D (2015). Wheat Biotechnology: Current Status and Future Prospects. K. Azhakanandam et al. (eds.), Recent Advancements in Gene Expression and Enabling Technologies in Crop Plants, DOI 10.1007/978-1-4939-2202-4_8.

Huang et al. (2009). Refining the Definition of Plant Mitochondrial Presequences through Analysis of Sorting Signals, N-Terminal Modifications, and Cleavage Motifs. Plant Physiology, July 2009, Vol. 150, pp 1272-1285.

Barkan A et al. 2012, PLosS Genet. A combinatorial amino acid code for RNA recognition by pentatricopeptide repeat proteins. 8(8):e1002910.

Christensen et al. (1992). Maize polyubiquitin genes: structure, thermal perturbation of expression and transcript splicing, and promoter activity following transfer to protoplasts by electroporation. Plant Mol Biol. 1992 February; 18(4):675-89.

Triboush et al. (1998), A Method for Isolation of Chloroplast DNA and Mitochondrial DNA from Sunflower. Plant Molecular Biology Reporter 16(2):183-183.

Ogihara et al. (2005). Structural dynamics of cereal mitochondrial genomes as revealed by complete nucleotide sequencing of the wheat mitochondrial genome. Nucleic Acids Res. 2005:6235-6250.

Song and Hedgcoth (1994A). A chimeric gene (orf256) is expressed as protein only in cytoplasmic male-sterile lines of wheat. Plant Mol Biol. 1994 October; 26(1):535-9.

Song and Hedgcoth (1994B). Influence of nuclear background on transcription of a chimeric gene orf256 and cox1 in fertile and cytoplasmic male sterile wheats. Genome, vol. 37.

Small et al. (2004). Predotar: A tool for rapidly screening proteomes for N-terminal targeting sequences. Proteomics. 2004 June; 4(6):1581-90.

Emanuelsson et al. (2007). Locating proteins in the cell using TargetP, SignalP and related tools. Nat Protoc. 2007; 2(4):953-71.

The invention claimed is:

1. A method for identifying a functional Rf gene encoding a protein able to bind to orf279 RNA, wherein the method comprises the steps of:

a. predicting a target RNA sequence for protein encoded by an Rf gene identified in a wheat plant genome according to the PPR code, comprising:

determining all possible ribonucleotides for each amino acid combination at position 5 and 35 of the PPR motif, and selecting the target RNA sequence scoring highest for RNA binding to the corresponding PPR, b. aligning the predicted target RNA sequence with SEQ ID NO: 3, c. identifying the Rf gene, encoding for a protein, able to bind to a target RNA sequence that shows at least 95% identity to SEQ ID NO: 3, d. optionally optimizing the sequence of the selected Rf protein by changing amino acids at position 5 and 35 of the PPR motif to improve match according to the PPR code with SEQ ID NO: 3, and e. validating the binding of said protein to orf279 RNA, comprising:

transforming a wheat plant comprising a sterile cytoplasm expressing orf279, with a vector expressing the identified Rf gene; and detecting the level of orf279 expression in the transformed plant.

2. The method according to claim 1, comprising optimizing the sequence of the selected Rf protein by changing amino acids at position 5 and 35 of the PPR motif to improve match according to the PPR code with SEQ ID NO: 3.

3. The method according to claim 2, wherein the Rf gene is an Rf1 gene or an Rf3 gene.

* * * * *